United States Patent
Bandi et al.

(10) Patent No.: US 10,370,405 B2
(45) Date of Patent: Aug. 6, 2019

(54) C-3 NOVEL TRITERPENONE WITH C-28 AMIDE DERIVATIVES AS HIV INHIBITORS

(71) Applicant: HETERO LABS LIMITED, Hyderabad (IN)

(72) Inventors: Parthasaradhi Reddy Bandi, Hyderabad (IN); Rathnakar Reddy Kura, Hyderabad (IN); David Krupadanam Gazula Levi, Hyderabad (IN); Panduranga Reddy Adulla, Hyderabad (IN); Eswara Rao Bammidi, Hyderabad (IN); Bhaskar Reddy Kasireddy, Hyderabad (IN); Sudhakar Neela, Hyderabad (IN); Carl Thomas Wild, Gaithersburg, MD (US); David Eugene Martin, Shawnee, OK (US); Theodore John Nitz, Boyds, MD (US)

(73) Assignee: HETERO LABS LIMITED, Hyderabad (IN)

( * ) Notice: Subject to any disclaimer, the term of this patent is extended or adjusted under 35 U.S.C. 154(b) by 0 days.

(21) Appl. No.: 15/558,677

(22) PCT Filed: Mar. 12, 2016

(86) PCT No.: PCT/IB2016/051424
§ 371 (c)(1),
(2) Date: Sep. 15, 2017

(87) PCT Pub. No.: WO2016/147099
PCT Pub. Date: Sep. 22, 2016

(65) Prior Publication Data
US 2018/0237472 A1 Aug. 23, 2018

(51) Int. Cl.
A61P 31/18 (2006.01)
C07J 63/00 (2006.01)

(52) U.S. Cl.
CPC ............ *C07J 63/008* (2013.01); *A61P 31/18* (2018.01)

(58) Field of Classification Search
CPC .............................. C07J 63/008; A61P 31/18
USPC ....................................................... 514/326
See application file for complete search history.

(56) References Cited

U.S. PATENT DOCUMENTS

| | | |
|---|---|---|
| 4,598,095 A | 7/1986 | Nishimura et al. |
| 5,679,828 A | 10/1997 | Lee et al. |
| 6,451,851 B1 | 9/2002 | Sumegi |
| 6,670,345 B1 | 10/2003 | Ramadoss et al. |
| 7,923,573 B2 | 4/2011 | Tamaki et al. |
| 8,802,727 B2 | 8/2014 | Partharadhi Reddy et al. |
| 9,067,966 B2 | 6/2015 | Parthasaradhi Reddy et al. |
| 9,637,516 B2 | 5/2017 | Parthasaradhi Reddy et al. |
| 9,868,758 B2 * | 1/2018 | Bandi ............... C07J 63/008 |
| 2002/0068757 A1 | 6/2002 | Lin et al. |
| 2004/0204389 A1 | 10/2004 | Chen et al. |
| 2006/0194774 A1 | 8/2006 | Selzer et al. |
| 2006/0205697 A1 | 9/2006 | Robinson et al. |
| 2008/0207573 A1 | 8/2008 | Yager et al. |
| 2008/0214516 A1 | 9/2008 | Selzer et al. |
| 2009/0023698 A1 | 1/2009 | Krasutsky et al. |
| 2011/0015196 A1 | 1/2011 | Parthasaradhi Reddy et al. |
| 2011/0077228 A1 | 3/2011 | Moinet et al. |
| 2011/0152229 A1 | 6/2011 | Chen et al. |
| 2011/0218204 A1 | 9/2011 | Parthasaradhi Reddy et al. |
| 2014/0221328 A1 | 8/2014 | Parthasaradhi Reddy et al. |
| 2015/0119373 A1 | 4/2015 | Reddy et al. |
| 2015/0337004 A1 | 11/2015 | Reddy et al. |
| 2017/0008921 A1 | 1/2017 | Reddy et al. |
| 2017/0129916 A1 | 5/2017 | Parthasaradhi Reddy et al. |
| 2017/0129917 A1 | 5/2017 | Bandi et al. |
| 2018/0215780 A1* | 8/2018 | Parthasaradhi Reddy ............ A61P 31/18 |

FOREIGN PATENT DOCUMENTS

| | | |
|---|---|---|
| CA | 2223513 A1 | 12/1996 |
| CA | 2767642 C | 1/2011 |
| CN | 1861627 A | 11/2006 |
| CN | 101287744 A | 10/2008 |

(Continued)

OTHER PUBLICATIONS

Martin; Antiviral Chemistry and Chemotherapy 2008, 19, 107-113. (Year: 2008).*

(Continued)

*Primary Examiner* — Daniel R Carcanague
(74) *Attorney, Agent, or Firm* — Cantor Colburn LLP

(57) ABSTRACT

The invention relates to C-3 novel triterpenone with C-28 amide derivatives, related compounds, and pharmaceutical compositions useful for the therapeutic treatment of viral diseases and particularly HIV mediated diseases (formula 1).

Formula (1)

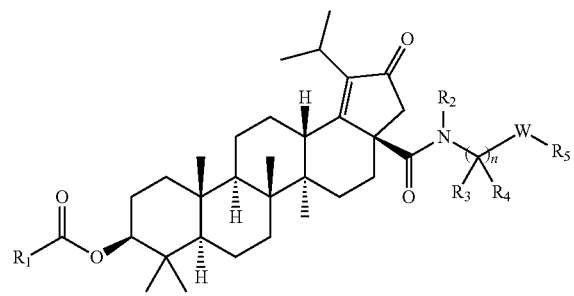

9 Claims, No Drawings

(56) References Cited

FOREIGN PATENT DOCUMENTS

| | | |
|---|---|---|
| EP | 1218402 B1 | 5/2004 |
| WO | 199502071 A1 | 1/1995 |
| WO | 9858675 | 12/1998 |
| WO | 0046235 A1 | 8/2000 |
| WO | 0107646 A2 | 2/2001 |
| WO | 0165957 A2 | 9/2001 |
| WO | 02091858 A1 | 11/2002 |
| WO | 2003037908 A1 | 5/2003 |
| WO | 2005090380 A1 | 9/2005 |
| WO | 2006053255 A2 | 5/2006 |
| WO | 2006105356 A2 | 10/2006 |
| WO | 2007002411 A1 | 1/2007 |
| WO | 2007141383 A1 | 12/2007 |
| WO | 2007141389 A1 | 12/2007 |
| WO | 2007141390 A1 | 12/2007 |
| WO | 2007141391 A1 | 12/2007 |
| WO | 2007141392 A2 | 12/2007 |
| WO | 2008057420 A2 | 5/2008 |
| WO | 2008091532 A1 | 7/2008 |
| WO | 2008127364 A2 | 10/2008 |
| WO | 2009082818 A1 | 7/2009 |
| WO | 2009082819 A1 | 7/2009 |
| WO | 2009100532 A1 | 8/2009 |
| WO | 2010132334 A1 | 11/2010 |
| WO | 2011007230 A1 | 1/2011 |
| WO | 2011100308 A1 | 8/2011 |
| WO | 2011153315 A1 | 12/2011 |
| WO | 2011153319 A1 | 12/2011 |
| WO | 2012095705 A1 | 7/2012 |
| WO | 2013001144 A1 | 1/2013 |
| WO | 2013020245 A1 | 2/2013 |
| WO | 2013090664 A1 | 6/2013 |
| WO | 2013090683 A1 | 6/2013 |
| WO | 2013117137 A1 | 8/2013 |
| WO | 2013160810 A2 | 10/2013 |
| WO | 2014093941 A1 | 6/2014 |
| WO | 2014105926 A1 | 7/2014 |
| WO | 2015198263 A2 | 12/2015 |
| WO | 2016178092 A2 | 11/2016 |
| WO | 2017017630 A1 | 2/2017 |
| WO | WO-2017021922 A1 * | 2/2017 ............. C07C 53/00 |
| WO | WO-2017064628 A1 * | 4/2017 ............. A61K 31/00 |
| WO | WO-2017115329 A1 * | 7/2017 |
| WO | WO-2017149518 A1 * | 9/2017 |
| WO | WO-2018025247 A1 * | 2/2018 ............. C07J 53/00 |
| WO | WO-2018029602 A1 * | 2/2018 ............. C07J 53/00 |
| WO | WO-2018029604 A1 * | 2/2018 ............. C07J 53/00 |
| WO | WO-2018029610 A1 * | 2/2018 ............. C07J 53/00 |
| WO | WO-2018069857 A1 * | 4/2018 |

OTHER PUBLICATIONS

Flekhter Et Al. "Synthesis and Antiinflammatory Activity of New Acylated Betulin Derivatives," Pharmaceutical Chemistry Journal 2002, vol. 36, Issue 9, pp. 29-32.

Fujioka et al. "Anti-AIDS Agents, 11. Betulinic Acid and Platanic Acid as anti-HIV Principles from Syzigium Claviflorum, and the Anti-HIV Activity of Structurally Related Triterpenoids", Journal of Natural Products, 1994, vol. 57, No. 2, pp. 243-247.

Gerrish Et Al., "Triterpene based compounds with potent anti-maturation activity against HIV-1," Bioorganic & Medicinal Chemistry Letters, 2008, vol. 18, Issue 24, pp. 6377-6380.

Greene, T. W. and P. G. M. Wuts, "Protective Groups in Organic Synthesis", 3rd edition, John Wiley & Sons, Inc., New York, 1999.

Harrington et al., "Direct detection of infectious HIV_1 in blood using a centrifugation-indicator cell assay", Journal of Virological Methods, 2000, vol. 88, pp. 111-115.

Hashimoto, F., et al., "Anti-Aids Agents—XXVIL. Synthesis and Anti-HIV Activity of Betulinic Acid and Dihydrobetulinic Acid Derivatives", Bioorganic & Medicinal Chemistry, 1997, vol. 5, No. 12, pp. 2133-2143.

Jeong H-J et al: "Preparation of amino acid conjugates of betulinic acid with activity against human melanoma", Bioorganic & Medicinal Chemistry Letters, Pergamon, Amsterdam, NL, vol. 9, No. 8, Apr. 19, 1999, pp. 1201-1204.

Kanamoto et al., "Anti-Human Immunodeficiency Virus Activity of YK-FH312 (a Betulinic Acid Derivative), a Novel Compound Blocking Viral Maturation", Antimicrobial Agents and Chemotherapy, 2001, pp. 1225-1230.

Kashiwada et al., "Betulinic Acid and Dihydrobetulinic Acid Derivatives as Potent Anti-HIV Agents", J. Med. Chem. 1996, 39, pp. 1016-1017.

Koyanagi et al., "Selective Cytotoxicity of AIDS Virus Infection Towards HTLV-I-Transformed Cell Lines", Int. J. Cancer, 1985, vol. 36, pp. 445-451.

Li et al., "PA-457: A potent HIV inhibitor that disrupts core condensation by targeting a late step in Gag processing", Proc Natl. Acad. Sci. 2003, pp. 13555-13560.

Meek et al., "Inhibition of HIV-1 protease in infected T-lymphocytes by synthetic peptide analogues", Nature, 1990, vol. 343, pp. 90-92.

Mimoto et al., "Structure-Activity Relationship of Small-Sized HIV Protease Inhibitors Containing Allophenylnorstatine", J. Med. Chem., 1999, vol. 42, No. 10, pp. 1789-1802.

Mitsuya et al., "Inhibition of the in vitro infectivity and cytopathic effect of human T-lymphotrophic virus type III/lymphadenopathy-associated virus (HTLV-III/LAV) by 2',3'-dideoxynucleosides", Proc. Natl. Acad. Sci. USA, 1986, vol. 83, pp. 1911-1915.

Moglioni et al., "Divergent Routes to Chiral Cyclobutane Synthons from (−)-a-Pinene and Their Use in the Steroselective Synthesis of Dehydro Amino Acids", J. Org. Chem. 2000, 65, pp. 3934-3940.

Mosmann, T., Rapid Colorimetric Assay for Cellular Growth and Survival: Application to Proliferation and Cytotoxicity Assays. Journal of Immunological Methods, 65 (1983) 55-63.

Nair et al., "A Facile and Efficient Synthesis of 3,3-Dimethyl Isopropylidene Proline From (+)-3-Carene", J. Org. Chem., 2010, vol. 75, No. 4, pp. 1285-1288.

Pau et al., Antiretroviral Therapy, Infect. Dis. Clin. N. Am., 2014, 28, 371-402.

Popik et al., "Human Immunodeficiency Virus Type 1 Uses Lipid Raft-Colocalized CD4 and Chemokine Receptors for Productive Entry into CD4+ T Cells", J. of Virology, 2002, pp. 4709-4722.

Qian Et Al., "Anti-AIDS Agents 90. Novel C-28 Modified Bevirimat Analogues as Potent HIV Maturation Inhibitors," Journal of Medicinal Chemistry, 2012, vol. 55, Issue 18, pp. 8128-8136.

Qian Et Al., "Anti-AIDS Agents, Synthesis, Metabolic Stability Assessment, and Antiviral Evaluation," Journal of Medicinal Chemistry, 2009, vol. 52, Issue 10, pp. 3248-3258.

Qian Keduo et al: "Anti-AIDS agents 81. Design, synthesis, and structure-activity relationship study of betulinic acid and moronic acid derivatives as potent HIV maturation inhibitors.", Journal of Medicinal Chemistry Apr. 22, 2010, vol. 53, No. 8, pages.

Ravi et al, "HIV-1 long terminal repeat promoter regulated dual reporter: Potential use in screening of transcription modulators", Analytical Biochemistry, 2007, vol. 360, pp. 315-317.

Roda Rani et al., "A conserved molecular action of native and recombinant Epap-1 in inhibition of HIV-1 gp120 mediated viral entry", Archives of Biochemistry and Biophysics, 2006, vol. 456, pp. 79-92.

Roos et al., "LuSIV Cells: A Reporter Cell Line for the Detection and Quantation of a Single Cycle of HIV and SIV Replication", Virology, 2000, vol. 273, pp. 307-315.

Sakalian et al., "3-O-(3',3'-Dimethysuccinyl) Betulinic Acid Inhibits Maturation of the Human Immunodeficiency Virus Type 1 Gag Precursor Assemble In Vitro", J. of Virology, 2006, pp. 5716-5722.

Schwartz et al., "A Rapid Colorimetric Test for the Study of Anti-HIV Agents", AIDS Research and Human Retroviruses, 1988, vol. 4, No. 6, pp. 441-448.

Silverman, "The Organic Chemistry of Drug Design and Drug Action," Academic Press; 1992, pp. 352-355.

Sun, I., et al., "Anti-AIDS Agents, 34. Synthesis and Structure-Activity Relationships of Betulin Derivatives as Anti-HIV Agents", J. Med. Chem. 1998, vol. 41, pp. 4648-4657.

(56) References Cited

OTHER PUBLICATIONS

Taiwo et al., "Unmet therapeutic needs in the new era of combination antiretroviral therapy for Hiv-1", J. antimicrob Chemother 2010; 65: 1100-1107.

Tyle, P., "Iontophoretic Devices for Drug Delivery", Pharmaceutical Research, vol. 3, No. 6, 1986, 318-326.

Uckun et al., "TXU (Anti-CD7)-Pokeweed Antiviral Protein as a Potent Inhibitor of Human Immunodeficiency Virus", Antimicrobial Agents and Chemotherapy, Feb. 1998, vol. 42, No. 2, pp. 383-388.

Weislow et al., New Soluble-Formazan Assay for HIV-1 Cytopathic Effects: Application to High-Flux Screening of Synthetic and Natural Products for AIDS-Antiviral Activity, J. Natl. Cancer Inst., 1989, 81, pp. 577-586.

Zhou et al., "Inhibition of HIV-1 Maturation via Drug Association with the Viral Gag Protein in Immature HIV-1 Particles", J. of Bio. Chem. vol. 280, No. 51, pp. 42149-42155, 2005.

Zhou et al., "Small-Molecule Inhibition of Human Immunodeficiency Virus Type 1 Replication by Specific Targeting of the Final Step of Virion Maturation", J. of Virology, 2004, pp. 922-929.

Zhu, YM., et al., "Synthesis and Anti-HIV Activity Oleanolic Acid Derivatives", Bioorganic & Medicinal Chemistry Letters, 2001, vol. 11, pp. 3115-3118.

International Search Report; International Application No. PCT/IB2016/051424; International Filing Date Mar. 12, 2016; dated Aug. 29, 2016; 4 pages.

Written Opinion for International Application No. PCT/IB2016/051424, International Filing Date Mar. 12, 2016, dated Aug. 29, 2017, 7 pages.

Aguado et al., "Enantidivergent synthesis of cyclobutyl-(Z)-a,β-dehydro-a-amino acid derivatives from (−)-cis-pinononic acid", Tetrahedron: Asymmetry 14, 2003, pp. 217-223.

Aguilera et al., "Stereodivergent synthesis of the first bis(cyclobutane) y-dipeptides and mixed y-oligomers", Tetrahedron: Asymmetry 19, 2008, pp. 302-308.

Antimonova et al., "Synthesis of Betulonic Acid Amindes", Chemistry of Natural Compounds, 2008, vol. 44, No. 3, pp. 327-333.

Averett, D. "Anti-HIV compound assessment by two novel high capacity assays", Journal of Virological Methods, 1989, vol. 23, pp. 263-276.

Balzarini et al., "9-(2phosphonylmethoxyethyl)adenine (PMEA) effectively inhibits retrovirus replication in vitro and simian immunodeficiency virus infection in rhesus monkeys", AIDS, 1991, 5, pp. 21-28.

Barre-Sinoussi et al., "Isolation of a T-Lymphotropic Retrovirus from a Patient at Risk for Acquired Immune Deficiency Syndrome (AIDS)", Science, 1983, vol. 220, pp. 868-871.

Broder et al., "A Pathogenic Retrovirus (HTLA-III) Linked to AIDS", The New England Journal of Medicine, 1984, vol. 311, No. 20, pp. 1292-1297.

Cecilia et al., "Neutralization Profiles of Primary Human Immunodeficiency Virus Type 1 Isolates in the Context of Coreceptor Usage", Journal of Virology, Sep. 1998, vol. 72, No. 9, pp. 6988-6996.

Clark et al., "Synthesis and antiviral activity of 2'-deoxy-2'-fluoro-2'-C-methyl purine nucleosides as inhibitors of hepatitis C virus RNA replication", Bioorganic & Medicinal Chemistry Letters 16 (2006), pp. 1712-1715.

Cole, S.P.C., "Rapid chemosensitivity testing of human lung tumor cells using the MTT assay", Cancer Chemotherapy and Pharmacology, 1986, 17, pp. 259-263.

Connor et al., "Characterization of the Functional Properties of env Genes from Long-Term Survivors of Human Immunodeficiency Virus Type 1 Infection", Journal of Virology, 1996, vol. 70, No. 8, pp. 5306-5311.

Daluge et al., "5-Chloro-2',3'-Dideoxy-3'-Fluorouridine (935U83), a Selective Anti-Human Immunodeficiency Virus Agent with an Improved Metabolic and Toxicological Profile", Antimicrobial Agents and Chemotherapy, 1994, vol. 38, No. 7, pp. 1590-1603.

Dang et al. "Betulinic Acid Derivatives as Human Immunodeficiency Virus Type 2 (HIV-2) Inhibitors" J. Med. Chem., 2009, 52 (23), pp. 7887-7891.

Erice et al., "Anti-Human Immunodeficiency Virus Type 1 Activity of an Anti-CD4 Immunoconjugate Containing Pokeweed Antiviral Protein", Antimicrobial Agents and Chemotherapy, Apr. 1993, vol. 37, No. 4, pp. 835-838.

Fedyuk N.V. et al., Problems of Virology 1992, (3) 135, Abstract Only, 1 page.

Flekhter et al, "Synthesis and Antiinflammatory Activity of New Acylated Betulin Derivatives", Pharmaceutical Chemistry Journal, 2002, vol. 36, No. 9, pp. 488-491.

* cited by examiner

C-3 NOVEL TRITERPENONE WITH C-28 AMIDE DERIVATIVES AS HIV INHIBITORS

CROSS-REFERENCE TO RELATED APPLICATIONS

This application is a National Stage application of PCT/IB2016/051424, filed 12 Mar. 2016, which claims the benefit of Indian provisional application no 1286/CHE/2015 filed on 16 Mar. 2015 which are hereby incorporated by reference in its their entirety.

FIELD OF THE INVENTION

The present invention relates to C-3 novel triterpenone with C-28 amide derivatives and related compounds, compositions useful for therapeutic treatment of viral diseases and particularly HIV mediated diseases.

BACKGROUND OF THE INVENTION

The Human Immunodeficiency Virus (HIV) has now been established as the causative agent of the Acquired Immunodeficiency Syndrome (AIDS) for over 20 years (Science 1983, 220, 868-871; N. Eng. J. Med. 1984, 311, 1292-1297). AIDS is characterized by the destruction of the immune system, particularly of CD4+ T-cells. HIV is a retrovirus, and the HIV life cycle encompasses several crucial steps, starting from the attachment of the virus to the host cell membrane and finishing with the release of progeny virons from the cell.

The natural compound betulinic acid, isolated from *Syzygium clavifolium* and several other plant species was found to possess anti-HIV activity. Chemical modifications were undertaken by several research groups in an attempt to identify potent anti-HIV agents by making semi-synthetic analogs of betulinic acid, leading to the discovery of bevirimat as a compound with a novel mechanism of action (J. Nat. Prod. 199457(2):243-7; J. Med. Chem. 1996, 39(5), 1016). Further studies shown that bevirimat acts by disrupting Gag processing (Proc. Natl. Acad. Sci. USA 2003, 100(23):13555-60; Antimicrob. Agents. Chemother. 2001, 45(4), 1225-30; J. Virol. 2004, 78(2): 922-9; J. Biol. Chem. 2005, 280(51):42149-55; J. Virol. 2006, 80(12): 5716-22) and to be a first-in-class maturation inhibitor with a potent activity against HIV-1. Bevirimat went up to phase 2 clinical trials, in clinic despite optimal plasma concentrations, not all patients given bevirimat have a robust viral load reduction. It was reported that non-respondant patients had more frequent base line Gag polymorphisms near the capsid SP-1 cleavage site than responders. (HIV gag polymorphism determines treatment response to bevirimat. XVII international HIV drug resistance work shop Jun. 10-14, 2008, Sitges, Spain).

Encouraged by these developments, medicinal chemists started exploring betulinic acid derivatives and related compounds intensively for their therapeutic activities. For example, WO 2014/093941 describes pharmaceutical compositions of betulin derivatives; WO 2013/117137 describes lupane triterpenoids derivatives and pharmaceutical use thereof; WO 2013/020245 describes carbonyl derivatives of betulin; WO 2013/090664 describes preparation of betulin derivatives for the treatment of HIV; WO 2013/020246 describes preparation of methylene derivatives of betulin useful for the treatment of HIV; WO 2011/100308 describes preparation of betulin derivatives for the treatment of HIV-1; WO 2009/082819 describes preparation of 17-amino lupane derivatives as anti-HIV agents; WO 2009/082818 describes preparation of C21-keto lupane derivatives for the treatment of HIV infections.

Given the fact of the world wide epidemic level of AIDS, there is a strong continued need for new effective drugs for treatment of HIV infected patients, disease conditions and/or disorders mediated by HIV by discovering new compounds with novel structures and/or mechanism of action(s).

SUMMARY OF THE INVENTION

The present invention relates to the compounds of the formula (1)

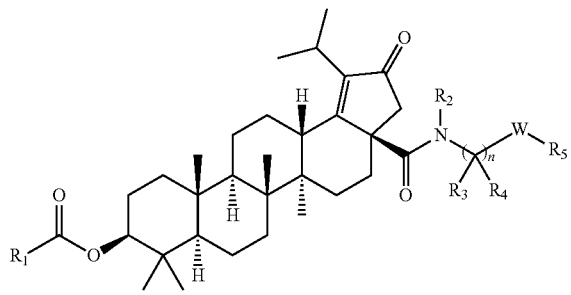

Formula (1)

wherein, $R_1$ can be substituted or unsubstituted alkyl,

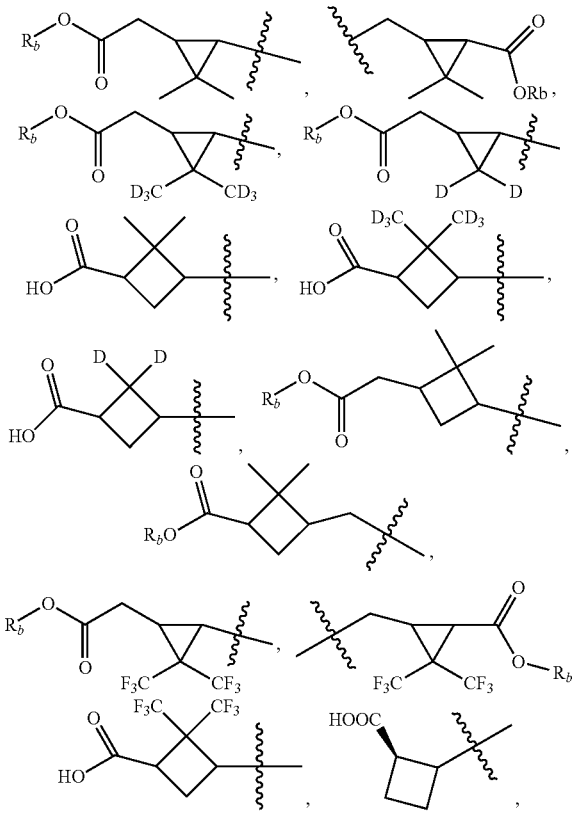

-continued

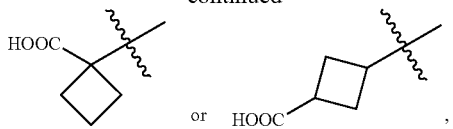

(wherein $R_b$ can be hydrogen, substituted or unsubstituted alkyl, or substituted or unsubstituted cycloalkyl);

$R_2$ can be hydrogen, substituted or unsubstituted alkyl, substituted or unsubstituted alkoxylalkoxy or substituted or unsubstituted amino alkyl;

$R_3$ can be substituted or unsubstituted alkyl, substituted or unsubstituted amine, substituted or unsubstituted cycloalkyl, substituted or unsubstituted heterocyclyl or substituted or unsubstituted heteroaryl;

$R_2$ and $R_3$ can be taken together with the N-atom and C-atom to which they are attached to form substituted or unsubstituted 4-7 membered N-contained heterocyclyl; wherein the substituent can be heterocyclyl;

$R_4$ can be hydrogen, substituted or unsubstituted alkyl, substituted or unsubstituted amine, substituted or unsubstituted cycloalkyl, substituted or unsubstituted heterocyclyl or substituted or unsubstituted heteroaryl;

W can be absent, —$CH_2$—, substituted or unsubstituted alkyl, substituted or unsubstituted heterocyclyl or substituted or unsubstituted heteroaryl;

$R_5$ can be hydrogen, hydroxy, substituted or unsubstituted aryl, substituted or unsubstituted heterocyclyl or substituted or unsubstituted heteroaryl; wherein the substituent can be halo or hydroxyl alkyl;

'n' can be an integer selected from 0-1;

Pharmaceutically acceptable salts of the compounds of the formula (1) are also contemplated. Likewise, pharmaceutically acceptable solvates, including hydrates of the compounds of the formula (1) are contemplated.

It should be understood that the formula (1) structurally encompasses all stereoisomers, including enantiomers, diastereomers, racemates, and combinations thereof which may be contemplated from the chemical structure of the genus described herein.

It should be understood that the formula (1) structurally encompasses all tautomers.

Also contemplated are prodrugs of the compounds of the formula (1), including ester prodrugs.

According to one embodiment, there is provided a compound of formula (1), wherein $R_1$ is

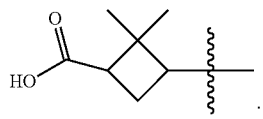

According to another embodiment, there is provided a compound of formula (1), wherein $R_2$ is hydrogen.

According to yet another embodiment, there is provided a compound of formula (1), wherein $R_2$ is N, N-dimethylethanamine.

According to yet another embodiment, there is provided a compound of formula (1), wherein $R_3$ is methyl.

According to yet another embodiment there is provided a compound of formula (1), wherein $R_4$ is hydrogen and methyl.

According to yet another embodiment there is provided a compound of formula (1), wherein $R_2$ and $R_3$ are together with the N-atom and C-atom to which they are attached to form pyrrolidine and the substituent is pyrrolidine.

According to yet another embodiment there is provided a compound of formula (1), wherein $R_5$ is hydrogen.

According to yet another embodiment there is provided a compound of formula (1), wherein $R_5$ is hydroxyl.

According to yet another embodiment there is provided a compound of formula (1), wherein $R_5$ is phenyl substituted with fluoro and chloro According to yet another embodiment there is provided a compound of formula (1), wherein $R_5$ is pyrrolidine.

According to yet another embodiment there is provided a compound of formula (1), wherein $R_5$ is pyrrolidine substituted with fluoro and hydroxymethyl.

According to yet another embodiment there is provided a compound of formula (1), wherein $R_5$ is piperidine substituted with fluoro.

According to yet another embodiment there is provided a compound of formula (1), wherein $R_5$ is pyridine According to yet another embodiment, there is provided a compound of formula (1), wherein W is absent.

According to yet another embodiment, there is provided a compound of formula (1), wherein W is —$CH_2$—

According to yet another embodiment, there is provided a compound of formula (1), wherein W is imidazole.

According to yet another embodiment, there is provided a compound of formula (1), wherein 'n' is 0.

According to yet another embodiment, there is provided a compound of formula (1), wherein 'n' is 1.

Below are the representative compounds, which are illustrative in nature only and are not intended to limit to the scope of the invention (Nomenclature has been generated from ChemBioDraw Ultra 13.0 version):

(1R,3S)-3-((((3aR,5aR,5bR,7aR,9S,11aR,11bR,13aS)-1-isopropyl-5a,5b,8,8,11a-pentamethyl-2-oxo-3a-((S)-2-(5-phenyl-1H-imidazol-2-yl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Example 1), (1R,3S)-3-((((3aR,5aR,5bR,7aR,9S,11aR,11bR,13aS)-3a-((S)-2-(5-(4-fluorophenyl)-1H-imidazol-2-yl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Example 2), (1R,3S)-3-((((3aR,5aR,5bR,7aR,9S,11aR,11bR,13aS)-1-isopropyl-5a,5b,8,8,11a-pentamethyl-2-oxo-3a-((S)-2-(5-(pyridin-3-yl)-H-imidazol-2-yl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid (Example 3), (1R,3S)-3-((((3aR,5aR,5bR,7aR,9S,11aR,11bR,13aS)-3a-((R)-[1,3'-bipyrrolidine]-1'-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethyl cyclobutane-1-carboxylic acid (Example 4), (1R,3S)-3-((((3aR,5aR,5bR,7aR,9S,11aR,11bR,13aS)-3a-((S)-2-(((S)-2-(hydroxy methyl)pyrrolidin-1-yl)methyl) pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Example 5), (1R,3S)-3-((((3aR,5aR,5bR,7aR,9S,11aR,11bR,13aS)-3a-((S)-2-((3,3-difluoropyrrolidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Example 6), (1R,3S)-3-((((3aR,5aR,5bR,7aR,9S,11aR,11bR,13aS)-3a-((S)-2-((4,4-difluoro piperidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclo penta[a]chrysen-9-yl)oxy)carbonyl)-2,2-dimethylcyclobutane-1-carboxylic acid (Example 7), (1R,3S)-3-((((3aR,5aR,5bR,7aR,9S,11aR,11bR,13aS)-1-isopropyl-5a,5b,8,8,11a-pentamethyl-2-oxo-3a-((2-(5-phenyl-1H-imidazol-2-yl)propan-2-yl)carbamoyl)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Example 8), (1R,3S)-3-((((3aR,5aR,5bR,7aR,9S,11aR,11bR,13aS)-3a-((S)-2-(2-hydroxypropan-2-yl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Example 9), (1R,3S)-3-((((3aR,5aR,5bR,7aR,9S,11aR,11bR,13aS)-3a-((S)-2-((4-fluoropiperidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Example 10), (1R,3S)-3-((((3aR,5aR,5bR,7aR,9S,11aR,11bR,13aS)-3a-((2-(5-(4-chlorophenyl)-1H-imidazol-2-yl)propan-2-yl)carbamoyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Example 11), (1R,3S)-3-((((3aR,5aR,5bR,7aR,9S,11aR,11bR,13aS)-1-isopropyl-5a,5b,8,8,11a-pentamethyl-3a-((2-methyl-1-(pyrrolidin-1-yl)propan-2-yl)carbamoyl)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Example 12), (1R,3S)-3-((((3aR,5aR,5bR,7aR,9S,11aR,11bR,13aS)-1-isopropyl-5a,5b,8,8,11a-pentamethyl-2-oxo-3a-((S)-2-(pyrrolidin-1-ylmethyl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Example 13), (1R,3S)-3-((((3aR,5aR,5bR,7aR,9S,11aR,11bR,13aS)-3a-((4-chlorobenzyl)(2-(di methylamino)ethyl)carbamoyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid (Example 14) and (1R,3S)-3-((((3aR,5aR,5bR,7aR,9S,11aR,11bR,13aS)-3a-((1-hydroxy-2-methyl propan-2-yl)carbamoyl)-1-isopropyl-5a,5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-9-yl)oxy)carbonyl)-2,2-dimethylcyclobutane-1-carboxylic acid (Example 15) or pharmaceutically acceptable salts, solvates, including hydrates and prodrugs of compounds are also contemplated.

The present invention also provides a pharmaceutical composition that includes at least one compound as described herein and at least one pharmaceutically acceptable excipient (such as a pharmaceutically acceptable carrier or diluent). Specifically, the pharmaceutical composition comprises a therapeutically effective amount of at least one compound described herein. The compound(s) present in the composition may be associated with a pharmaceutically acceptable excipient (such as a carrier or a diluent) or may be diluted by a carrier, or enclosed within a carrier which may be in the form of a capsule, sachet, or other container.

The compounds and pharmaceutical compositions described herein are useful in the treatment of diseases, conditions and/or disorders mediated by viral infections.

The present invention further provides a method of treating a disease, condition and/or disorder mediated by viral infections in a subject in need thereof by administering to the subject one or more compounds described herein in a therapeutically effective amount to cause that infection, specifically in the form of a pharmaceutical composition.

Also provided herein are processes for preparing compounds described herein.

The invention provides a method for preventing; ameliorating or treating a HIV mediated disease, disorder or syndrome in a subject in need thereof comprising administering to the subject a therapeutically effective amount of a compound of the invention. The invention further provides a method, wherein the HIV mediated disease, disorder or syndrome is like AIDS, AIDS related complex, or a syndrome characterized by symptoms such as persistent generalized lymphadenopathy, fever and weight loss, or an retroviral infection genetically related to AIDS.

Anti HIV inhibitory potential of the compounds of present invention may be demonstrated by any one or more methodologies known in the art, such as by using the assays described in Mossman T, December 1983, *Journal of immunological methods*, 65 (1-2), 55-63 and *SPC Cole, cancer chemotherapy and Pharmacology*, 1986, 17, 259-263.

DETAILED DESCRIPTION OF THE INVENTION

The present invention provides C-3 novel triterpenone with C-28 amide derivatives and related compounds, which may be used as antiviral particularly as anti-HIV compounds and processes for the synthesis of these compounds. Pharmaceutically acceptable salts, pharmaceutically acceptable solvates, enantiomers, diastereomers of the derivatives, together with pharmaceutically acceptable carriers, excipients or diluents, which can be used for the treatment of diseases, condition and/or disorders mediated by viral infections, are also provided.

The Following Definitions Apply to the Terms as Used Herein

The terms "halogen" or "halo" includes fluorine, chlorine, bromine, or iodine.

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkoxylalkoxy" refers to a straight or branched hydrocarbon chain with oxygen radical consisting carbon atom, hydrogen atom and alkoxy groups, containing saturation or unsaturation, having from one to eight carbon atoms, and which is attached through oxygen atom to the rest of the molecule by a single bond, e.g., 2-(methyloxy) ethyloxy, 2-(ethyloxy)ethyloxy, 2-(n-propyloxy)ethyloxy, and 3-(isopropyloxy)butyloxy.

The term "amine" refers to an organic compounds and functional groups that contain a basic nitrogen atom with a lone pair. Amines are derivatives of ammonia, wherein one or more hydrogen atoms have been replaced by a substituent such as an alkyl or aryl group these may respectively be called alkylamines and arylamines; amines in which both types of substituent are attached to one nitrogen atom may be called alkylarylamines. Important amines include amino acids, trimethylamine, and aniline.

The term "amino acid" refers to a straight or branched hydrocarbon chain containing an amine group, a carboxylic acid group, and a side-chain that is specific to each amino acid and which is attached through the nitrogen atom of the amine group to the rest of the molecule by a single bond, e.g., alanine, valine, isoleucine, leucine, phenylalanine, or tyrosine.

The term "aminoalkyl" refers to any amino derivative of an alkyl radical more specifically dimethylamino ethyl.

The term "cycloalkyl" denotes a non-aromatic mono or multicyclic ring system of from 3 to about 12 carbon atoms, such as cyclopropyl, cyclobutyl, cyclopentyl, and cyclohexyl. Examples of multicyclic cycloalkyl groups include, but are not limited to, perhydronapththyl, adamantyl and norbornyl groups, bridged cyclic groups and spirobicyclic groups, e.g., spiro (4,4) non-2-yl.

The term "aryl" refers to an aromatic radical having from 6 to 14 carbon atoms such as phenyl, naphthyl, tetrahydronapthyl, indanyl, and biphenyl.

The terms "heterocyclyl" and "heterocyclic ring" refer to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, tetrazoyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl. The heterocyclic ring radical may be attached to the main structure at any heteroatom or carbon atom that results in the creation of a stable structure.

The term "heteroaryl" refers to an aromatic heterocyclic ring radical. The heteroaryl ring radical may be attached to the main structure at any heteroatom or carbon atom that results in the creation of a stable structure.

"Substituted" refers to 1-3 substituents on the same position or on different positions with the same groups or different groups. Unless otherwise specified, the term "substituted" as used herein refers to substitution with any one or any combination of the following substituents: hydroxy, halogen, carboxyl, cyano, nitro, oxo ($=$O), thio ($=$S), substituted or unsubstituted alkyl, substituted or unsubstituted aryl, substituted or unsubstituted cycloalkyl, substituted or unsubstituted amino, substituted or unsubstituted aryl, substituted or unsubstituted heteroaryl, substituted or unsubstituted heterocyclyl, substituted or unsubstituted guanidine.

The term "prodrug" denotes a derivative of a compound, which derivative, when administered to warm-blooded animals, e.g. humans, is converted into the compound (drug). The enzymatic and/or chemical hydrolytic cleavage of the compounds of the present invention occurs in such a manner that the proven drug form (parent carboxylic acid drug) is released, and the moiety or moieties split off remain nontoxic or are metabolized so that nontoxic metabolic products are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "treating" or "treatment" of a state, disease, disorder or condition includes:

(1) preventing or delaying the appearance of clinical symptoms of the state, disease, disorder or condition developing in a subject that may be afflicted with or predisposed to the state, disease, disorder or condition but does not yet experience or display clinical or subclinical symptoms of the state, disease, disorder or condition;

(2) inhibiting the state, disease, disorder or condition, i.e., arresting or reducing the development of the state, disease, disorder or condition or at least one clinical or subclinical symptom thereof; or (3) relieving the state, disease, disorder or condition, i.e., causing regression of the state, disease, disorder or condition or at least one of its clinical or subclinical symptoms.

The benefit to a subject receiving treatment is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disease, disorder or condition, is sufficient to effect such treatment. The "therapeutically effective amount" will vary depending on the compound, the state, disease, disorder or condition and its severity and the age, weight, physical condition and responsiveness of the subject receiving treatment.

The compounds of the present invention may form salts. Non-limiting examples of pharmaceutically acceptable salts forming part of this invention include salts derived from inorganic bases salts of organic bases salts of chiral bases, salts of natural amino acids and salts of non-natural amino acids. Certain compounds of the present invention are capable of existing in stereo isomeric forms (e.g., diastereomers, enantiomers, racemates, and combinations thereof). With respect to the overall compounds described by the Formula (1), the present invention extends to these stereo isomeric forms and to mixtures thereof. To the extent prior art teaches synthesis or separation of particular stereoisomers, the different stereo isomeric forms of the present invention may be separated from one another by the methods known in the art, or a given isomer may be obtained by stereospecific or asymmetric synthesis. Tautomeric forms and mixtures of compounds described herein are also contemplated.

Pharmaceutically acceptable solvates includes hydrates and other solvents of crystallization (such as alcohols). The compounds of the present invention may form solvates with low molecular weight solvents by methods known in the art.

Pharmaceutical Compositions

The pharmaceutical compositions provided in the present invention include at least one compound described herein and at least one pharmaceutically acceptable excipient (such as a pharmaceutically acceptable carrier or diluent). Specifically, the contemplated pharmaceutical compositions include a compound(s) described herein in an amount sufficient to treat viral infection in a subject.

The subjects contemplated include, for example, a living cell and a mammal, including human. The compound of the present invention may be associated with a pharmaceutically acceptable excipient (such as a carrier or a diluent) or be diluted by a carrier, or enclosed within a carrier which can be in the form of a capsule, sachet, or other container.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters, and polyoxyethylene.

The carrier or diluent may include a sustained release material, such as, for example, glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick-, sustained-, or delayed-release of the active ingredient after administration to the subject by employing procedures known in the art.

The pharmaceutical compositions described herein may be prepared, e.g., as described in *Remington: The Science and Practice of Pharmacy*, 20$^{th}$ Ed., 2003 (Lippincott Williams & Wilkins). For example, the active compound can be mixed with a carrier, or diluted by a carrier, or enclosed within a carrier, which may be in the form of an ampule, capsule, or sachet. When the carrier serves as a diluent, it may be a solid, semi-solid, or liquid material that acts as a vehicle, excipient, or medium for the active compound.

The pharmaceutical compositions may be in conventional forms, for example, capsules, tablets, solutions, suspensions, injectables or products for topical application. Further, the pharmaceutical composition of the present invention may be formulated so as to provide desired release profile.

The route of administration may be any route which effectively transports the active compound to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is specifically suitable.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Exemplary carriers for tablets, dragees, or capsules include lactose, cornstarch, and/or potato starch. A syrup or elixir can be used in cases where a sweetened vehicle can be employed.

A typical tablet that may be prepared by conventional tableting techniques.

Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, specifically aqueous solutions with the active compound dissolved in polyhydroxylated castor oil.

Methods of Screening

Antiviral HIV activity and cytotoxicity of compounds present invention can be measured in parallel by following the methods published in the literature.

The cytotoxic effect of compounds can be analyzed by measuring the proliferation of cells using the 3-(4,5-Dimethylthiazol-2-yl)-2,5-diphenyl tetrazlium bromide (MTT) staining. Cells ($5 \times 10^3$ cells/well) will be incubated in 96 well plates in the presence or absence of compounds. At the end of treatment, 20 µl of MTT (5 mg/ml in PBS) will be added to each well and incubated for an additional 4 hours at 37° C. The purple-blue MTT formazan precipitate will be dissolved in a triplex reagent containing 10% SDS, 5% isobutanol and 10 mmol/lit HCl. The activity of mitochondria, reflecting cellular growth and viability, will be evaluated by measuring the optical density at 570 nm on micro titer plate.

Action of compounds on replication of HIV in Sup-T1 cells can be determined by the method published by Roda Rani et al., 2006 (Archives of Biochemistry and Biophysics, Volume 456, Issue 1, 1 Dec. 2006, Pages 79-92).

Briefly, $1 \times 10^6$ Sup-T1 cells with 100% cell viability will be seeded in RPMI 1640, 0.1% FBS four 12 well plates. Increasing concentrations of Epap-1 peptides will be added to the cells and will be infected with $HIV_{93\ IN\ 101}$ each at final concentration of virus equivalent to 2 ng of p24 per ml. The infected cells will be incubated at 37° C. and 5% $CO_2$ incubator for 2 hours. After 2 hours the cells will be pelleted at 350 g for 10 minutes, supernatant will be discarded and cell will be held with RPMI 1640 containing 10% FBS. The cells will be resuspended in the same medium with increasing concentrations of Epap-1 peptides and will be incubated for 96 hours. The cells will be supplemented with peptides at every 24 hours. The supernatants will be collected after 96 hours and analyzed using P24 antigen capture assay kit (SAIC Fredrick). The infection in the absence of Epap-1 will be considered to be 0% inhibition Azidothymidine (AZT) will be taken as positive control.

Action of compound on virus entry and quantification of virus entered can be done in terms of GFP expression by the following the methods published J. Virol. 72, 6988 (1998) by in Cecilia et al., and Analytical Biochemistry Volume 360, Issue 2, 15 Jan. 2007, Pages 315-317 (Dyavar S. Ravi and Debashis Mitra).

Briefly, cells will be seeded in to wells of 24 well plates 1 day prior to the experiment. The cells will be transfected with Tat-reporter. The virus inoculum will be adjusted to 1,000-4,000 TCID 50/ml in assay medium (DMEM, 10% FCS, glutamine and antibiotics), 50 µl aliquots will be incubated with serial dilutions of compounds (50 µl) for 1 hour at 37° C. The reporter expression will be quantified at appropriate time calculated inhibitory doses referrers to the concentration of these agents in this preincubation mixture.

Other relevant references useful for screening antiviral HIV activity are: Averett, D. R. 1989. Anti-HIV compound assessment by two novel high capacity assays. J. Virol. Methods 23: 263-276; Schwartz, O., et al. 1998; A rapid and simple colorimeric test fror the study of anti HIV agents. AIDS Res. and Human Retroviruses, 4(6):441-447; Daluge, S. M., et al. 1994. 5-Chloro-2',3'-deoxy-3'fluorouridine (935U83), a selective anti human immunodeficiency virus agent with an improved metabolic and toxicological profile; Antimicro. Agents and Chemotherapy, 38(7):1590-1603; H. Mitsuya and S. Border, Inhibition of the in vitro infectivity and cytopathic effect of human T-lymphotropic virus type lymphadenopathy-associated virus (HLTV-III/LAV) by 2,3'-dideoxynucleosides, Proc. Natl. Acad. Sci. USA, 83, 1911-15(1986); Pennington et al., Peptides 1990; Meek T. D et al., Inhibition of HIV-1 protease in infected T-limphocytes by synthetic peptide analogues, Nature, 343, p90 (1990); Weislow et al., J. Natl. Cancer Inst. 81, 577-586, 1989; T. Mimoto et al., J. Med. Chem., 42, 1789-1802, 1999; Uckun et al 1998, Antimicrobial Agents and Chemotherapy 42:383; for P24 antigen assay Erice et al., 1993, Antimicrob. Ag. Chemotherapy 37: 385-383; Koyanagi et al., Int. J. Cancer, 36, 445-451, 1985; Balzarini et al. AIDS (1991), 5, 21-28; Connor et al., Journal of virology, 1996, 70, 5306-5311; Popik et al., Journal of virology, 2002, 76, 4709-4722; Harrigton et al., Journal of Virology Methods, 2000, 88, 111-115; Roos et al., Virology 2000, 273, 307-315; Fedyuk N. V. et al; Problems of Virology 1992, (3)P135; Mosmann T, December 1983, Journal of immunological methods, 65 (1-2), 55-63; SPC Cole, cancer chemotherapy and Pharmacology, 1986, 17, 259-263, Antiviral methods and protocols (Eds: D Kinchington and R. F. Schinazi) Humana Press Inc., 2000, HIV protocols (Eds: N. L. Michael and J. H. Kim) Humana Press Inc, 1999, DAIDS Virology manual from HIV laboratories, Publication NIH-97-3838, 1997, 4. HIV-1 p24 antigen capture assay, enzyme immunoassay for detection of Human immunodeficiency Virus Type 1 (HIV-1) p24 in tissue culture media—Advanced bio science laboratories, Inc kit procedure.

Methods of Treatment

The present invention provides compounds and pharmaceutical formulations thereof that are useful in the treatment of diseases, conditions and/or disorders mediated by viral infections. The connection between therapeutic effect and antiviral is illustrated. For example, PCT publication Nos. WO 01/07646, WO 01/65957, or WO 03/037908; US publication Nos. U.S. Pat. No. 4,598,095 or US 2002/0068757; EP publication Nos. EP 0989862 or EP 0724650; *Bioorganic & Medicinal Chemistry Letters*, 16, (6), 1712-1715, 2006; and references cited therein, all of which are incorporated herein by reference in their entirety and for the purpose stated.

The present invention further provides a method of treating a disease, condition and/or disorder mediated by viral infections in a subject in need thereof by administering to the subject a therapeutically effective amount of a compound or a pharmaceutical composition of the present invention.

Diseases, conditions, and/or disorders that are mediated by viral infections are believed to include, but are not limited to, HIV infection, HBV infection, HCV infection, a retroviral infection genetically related to HIV, AIDS, inflammatory disease, respiratory disorders (including adult respiratory distress syndrome (ARDS), bronchitis, chronic bronchitis, chronic obstructive pulmonary disease, cystic fibrosis, asthma, emphysema, rhinitis and chronic sinusitis), inflammatory bowel disease (including Crohn's disease and ulcerative colitis), multiple sclerosis, rheumatoid arthritis, graft rejection (in particular but not limited to kidney and lung allografts), endometriosis, type I diabetes, renal diseases, chronic pancreatitis, inflammatory lung conditions, chronic heart failure and bacterial infections (in particular but not limited to tuberculosis).

The compounds of the present invention can obtain more advantageous effects than additive effects in the prevention or treatment of the above diseases when using suitably in combination with the available drugs. Also, the administration dose can be decreased in comparison with administration of either drug alone, or adverse effects of co administrated drugs other than antiviral can be avoided or declined.

Methods of Preparation

The compounds described herein may be prepared by techniques known in the art. In addition, the compounds described herein may be prepared by following the reaction sequence as depicted in Schemes-1 to 2. Further, in the following schemes, where specific bases, acids, reagents, solvents, coupling agents, etc., are mentioned, it is understood that other bases, acids, reagents, solvents, coupling agents etc., known in the art may also be used and are therefore included within the present invention. Variations in reaction conditions, for example, temperature and/or duration of the reaction, which may be used as known in the art, are also within the scope of the present invention. All the stereoisomers of the compounds in these schemes, unless otherwise specified, are also encompassed within the scope of this invention.

Compounds of the present invention can be synthesized from naturally occurring Betulinic acid or betulinal. Key intermediates required for synthesizing analogues are either commercially available, or can be prepared by the methods published in the literature. For example, the key intermediates in the present invention were prepared by modifying the procedures published in *Journal of organic chemistry* 2010, 75, 1285-1288; *Journal of organic chemistry* 2000, 65, 3934-3940; *Tetrahedron: asymmetry* 2008, 19, 302-308; or *Tetrahedron: asymmetry* 2003, 14, 217-223.

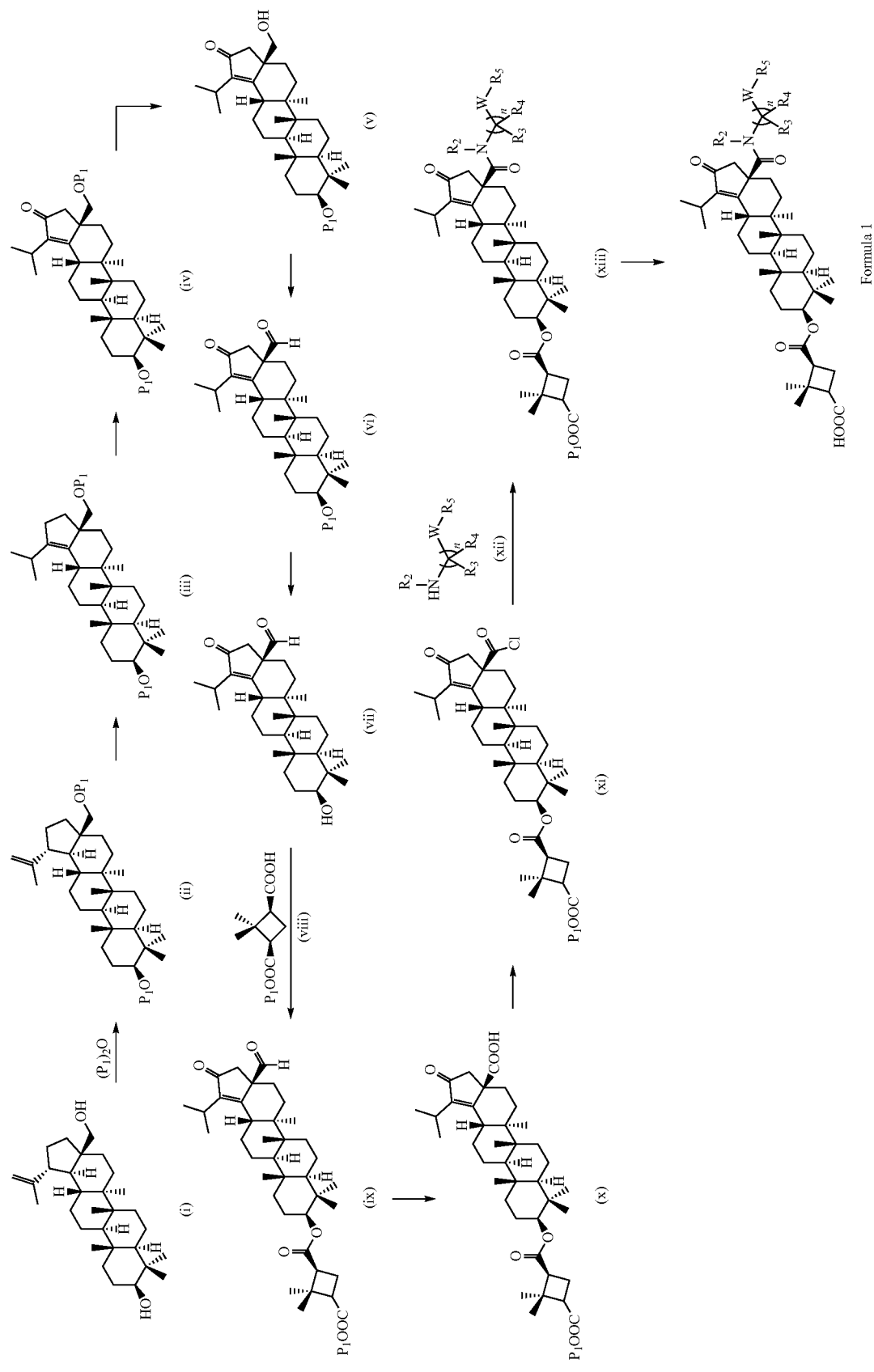

The compounds of formula 1 (wherein, $R_2$, $R_3$, $R_4$, $R_5$ and W are same as defined above) can be prepared as described in Scheme 1. The C-3 & C-28 di alcohol compounds of formula (i) can be protected in different ways like (a) With a suitable ester forming reagents such as anhydrides with or without addition of base or solvent or catalyst under heating conditions or (b) with a suitable ester forming reagents such as anhydrides, acid halides or mixed anhydrides or the like in the presence of bases such as triethylamine (TEA), N,N-diisopropylethylamine (DIPEA) or pyridine or the like in solvents such as dichloromethane (DCM), tetrahydrofuran (THF) or toluene or the like with or without addition of catalysts such as 4-(Dimethylamino)pyridine (DMAP) or the like to give the C-3 & C-28 di alcohol protected compounds of formula (ii) ($P_1$ and $P_2$ are protecting groups such as acetyl, benzyl or the like).

The terminal double bond of C-3 & C-28 di alcohol protected compounds of formula (ii) can be migrated to the ring-E compounds of formula (iii) in the presence of hydrogen bromide (HBr) in acetic acid (AcOH), acetic acid (AcOH) and acetic anhydride ($Ac_2O$) in solvents such as toluene, benzene or xylene or the like. The ring-E compounds of formula (iii) can be converted to the ring-E enone compounds of formula (iv) in the presence of sodium dichromate dihydrate ($Na_2Cr_2O_7.2H_2O$), sodium acetate (NaOAc), acetic acid (AcOH) and acetic anhydride ($Ac_2O$) in solvents such as toluene, benzene or the like. The ring-E enone compounds of formula (iv) can be selectively deprotected at C-28 to give the C-28 alcohol compounds of formula (v) in the presence of potassium hydroxide (KOH) or the like in the combination of solvents such as toluene:ethanol (EtOH) (1:1) or with reagent like Aluminum isopropoxide [$Al(OCH(CH_3)_2)_3$] in solvent such as 2-propanol or the like. The C-28 alcohol compounds of formula (v) can be converted to the C-28 aldehyde compounds of formula (vi) in the presence of pyridinium chlorochromate (PCC), pyridinium dichromate (PDC), Dess-Martin periodinane (DMP) or Swern oxidation conditions in solvents such as dichloromethane (DCM) or the like. The C-3 acetyl group of compounds of formula (vi) can be deprotected to the C-3 hydroxy compounds of formula (vii) with reagents like zirconium tetrachloride ($ZrCl_4$) in combination of solvents such as methanol (MeOH):dichloromethane (DCM) (2.5:1) or the like. The C-3 hydroxy compounds of formula (vii) can be reacted with the acid compounds of formula (viii) to give the C-3 protected ester compounds of formula (ix) in different ways like (a) Acid (viii) and alcohol (vii) coupling in the presence of Yamaguchi reagent like 2,4,6-trichlorobenzoyl chloride or the like in the presence of bases such as triethylamine (TEA) or N,N-diisopropylethylamine (DIPEA) and catalyst such as 4-(Dimethylamino)pyridine (DMAP) in solvents such as dichloromethane (DCM) or tetrahydrofuran (THF) or toluene or the like.

(b) Acid (viii) and alcohol (vii) coupling in the presence of coupling reagents such as 1-Ethyl-3-(3-dimethylaminopropyl)carbodiimide (EDCI) or N,N'-dicyclohexylcarbodiimide (DCC) or the like in the presence of bases such as triethylamine (TEA) or N,N-diisopropylethylamine (DIPEA) and catalyst such as 4-(Dimethylamino)pyridine (DMAP) in solvents such as dichloromethane (DCM), N,N-dimethylformamide (DMF) or tetrahydrofuran (THF) or the like.

The C-28 aldehyde compounds of formula (ix) can be converted to the C-28 acid compounds of formula (x) in the presence of oxidising agents such as sodium chlorite ($NaClO_2$) or the like in the presence of scavenger such as 2-methyl-2-butene or the like in the presence of a buffer such as sodium dihydrogen phosphate ($NaH_2PO_4$) or the like in the combination of solvents such as tert-butanol (t-BuOH), tetrahydrofuran (THF) and water ($H_2O$) or the like. The C-28 acid compounds of formula (x) can be converted to the C-28 acid chloride compounds of formula (xi) in the presence of reagents such as thionyl chloride ($SOCl_2$) or oxalyl chloride (($COCl)_2$) or the like in solvents such as dichloromethane (DCM), chloroform ($CHCl_3$) or the like. The C-28 acid chloride compounds of formula (xi) can be coupled with the amine or amine hydrochloride compounds of formula (xii) in the presence of bases such as triethylamine (TEA), N,N-diisopropylethylamine (DIPEA) or the like in solvents such as dichloromethane (DCM) or tetrahydrofuran (THF) or the like to give the C-28 amide compounds of formula (xiii). The ester group in compounds of formula (xiii) can be deprotected to the corresponding acid compounds of formula 1 in different ways like (a) ester deprotection in the presence of catalyst such as palladium on carbon (10% Pd/C) and hydrogen source such as ammonium formate ($HCOONH_4$) or hydrogen gas ($H_2$) or the like in solvents such as tetrahydrofuran (THF), ethyl acetate (EtOAc) or methanol (MeOH) or the combination of ethyl acetate (EtOAc):methanol (MeOH) (1:1) or the like.

(b) ester group can be hydrolysed in the presence of aqueous solution of inorganic bases such as potassium carbonate ($K_2CO_3$), sodium hydroxide (NaOH), potassium hydroxide (KOH) or the like in solvents such as methanol (MeOH) and Tetrahydrofuran (THF) or the like.

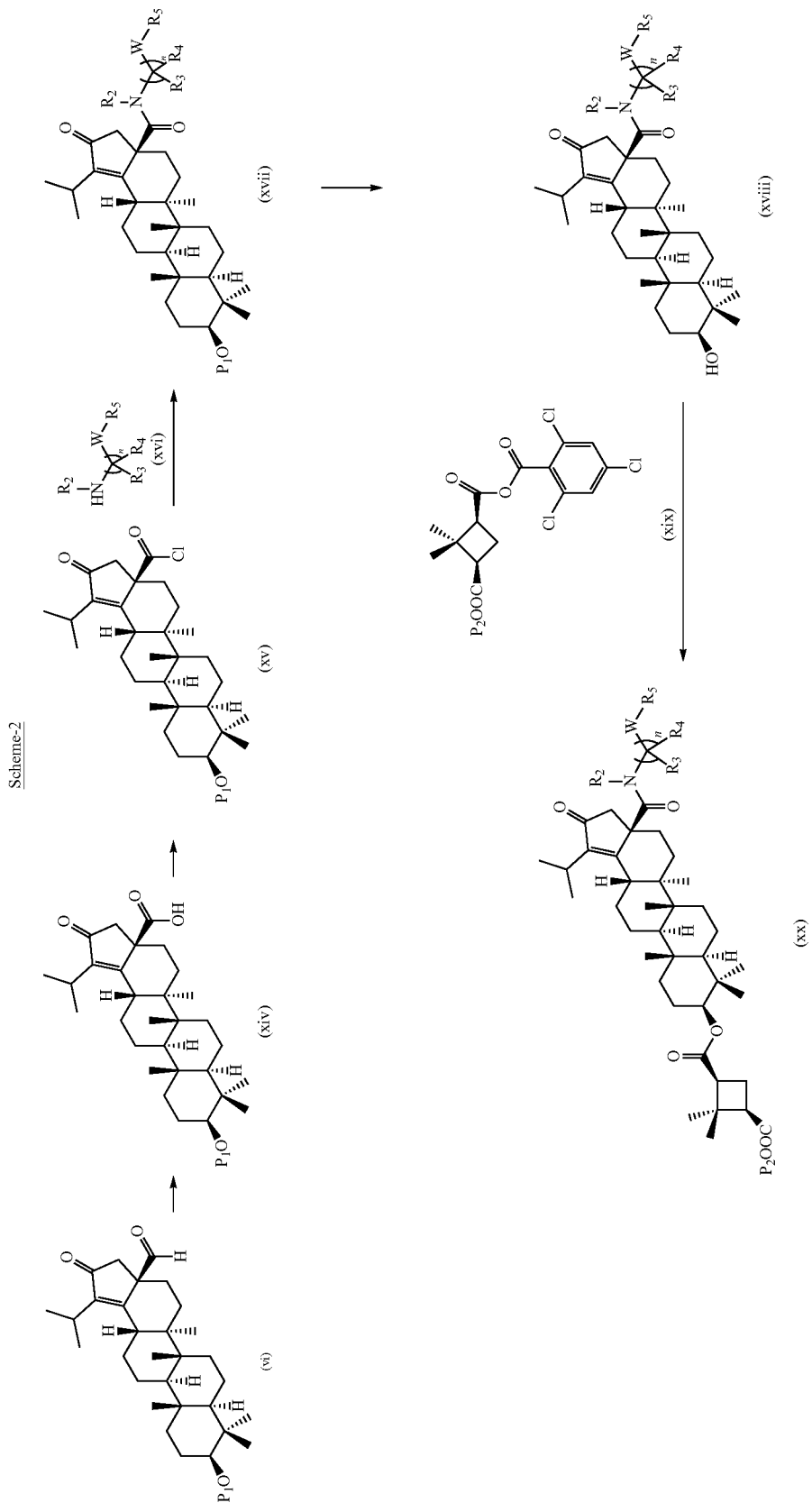
Scheme-2

-continued
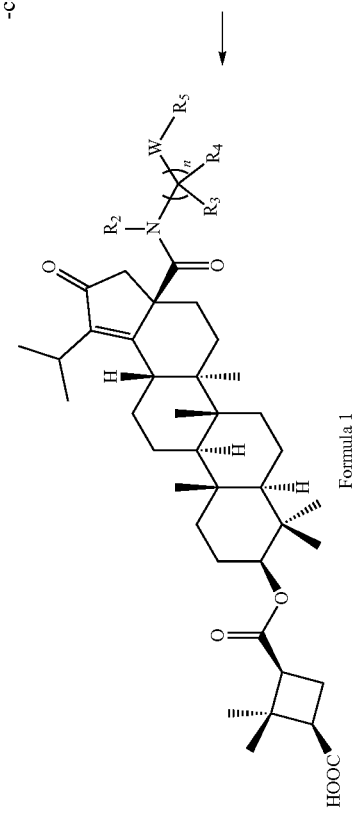
Formula 1

The compounds of formula 1 (wherein, $R_2$, $R_3$, $R_4$, $R_5$ and W are same as defined above) can be prepared as described in Scheme 2. The C-28 aldehyde compounds of formula (vi) can be converted to the C-28 acid compounds of formula (xiv) in the presence of oxidising agents such as sodium chlorite ($NaClO_2$) or the like in the presence of scavenger such as 2-methyl-2-butene or the like in the presence of a buffer reagent such as sodium dihydrogen phosphate ($NaH_2PO_4$) or the like in the combination of solvents such as tert-butanol (t-BuOH), tetrahydrofuran (THF) and water ($H_2O$) or the like. The C-28 acid compounds of formula (xiv) can be converted to the C-28 acid chloride compounds of formula (xv) in the presence of reagents such as thionyl chloride ($SOCl_2$), oxalyl chloride (($COCl)_2$) or the like in solvents such as dichloromethane (DCM), chloroform ($CHCl_3$) or the like. The C-28 acid chloride compounds of formula (xv) can be coupled with the amine or amine hydrochloride compounds of formula (xvi) in the presence of bases such as triethylamine (TEA) or N,N-diisopropylethylamine (DIPEA) or the like in the solvents such as dichloromethane (DCM), or tetrahydrofuran (THF) or the like to give the C-3 acetyl & C-28 amide compounds of formula (xvii). The C-3 acetyl group of compounds of formula (xvii) can be converted to the corresponding C-3 hydroxy compounds of formula (xviii) in the presence of inorganic bases such as sodium hydroxide (NaOH) or potassium hydroxide (KOH) or the like in combination of solvents such as methanol (MeOH), tetrahydrofuran (THF) and water ($H_2O$) or in acidic conditions like HCl in solvents such as 1,4-dioxane or methanol (MeOH) or the like. The C-3 hydroxy compounds of formula (xviii) can be converted to the C-3 ester compounds of formula (xx) by using the anhydride compounds of formula (xix) or the acid compounds of formula (viii) in different ways like (a) Anhydride (xix) and alcohol (xviii) coupling in the presence of catalyst such as 4-(Dimethylamino)pyridine (DMAP) in solvents such as toluene or benzene or the like.

(b) Acid (viii) and alcohol (xviii) coupling in the presence of coupling reagents such as 1-Ethyl-3-(3-dimethylaminopropyl)carbodiimide (EDCI) or N,N'-dicyclohexylcarbodiimide (DCC) or the like with catalyst such as 4-(Dimethylamino)pyridine (DMAP) in solvents such as dichloromethane (DCM) or tetrahydrofuran (THF) or the like. The ester group in compounds of formula (xx) can be deprotected to the acid compounds of formula 1 in different ways like (a) Ester deprotection in the presence of catalyst such as palladium on carbon (10% Pd/C) and hydrogen source such as ammonium formate ($HCOONH_4$) or hydrogen gas ($H_2$) or the like in solvents such as tetrahydrofuran (THF), ethyl acetate (EtOAc) or methanol (MeOH) or the combination of ethyl acetate (EtOAc):methanol (MeOH) (1:1) or the like.

(b) Ester group can be hydrolysed in the presence of aqueous solution of inorganic bases such as sodium hydroxide (NaOH), potassium hydroxide (KOH) or the like in combination of solvents such as methanol (MeOH) and Tetrahydrofuran (THF) or the like.

The abbreviations used in the entire specification may be summarized herein below with their particular meaning: DIPEA (N,N-Diisopropylethylamine); ° C. (degree Celsius); δ (delta); ppm (parts per million); % (percentage); DMSO-$d_6$ (Deuterated DMSO); d (Doublet); g or gr (gram); H or $H_2$ (Hydrogen); HCl (Hydrochloric acid); h or hr. (Hours); Hz (Hertz); HPLC (High-performance liquid chromatography); mmol (Milli mol); M (Molar); ml (Milliliter); mg (Milli gram); m (Multiplet); mm (Millimeter); MHz (Megahertz); ESI-MS (Electron spray Ionization Mass spectra); min (Minutes); mM (Milli molar); NaOH (Sodium hydroxide); $N_2$ (Nitrogen); NMR (Nuclear magnetic resonance spectroscopy); S (Singlet); TEA (Triethyl amine); TLC (Thin Layer Chromatography); THF (Tetrahydrofuran); t (Triplet); IC (Inhibitory concentration), nM (Nano molar); pH (Pouvoir hydrogen); $(Boc)_2O$ (Di-tert-butyl dicarbonate); DCM (dichloromethane); eq (equivalent); Ltr or L (Liter); $CDCl_3$ (Deuterated chloroform); J (Coupling constant); $J_{AB}$ (Coupling constant); ABq (AB quartet); RB flask (Round Bottomed flask).

EXPERIMENTAL

The present invention is further illustrated by the following examples, which are not to be construed in any way as imposing limitations upon the scope of this disclosure, but rather are intended to be illustrative only. On the contrary, it is to be clearly understood that resort may be had to various other embodiments, modifications, and equivalents thereof which, after reading the description herein, may suggest themselves to one of ordinary skill in the art without departing from the spirit of the present invention. Thus, the skilled artisan will appreciate how the experiments and examples may be further implemented as disclosed by variously altering the following examples, substituents, reagents, or conditions.

INTERMEDIATES

Intermediate 1: Preparation of 2-(5-phenyl-1H-imidazol-2-yl)propan-2-amine

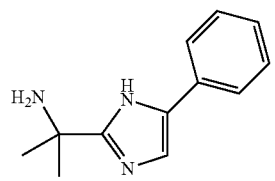

Step 1: Synthesis of 2-oxo-2-phenylethyl 2-((tert-butoxycarbonyl)amino)-2-methyl propanoate

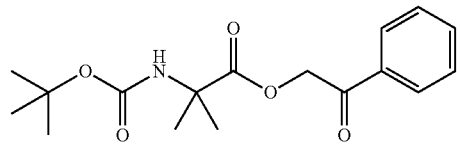 [SMILES: CC(C)(C)OC(=O)NC(C)(C)C(=O)OCC(=O)c1ccccc1]

To a stirred solution of 2-((tert-butoxycarbonyl)amino)-2-methylpropanoic acid (5.0 g, 24.87 mmol, 1.0 eq) in DCM (75 ml) under nitrogen atmosphere was added 2-bromo-1-phenylethan-1-one (5.94 g, 29.85 mmol, 1.2 eq) and DIPEA (12.76 ml, 74.62 mmol, 3.0 eq). The reaction mixture was stirred at room temperature for overnight. TLC indicated starting material was consumed and the desired product was observed. The reaction mixture was diluted with water (100 ml) and extracted with DCM (3×100 ml). The combined organic extracts were washed with 0.5N HCl (50 ml), water (50 ml) and brine solution (50 ml). The organic layer was dried over $Na_2SO_4$, filtered and evaporated under reduced pressure. The residue was purified by silicagel column chromatography by using 0-2% methanol in dichloromethane gradient. The fractions containing the expected product were combined and concentrated under reduced pressure to obtain the desired product (6.0 g, yield: 75.9%) as a yellow solid. 1H NMR (300 MHz, CDCl₃): δ ppm 7.90 (d, J=7.5 Hz, 2H), 7.62-7.57 (m, 1H), 7.52-7.44 (m, 2H), 5.38 (s, 2H), 5.08 (brs, 1H), 1.61 (s, 6H), 1.44 (s, 9H); ESI-MS: m/z 344.03 (M+Na)⁺.

Step 2: Synthesis of tert-butyl (2-(5-phenyl-1H-imidazol-2-yl)propan-2-yl)carbamate

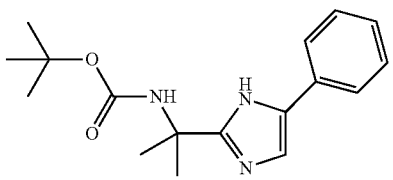 [SMILES: CC(C)(C)OC(=O)NC(C)(C)c1ncc(-c2ccccc2)[nH]1]

To a stirred solution of 2-oxo-2-phenylethyl 2-((tert-butoxycarbonyl)amino)-2-methyl propanoate (step 1, 6.0 g, 18.67 mmol, 1.0 eq) in toluene (120 ml) was added ammonium acetate (21.58 g, 280.05 mmol, 15.0 eq). The reaction mixture was refluxed for overnight. TLC indicated starting material was consumed and the desired product was observed. The reaction mixture was evaporated under reduced pressure, diluted with water (100 ml) and extracted with DCM (3×100 ml). The combined organic extracts were washed with water (50 ml), dried over sodium sulfate, filtered and evaporated under reduced pressure. The residue was purified by silicagel column chromatography by using 0-4% methanol in dichloromethane gradient. The fractions containing the expected product were combined and concentrated under reduced pressure to obtain the desired product (5.0 g, yield: 88.87%) as a yellow solid; ESI-MS: m/z 302.10 (M+H)⁺.

Step 3: Synthesis of 2-(5-phenyl-1H-imidazol-2-yl)propan-2-amine

To a stirred solution of tert-butyl (2-(5-phenyl-H-imidazol-2-yl)propan-2-yl)carbamate (step 2, 5.0 g, 16.58 mmol, 1.0 eq) in DCM (40 ml) at 0° C. was added trifluoroacetic acid (10 ml). The reaction mixture was allowed to stir at room temperature for overnight. TLC indicated starting material was consumed and the desired product was observed. The reaction mixture was evaporated under reduced pressure, diluted with water (50 ml), cooled to 0° C., pH adjusted to 8.0 with saturated sodium bicarbonate solution and extracted with DCM (3×100 ml). The combined organic extracts were washed with water (50 ml), dried over Na₂SO₄, filtered and evaporated under reduced pressure to obtain the desired product (2.0 g, yield: 60%) as a solid. 1H NMR (300 MHz, CDCl₃): δ ppm 7.65 (d, J=7.5 Hz, 2H), 7.40-7.32 (m, 2H), 7.24-7.18 (m, 2H), 1.59 (s, 6H); ESI-MS: m/z 219.20 (M+NH₄)⁺.

Intermediate 2: Preparation of (S)-1-(pyrrolidin-2-ylmethyl)pyrrolidine

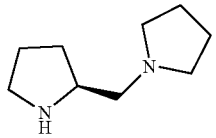 [SMILES: C1CN[C@H](CN2CCCC2)C1]

Step 1: Synthesis of tert-butyl (S)-2-((tosyloxy)methyl)pyrrolidine-1-carboxylate

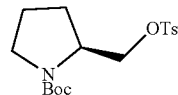 [SMILES: Cc1ccc(S(=O)(=O)OC[C@@H]2CCCN2C(=O)OC(C)(C)C)cc1]

To a stirred solution of tert-butyl (S)-2-(hydroxymethyl) pyrrolidine-1-carboxylate (7.0 g, 34.82 mmol, 1.0 eq) in DCM (70 ml) was added triethylamine (19.4 ml, 139.30 mmol, 4.0 eq), DMAP (0.010 g) and para-toluenesulphonylchloride (7.9 g, 41.79 mmol, 1.2 eq). The reaction mixture was stirred at room temperature for overnight. TLC indicated starting material was consumed and the desired product was observed. The reaction mixture was diluted with DCM (200 ml) washed with water (2×100 ml). The organic layer was dried over Na₂SO₄, filtered and evaporated under reduced pressure. The residue was purified by silicagel column chromatography to obtain the titled compound (7.0 g, yield: 56.6%) as a colorless liquid. 1H NMR (300 MHz, DMSO-d6): δ ppm 7.78 (d, J=8.1 Hz, 2H), 7.49 (d, J=8.1 Hz, 2H), 4.06-3.97 (m, 2H), 3.82 (m, 1H), 3.25-3.15 (m, 2H), 2.42 (s, 3H), 2.0-1.82 (m, 1H), 1.79-1.65 (m, 3H), 1.28 (s, 9H); ESI-MS: m/z 378.15 (M+Na)⁺.

Step 2: Synthesis of tert-butyl (S)-2-(pyrrolidin-1-ylmethyl)pyrrolidine-1-carboxylate

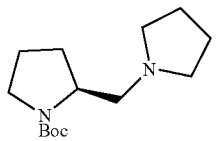 [SMILES: CC(C)(C)OC(=O)N1CCC[C@H]1CN1CCCC1]

To a stirred solution of tert-butyl (S)-2-((tosyloxy)methyl) pyrrolidine-1-carboxylate (step 1, 7.0 g, 19.71 mmol, 1.0 eq) in acetonitrile (70 ml) was added pyrrolidine (2.8 g, 39.43 mmol, 2.0 eq) and potassium carbonate (10.8 g, 78.89 mmol, 4.0 eq). The reaction mixture was refluxed for overnight. TLC indicated starting material was consumed and the desired product was observed. The reaction mixture was evaporated under reduced pressure, diluted with DCM (250 ml) and washed with water (2×150 ml). The organic layer was dried over Na₂SO₄, filtered and evaporated under reduced pressure. The residue was purified by silicagel column chromatography by using 4% methanol in dichloromethane as an eluent to obtain the titled compound (5.0 g, 99.8% yield) as a colorless liquid. 1H NMR (300 MHz, DMSO-d6): δ ppm 3.57 (m, 1H), 3.27-3.10 (m, 3H), 2.44-2.30 (m, 5H), 1.84-1.63 (m, 8H), 1.39 (s, 9H).

Step 3: Synthesis of (S)-1-(pyrrolidin-2-ylmethyl)pyrrolidine

To a stirred solution of tert-butyl (S)-2-(pyrrolidin-1-ylmethyl)pyrrolidine-1-carboxylate (step 2, 5.0 g, 19.68 mmol, 1.0 eq) in DCM (40 ml) was added trifluoroacetic acid (10 ml). The reaction mixture was stirred at room temperature for overnight. After completion of the reaction monitored by TLC, the reaction mixture was diluted with DCM (100 ml), washed with saturated sodium bicarbonate solution (100 ml) and saturated brine solution (100 ml). The organic layer was evaporated under reduced pressure to obtain the titled compound (crude wt: 2.8 g) as a colourless liquid. ESI-MS: m/z 155.09 (M+H)+.

Intermediate 3: Preparation of 2-methyl-1-(pyrrolidin-1-yl)propan-2-amine

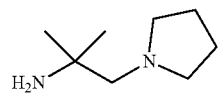

Step 1: Synthesis of 1-(2-methyl-2-nitropropyl)pyrrolidine

To a stirred solution of pyrrolidine (5.0 g, 70.42 mmol, 1.0 eq) and 2-nitropropane (6.33 ml, 70.42 mmol, 1.0 eq) at 10° C. dropwise slowly added formaldehyde (5.85 ml, 3.0 eq, 37%) and aqueous NaOH solution (3.0 mL, 0.5 N). The reaction mixture was stirred at 25° C. for about 1 hour and then at 50° C. for about 1 hour. The solution was diluted with water and extracted with diethyl ether. The combined organic extracts were dried over Na$_2$SO$_4$, filtered and combined with HCl in dioxane (30 mL). The precipitates formed were collected by filtration and dried in vacuo gave the desired product (10.5 g, yield: 86.7%) as a semisolid. $^1$H NMR (CD$_3$OD, 300 MHz): δ ppm 3.16 (s, 2H), 2.67 (m, 4H), 1.37 (m, 4H), 1.21 (s, 6H); ESI-MS: m/z 173.09 (M+H)+.

Step 2: Synthesis of 2-methyl-1-(pyrrolidin-1-yl)propan-2-amine

To a stirred solution of 1-(2-methyl-2-nitropropyl)pyrrolidine (step 1, 10.5 g, 60.96 mmol, 1.0 eq) in Methanol (170 ml) was added Raney Nickel (3.9 g). The reaction mixture was hydrogenated at room temperature under 50 psi pressure for about 1 hour. After completion of the reaction (monitored by TLC), the reaction mixture was filtered through celite and the filtrate was concentrated in vacuo gave the desired product (7.5 g, yield: 87%) as a semisolid. 1H NMR (CD$_3$OD, 300 MHz): δ ppm 7.86 (s, 2H), 3.16 (s, 2H), 2.67 (m, 4H), 1.37 (m, 4H), 1.21 (s, 6H); ESI-MS: m/z 143.06 (M+H)+.

Intermediate 4: Preparation of (R)-1,3'-bipyrrolidine dihydrochloride

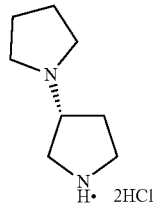

Step 1: Synthesis of tert-butyl (S)-3-hydroxypyrrolidine-1-carboxylate

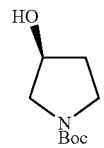

To a stirred solution of (S)-pyrrolidin-3-ol hydrochloride (3.0 g, 24.2 mmol) in DCM (30 ml), were added N(Et)$_3$ (10.2 ml, 72.8 mmol) and (Boc)$_2$O (6.4 g, 29.1 mmol) at 0° C. The reaction mixture was then warmed to room temperature and stirred for about 12 hours. After completion of the reaction (monitored by TLC), saturated NH$_4$Cl solution was added to the reaction mixture. The solution was extracted with DCM (2×100 mL) and the combined organic phases were washed with brine, dried over Na$_2$SO$_4$ and concentrated under reduced pressure to give the crude product. Purification by flash chromatography with EtOAc-hexane (2:8) as an eluent to afford the desired product (4.5 g, yield: 77.3%) as an oil. $^1$H NMR (300 MHz, DMSO-D$_6$): δ 4.87 (d, J=3.3 Hz, 1H), 4.20 (m, 1H), 3.28-3.24 (m, 3H), 3.11-3.07 (m, 1H), 1.86-1.79 (m, 1H), 1.75-1.70 (m, 1H), 1.39 (s, 9H).

Step 2: Synthesis of tert-butyl (S)-3-(tosyloxy)pyrrolidine-1-carboxylate

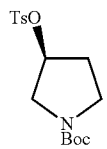

To a stirred solution of tert-butyl (S)-3-hydroxypyrrolidine-1-carboxylate (step 1, 3.48 g, 18.6 mmol) in DCM (40 ml) under N$_2$ atmosphere, were added N(Et)$_3$ (7.8 ml, 55.8 mmol), followed by TsCl (6 g, 31.6 mmol) and catalytic amount of DMAP at 0° C. The reaction mixture was allowed to room temperature and stirred for about 12 hours. After completion of the reaction (monitored by TLC), the reaction mixture was diluted with DCM. The organic layer was washed with saturated NH₄Cl solution, brine, dried over anhydrous sodium sulphate and concentrated under reduced pressure to get the residue. The crude product was purified via silica gel column chromatography with EtOAc and n-Hexane (1:9) as an eluent to afford the desired compound (5.6 g, yield: 88%) as a white solid. $^1$H NMR (300 MHz, DMSO-$d_6$): δ 7.78 (d, J=8.1 Hz, 2H), 7.36 (d, J=8.1 Hz, 2H), 5.04 (m, 1H), 3.44-3.39 (m, 4H), 2.45 (s, 3H), 2.22-1.92 (m, 2H), 1.43 (s, 9H); ES Mass: 364.17 [M+Na]$^+$.

Step 3: Synthesis of tert-butyl (R)-[1,3'-bipyrrolidine]-1'-carboxylate

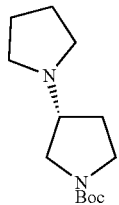 [SMILES: CC(C)(C)OC(=O)N1CC[C@@H](N2CCCC2)C1]

To a stirred solution of tert-butyl (S)-3-(tosyloxy)pyrrolidine-1-carboxylate (step 2, 3.0 g, 8.7 mmol) in ACN (30 ml) under N₂ atmosphere, were added Cs₂CO₃ (8.6 g, 26.3 mmol), followed by pyrrolidine (1.25 g, 17.6 mmol) at room temperature. The reaction mixture was heated to 100° C. and continued for about 12 hours. After completion of the reaction (monitored by TLC), the reaction mixture was cooled to room temperature and filtered through celite and the cake was washed with DCM (twice). The filtrate was washed with water, brine, dried over anhydrous sodium sulphate and concentrated under reduced pressure to give the residue. The crude product was purified via silica gel column chromatography with MeOH and DCM (2:98) to afford the desired compound (0.75 g, yield: 35.5%) as a thick oil. $^1$H NMR (300 MHz, DMSO-$d_6$): δ 3.43-3.29 (m, 2H), 3.23-3.10 (m, 1H), 3.03-2.95 (m, 1H), 2.72-2.57 (m, 1H), 2.47-2.40 (m, 4H), 1.96-1.92 (m, 1H), 1.79-1.65 (m, 5H), 1.38 (s, 9H); ES Mass: 241.17 [M+H]$^+$.

Step 4: Synthesis of (R)-1,3'-bipyrrolidine dihydrochloride

To a stirred solution of tert-butyl (R)-[1,3'-bipyrrolidine]-1'-carboxylate (step 3, 0.75 g, 3.1 mmol) in dioxane (5 ml), was added 6N HCl in dioxane (10 ml) and stirred for about 2 hours. After completion of the reaction (monitored by TLC), the reaction mixture was concentrated under reduced pressure to afford the desired product (0.66 g, yield: 100%). Next reaction was carried out without any further purification.

Intermediate 5: Preparation of (S)-2-(pyrrolidin-2-yl)propan-2-ol hydrochloride

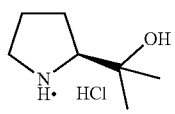

Step 1: Synthesis of tert-butyl (S)-2-(2-hydroxypropan-2-yl)pyrrolidine-1-carboxylate

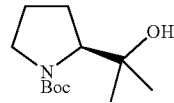 [SMILES: CC(C)(C)OC(=O)N1CCC[C@H]1C(C)(C)O]

To a stirred solution of Mg (3.14 g, 261.66 mmol) in Et₂O (40 ml), were added I₂ (cat) and iodomethane (9 ml, 130.8 mmol) and stirred for about 30 minutes. Then a solution of 1-(tert-butyl) 2-methyl (S)-pyrrolidine-1,2-dicarboxylate (6 g, 26.2 mmol) in THF (60 ml) was added and stirred for overnight. After completion of the reaction (monitored by TLC), the reaction mixture was quenched by cautious addition of saturated NH₄Cl solution at 0° C. and extracted with EtOAc (2×100 ml). The combined organic layers were washed with brine, dried over anhydrous sodium sulphate and concentrated under reduced pressure to get the residue. The crude product was purified via silica gel column chromatography with EtOAc and n-hexane (30:70) as an eluent to the afford desired compound (5.9 g, yield: 98.3%) as a thick oil. $^1$H NMR (300 MHz, DMSO-$d_6$): δ 4.84 (brs, 1H), 3.70-3.68 (m, 1H), 3.51-3.47 (m, 1H), 3.12 (m, 1H), 1.81-1.61 (m, 4H), 1.39 (s, 9H), 1.04 (s, 6H); ES Mass: 252.16 [M+Na]$^+$.

Step 2: Synthesis of (S)-2-(pyrrolidin-2-yl)propan-2-ol hydrochloride

To a stirred solution of tert-butyl (S)-2-(2-hydroxypropan-2-yl)pyrrolidine-1-carboxylate (step 1, 5.9 g, 25.7 mmol) in dioxane (50 ml), was added 6N HCl in dioxane (50 ml) and stirred for about 2 hours. After completion of the reaction (monitored by TLC), the reaction mixture was concentrated under reduced pressure to afford the desired product (4.2 g, yield: 100%). Next reaction was carried out without any further purification.

Intermediate 6: Preparation of (S)-2-((benzyloxy)methyl)-1-(((S)-pyrrolidin-2-yl)methyl)pyrrolidine hydrochloride

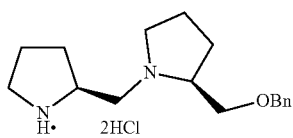

Step 1: Synthesis of tert-butyl (S)-2-((S)-2-(hydroxymethyl)pyrrolidine-1-carbonyl)pyrrolidine-1-carboxylate

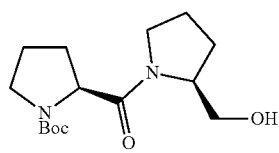 [SMILES: CC(C)(C)OC(=O)N1CCC[C@H]1C(=O)N1CCC[C@H]1CO]

To a stirred solution of (tert-butoxycarbonyl)-L-proline (7 g, 32.55 mmol) in DCM (70 ml) at 0° C., were added HOBt (5.27 g, 39.06 mmol), EDCI (7.46 g, 39.06 mmol) and DIPEA (8.4 ml, 48.83 mmol). After stirring about 20 minutes a solution of (S)-pyrrolidin-2-ylmethanol (3.58 g, 35.81 mmol) in DCM (25 ml) was added and allowed to stir at room temperature for about 12 hours. After completion of the reaction (monitored by TLC), the reaction mixture was diluted with DCM and washed with water, 1N HCl solution, saturated NaHCO$_3$ solution, brine and dried over Na$_2$SO$_4$ and concentrated under reduced pressure to give the crude product. Purification by column chromatography with EtOAc-hexane (7:3) as an eluent to afford the desired product (6.8 g, yield: 75.5%) as a thick oil. $^1$H NMR (300 MHz, DMSO-d$_6$): δ 4.74-4.68 (m, 1H), 4.38-4.29 (m, 2H), 3.94 (m, 1H), 3.54-3.16 (m, 4H), 1.99-1.69 (m, 8H), 1.31 (s, 9H).

Step 2: Synthesis of tert-butyl (S)-2-(((S)-2-(hydroxymethyl)pyrrolidin-1-yl)methyl)pyrrolidine-1-carboxylate

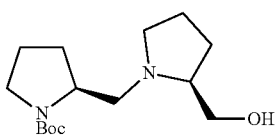 [SMILES: CC(C)(C)OC(=O)N1CCC[C@H]1CN1CCC[C@H]1CO]

To a stirred suspension of NaBH$_4$ (2.58 g, 68.45 mmol) in dry THF (20 ml) at 0° C., was added BF$_3$:Et$_2$O (7.1 ml, 57.04 mmol). After stirring about 30 minutes, was added a solution of tert-butyl (S)-2-((S)-2-(hydroxymethyl)pyrrolidine-1-carbonyl)pyrrolidine-1-carboxylate (step 1, 6.8 g, 22.81 mmol) in THF (60 ml) and allowed to stir at 60° C. for about 2 hours. After completion of the reaction (monitored by TLC), the reaction mixture was quenched by the cautious addition of MeOH (50 ml) at 0° C. and allowed to stir at 60° C. for about 12 hours. The reaction mixture was concentrated and the resulting residue was diluted with EtOAc and washed with water, brine and dried over Na$_2$SO$_4$ and concentrated under reduced pressure to give the crude product. Purification by column chromatography with MeOH:DCM (5:95) as an eluent to afford the desired product (3.6 g, yield: 55.6%) as a thick oil. $^1$H NMR (300 MHz, CDCl$_3$): δ 3.96-3.84 (m, 1H), 3.61-3.54 (m, 1H), 3.40-3.04 (m, 4H), 2.68-2.19 (m, 4H), 1.88-1.68 (m, 8H), 1.47 (s, 9H).

Step 3: Synthesis of tert-butyl (S)-2-(((S)-2-((benzyloxy)methyl)pyrrolidin-1-yl)methyl)pyrrolidine-1-carboxylate

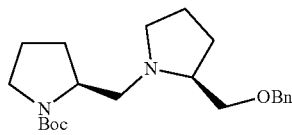 [SMILES: CC(C)(C)OC(=O)N1CCC[C@H]1CN1CCC[C@H]1COCc1ccccc1]

To a stirred solution of NaH (1.01 g, 25.35 mmol, 60% in mineral oil w/w) in THF (10 ml) under N$_2$ atmosphere at 0° C., was added tert-butyl (S)-2-(((S)-2-(hydroxymethyl)pyrrolidin-1-yl)methyl)pyrrolidine-1-carboxylate (step 2, 3.6 g, 12.67 mmol) in THF (40 ml). After 30 minutes benzyl bromide (2 ml, 16.47 mmol) was added and the reaction mixture was slowly allowed to attain to room temperature and stirred for overnight. After completion of the reaction (monitored by TLC), the reaction mixture was quenched by addition of saturated NH$_4$Cl solution at 0° C. The solution was extracted with EtOAc (2×100 mL) and the combined organic phases were washed with brine, dried over Na$_2$SO$_4$ and concentrated under reduced pressure to give the crude product. Purification by column chromatography with MeOH:DCM (3:97) as an eluent to afford the desired product (3 g, yield: 63.29%) as an oil. $^1$H NMR (300 MHz, CDCl$_3$): δ 7.37-7.29 (m, 5H), 4.51 (s, 2H), 3.91-3.78 (m, 1H), 3.45-3.19 (m, 5H), 2.66-2.59 (m, 2H), 2.46-2.37 (m, 1H), 2.28-2.18 (m, 1H), 1.96-1.55 (m, 8H), 1.46 (s, 9H).

Step 4: Synthesis of Synthesis of (S)-2-((benzyloxy)methyl)-1-(((S)-pyrrolidin-2-yl)methyl)pyrrolidine hydrochloride To a stirred solution of tert-butyl (S)-2-(((S)-2-((benzyloxy)methyl)pyrrolidin-1-yl)methyl)pyrrolidine-1-carboxylate (step 3, 1.5 g, 4.01 mmol) in dioxane (10 ml), was added 6N HCl in dioxane (20 ml) and stirred for about 2 hours. After completion of the reaction (monitored by TLC), the reaction mixture was concentrated under reduced pressure to afford the desired product (1.32 g, yield: 100%). Next reaction was carried out without any further purification.

Intermediate 7: Preparation of (S)-4-fluoro-1-(pyrrolidin-2-ylmethyl)piperidine dihydrochloride

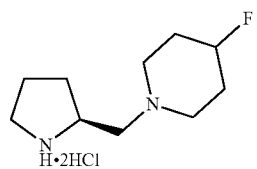

Step 1: Synthesis of tert-butyl (S)-2-((4-hydroxypiperidin-1-yl)methyl)pyrrolidine-1-carboxylate

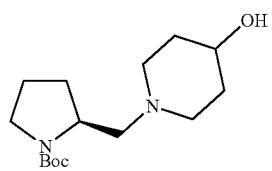 [SMILES: CC(C)(C)OC(=O)N1CCC[C@H]1CN1CCC(O)CC1]

To a stirred solution of tert-butyl (S)-2-((tosyloxy)methyl)pyrrolidine-1-carboxylate (Intermediate 2-step 1, 4.0 g, 10.95 mmol) in 1,4-dioxane (50 ml) under N$_2$ atmosphere, were added Cs$_2$CO$_3$ (10.7 g, 32.87 mmol), followed by piperidin-4-ol (1.1 g, 10.95 mmol) at room temperature. The reaction mixture was heated to 100° C. and continued for about 12 hours. After completion of the reaction (monitored by TLC), the reaction mixture was cooled to room temperature and filtered through celite and the cake was washed with DCM (twice). The filtrate was washed with water, brine, dried over anhydrous sodium sulphate and concentrated under reduced pressure to give the residue. The crude product was purified via silica gel column chromatography with MeOH and DCM (3:97) to afford the desired compound (1.7 g, yield: 55.1%) as an off white solid. $^1$H NMR (300 MHz, DMSO-d$_6$): δ 4.46 (d, J=3.6 Hz, 1H), 3.73 (m, 1H), 3.40 (m, 1H), 3.19-3.16 (m, 2H), 2.81-2.77 (m, 1H), 2.62-2.58 (m, 1H), 2.30-2.26 (m, 1H), 2.16-2.09 (m, 2H), 1.99-1.92 (m, 1H), 1.80-1.62 (m, 6H), 1.38 (s, 9H), 1.35-1.23 (m, 2H).

Step 2: Synthesis of tert-butyl (S)-2-((4-fluoropiperidin-1-yl)methyl)pyrrolidine-1-carboxylate

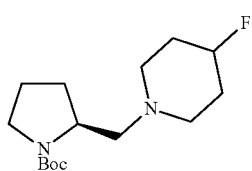 [SMILES: CC(C)(C)OC(=O)N1CCC[C@H]1CN1CCC(F)CC1]

To a stirred solution of tert-butyl (S)-2-((4-hydroxypiperidin-1-yl)methyl)pyrrolidine-1-carboxylate (step 1, 1.7 g, 5.98 mmol) in DCM (25 ml) under N$_2$ atmosphere at 0° C., was added DAST (1.1 ml, 6.58 mmol) and stirred for about 2 hours. After completion of the reaction (monitored by TLC), the reaction mixture was quenched by addition of ice cold water. The solution was extracted with DCM (2×50 mL) and the combined organic phases were washed with brine, dried over Na$_2$SO$_4$ and concentrated under reduced pressure to give the crude product. Purification by column chromatography with MeOH and DCM (2:98) to afford the desired compound (0.5 g, yield: 29.4%) as an oil. $^1$H NMR (300 MHz, CDCl$_3$): δ 4.76-4.60 (m, 1H), 4.28-4.16 (m, 1H), 4.0-3.82 (m, 1H), 3.35-3.31 (m, 2H), 2.88-2.23 (m, 5H), 2.05-1.85 (m, 6H), 1.46 (s, 9H), 1.27 (m, 2H).

Step 3: Synthesis of (S)-4-fluoro-1-(pyrrolidin-2-ylmethyl)piperidine dihydrochloride To a stirred solution of tert-butyl (S)-2-((4-fluoropiperidin-1-yl)methyl)pyrrolidine-1-carboxylate (step 2, 0.5 g, 1.74 mmol) in dioxane (5 ml), was added 6N HCl in dioxane (5 ml) and stirred for about 2 hours. After completion of the reaction (monitored by TLC), the reaction mixture was concentrated under reduced pressure to afford the desired product (0.452 g, yield: 100%). Next reaction was carried out without any further purification.

Intermediate 8: Preparation of (S)-3,3-difluoro-1-(pyrrolidin-2-ylmethyl)pyrrolidine

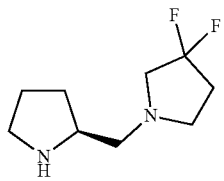 [SMILES: FC1(F)CCN(C[C@@H]2CCCN2)C1]

Step 1: Synthesis of tert-butyl 3-oxopyrrolidine-1-carboxylate

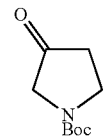

To a stirred solution of tert-butyl (R)-3-hydroxypyrrolidine-1-carboxylate (4.5 g, 24.1 mmol) in DCM (60 ml) under N$_2$ atmosphere, was added DMP (20.45 g, 48.12 mmol) at 0° C. The reaction mixture was allowed to room temperature and stirred for about 2 hours. After completion of the reaction (monitored by TLC), the reaction mixture was quenched with 1:1 mixture of saturated NaHCO$_3$ and saturated Na$_2$S$_2$O$_3$ solution. The reaction mixture was extracted with DCM (2×100 ml). The combined organic layer was washed with brine, dried over anhydrous sodium sulphate and concentrated under reduced pressure to give the residue. Purification by column chromatography with EtOAc and hexane (15:85) to afford the desired compound (3.44 g, yield: 77.3%) as an oil. $^1$H NMR (300 MHz, CDCl$_3$): δ 3.80-3.75 (m, 4H), 2.61-2.56 (m, 2H), 1.48 (s, 9H).

Step 2: Synthesis of tert-butyl 3,3-difluoropyrrolidine-1-carboxylate

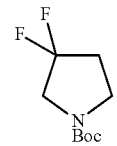

To a stirred solution of tert-butyl 3-oxopyrrolidine-1-carboxylate (step 1, 3.44 g, 18.59 mmol) in DCM (40 ml) under N$_2$ atmosphere at 0° C., was added DAST (2.7 ml, 20.45 mmol) and stirred for about 6 hours. After completion of the reaction (monitored by TLC), the reaction mixture was quenched by addition of ice cold water. The solution was extracted with DCM (2×100 mL) and the combined organic phases were washed with brine, dried over Na$_2$SO$_4$ and concentrated under reduced pressure to give the crude product. Purification by column chromatography with EtOAc and hexane (1:9) to afford the desired compound (1.61 g, yield: 41.92%) as an oil. $^1$H NMR (300 MHz, CDCl$_3$): δ 3.65-3.55 (m, 4H), 2.38-2.24 (m, 2H), 1.46 (s, 9H).

Step 3: Synthesis of 3,3-difluoropyrrolidine hydrochloride

To a stirred solution of tert-butyl 3,3-difluoropyrrolidine-1-carboxylate (step 2, 1.61 g, 7.77 mmol) in dioxane (15 ml), was added 6N HCl in dioxane (20 ml) and stirred for about 2 hours. After completion of the reaction (monitored by TLC), the reaction mixture was concentrated under reduced pressure to afford the desired product (1.11 g, yield: 100%). Next reaction was carried out without any further purification.

Step 4: Synthesis of tert-butyl (S)-2-(3,3-difluoropyrrolidine-1-carbonyl)pyrrolidine-1-carboxylate

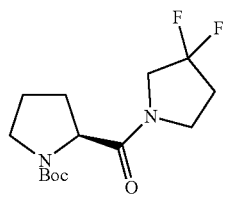 [SMILES: CC(C)(C)OC(=O)N1CCC[C@H]1C(=O)N1CCC(F)(F)C1]

To a stirred solution of (tert-butoxycarbonyl)-L-proline (2.5 g, 11.66 mmol) and 3,3-difluoropyrrolidine hydrochloride (step 3, 1.11 g, 7.77 mmol) and DMAP (0.47 g, 3.88 mmol) in DCM (30 ml), was slowly added DCC (3.2 g, 15.52 mmol) in DCM (20 ml) at 0° C. and allowed to stir at room temperature for about 12 hours. After completion of the reaction (monitored by TLC), the reaction mixture was diluted with DCM and washed with water, saturated NaHCO$_3$ solution, brine and dried over Na$_2$SO$_4$. The solvent was evaporated and to the resulting solid, was added DCM (15 ml) and stirred for about 1 hour and filtered. The filtrate was concentrated under reduced pressure to afford the title compound as a solid. (2.35 g, yield: 100%).

Step 5: Synthesis of (S)-3,3-difluoro-1-prolylpyrrolidine hydrochloride

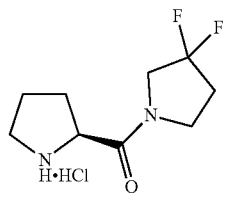

To a stirred solution of tert-butyl (S)-2-(3,3-difluoropyrrolidine-1-carbonyl)pyrrolidine-1-carboxylate (step 4, 2.35 g, 7.73 mmol) in dioxane (20 ml), was added 6N HCl in dioxane (30 ml) and stirred for about 2 hours. After completion of the reaction (monitored by TLC), the reaction mixture was concentrated under reduced pressure to afford the desired product (2.13 g, yield: 100%). Next reaction was carried out without any further purification.

Step 6: Synthesis of (S)-3,3-difluoro-1-(pyrrolidin-2-ylmethyl)pyrrolidine

To a stirred suspension of LiAlH$_4$ (0.58 g, 15.43 mmol) in dry THF (10 ml), was slowly added a solution of (S)-3,3-difluoro-1-prolylpyrrolidine hydrochloride (step 5, 2.13 g, 7.71 mmol) in THF (25 ml) at 0° C. After addition, the reaction mixture was then brought to room temperature and stirred for overnight. After completion of the reaction (monitored by TLC), the reaction mixture was quenched by the sequential addition of 0.6 mL of H$_2$O, 1.8 mL of 15% aq. NaOH and 1.8 mL of H$_2$O. The mixture was then poured into EtOAc (100 ml) and stirred for about 30 minutes. The insoluble material was removed by filtration through celite and the solvent was removed from the filtrate by rotary evaporation, dried over Na$_2$SO$_4$. The product was isolated by column chromatography on silica gel using MeOH:DCM (2:98) as an eluent to give the desired product (1.43 g, yield: 98%) as a solid. $^1$H NMR (300 MHz, DMSO-d$_6$): δ 3.38-3.27 (m, 3H), 3.07-3.03 (m, 1H), 2.92-2.67 (m, 4H), 2.36-2.34 (m, 1H), 2.26-2.14 (m, 2H), 1.76-1.58 (m, 4H); ES Mass: 191.10 [M+H]$^+$.

Intermediate 9: Preparation of (S)-4,4-difluoro-1-(pyrrolidin-2-ylmethyl)piperidine

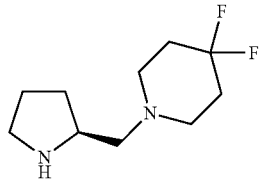 [SMILES: FC1(F)CCN(C[C@@H]2CCCN2)CC1]

Step 1: Synthesis of tert-butyl 4,4-difluoropiperidine-1-carboxylate

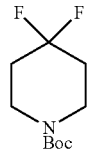

To a stirred solution of tert-butyl 4-oxopiperidine-1-carboxylate (5.0 g, 25.12 mmol) in DCM (50 ml) under N$_2$ atmosphere at 0° C., was added DAST (3.7 ml, 27.63 mmol) and stirred for about 6 hours. After completion of the reaction (monitored by TLC), the reaction mixture was quenched by addition ice cold water. The solution was extracted with DCM (2×100 mL) and the combined organic phases were washed with brine, dried over Na$_2$SO$_4$ and concentrated under reduced pressure to give the crude product. Purification by column chromatography with EtOAc and hexane (1:9) to afford the desired compound (3.73 g, yield: 67.2%) as an oil. $^1$H NMR (300 MHz, CDCl$_3$): δ 3.56-3.52 (m, 4H), 1.99-1.86 (m, 4H), 1.46 (s, 9H).

Step 2: Synthesis of 4,4-difluoropiperidine hydrochloride

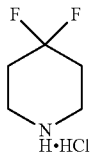

To a stirred solution of tert-butyl 4,4-difluoropiperidine-1-carboxylate (step 1, 3.73 g, 16.87 mmol) in dioxane (20 ml), was added 6N HCl in dioxane (30 ml) and stirred for about 2 hours. After completion of the reaction (monitored by TLC), the reaction mixture was concentrated under reduced pressure to afford the desired product (2.64 g, yield: 100%). Next reaction was carried out without any further purification.

Step 3: Synthesis of tert-butyl (S)-2-(4,4-difluoropiperidine-1-carbonyl)pyrrolidine-1-carboxylate

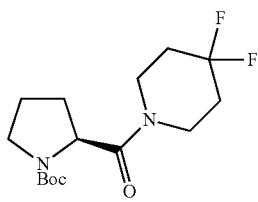 [SMILES: CC(C)(C)OC(=O)N1CCC[C@H]1C(=O)N1CCC(F)(F)CC1]

To a stirred solution of (tert-butoxycarbonyl)-L-proline (5.42 g, 25.22 mmol) and 4,4-difluoropiperidine hydrochloride (step 2, 2.64 g, 16.81 mmol) and DMAP (1.0 g, 8.4 mmol) in DCM (70 ml), was slowly added DCC (6.92 g, 33.63 mmol) in DCM (40 ml) at 0° C. and allowed to stir at room temperature for about 12 hours. After completion of the reaction (monitored by TLC), the reaction mixture was diluted with DCM and washed with water, saturated NaHCO$_3$ solution, brine and dried over Na$_2$SO$_4$. The solvent was evaporated and to the resulting solid, was added DCM (30 ml) and stirred for about 1 hour and filtered. The filtrate was concentrated under reduced pressure to afford the title compound (4.4 g, yield: 82.24%) as a solid. $^1$H NMR (300 MHz, CDCl$_3$): δ 4.72-4.67 (m, 1H), 3.93-3.41 (m, 6H), 2.22-1.82 (m, 6H), 1.46 (s, 9H), 1.45-1.28 (m, 2H); ES Mass: 336.28 [M+NH$_4$]+.

Step 4: Synthesis of (S)-4,4-difluoro-1-propylpiperidine hydrochloride

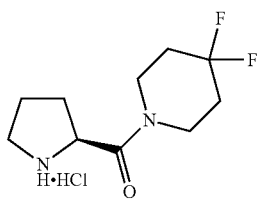

To a stirred solution of tert-butyl (S)-2-(4,4-difluoropiperidine-1-carbonyl)pyrrolidine-1-carboxylate (4.4 g, 13.82 mmol) in dioxane (30 ml), was added 6N HCl in dioxane (25 ml) and stirred for 2 h. After completion of the reaction (monitored by TLC), the reaction mixture was concentrated under reduced pressure to afford the desired product (3.51 g, yield: 100%). Next reaction was carried out without any further purification.

Step 5: Synthesis of (S)-4,4-difluoro-1-(pyrrolidin-2-ylmethyl)piperidine

To a stirred suspension of LiAlH$_4$ (1.1 g, 27.63 mmol) in dry THF (15 ml), was slowly added a solution of (S)-4,4-difluoro-1-propylpiperidine hydrochloride (step 4, 3.51 g, 13.81 mmol) in THF (40 ml) at 0° C. After addition, the reaction mixture was then brought to room temperature and stirred for overnight. After completion of the reaction (monitored by TLC), the reaction mixture was quenched by the sequential addition of 1.0 mL of H$_2$O, 3 mL of 15% aq. NaOH and 3 mL of H$_2$O. The mixture was then poured into EtOAc (100 ml) and stirred for 30 min. The insoluble material was removed by filtration through celite and the solvent was removed from the filtrate by rotary evaporation, dried over Na$_2$SO$_4$. The product was isolated by column chromatography on silica gel using MeOH:DCM (3:97) as an eluent to give the desired product (2.64 g, yield: 94%) as a solid. $^1$H NMR (300 MHz, DMSO-d$_6$): δ 3.16-3.05 (m, 2H), 2.84-2.61 (m, 3H), 2.52 (m, 1H), 2.33-2.18 (m, 2H), 2.01-1.47 (m, 6H), 1.39-1.01 (m, 2H); ES Mass: 205.15 [M+H]$^+$.

Intermediate 10: Preparation of 2-(5-(4-chlorophenyl)-1H-imidazol-2-yl)propan-2-amine hydrochloride

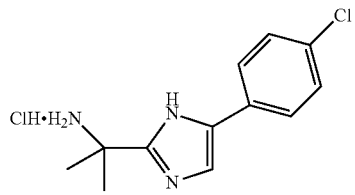

Step 1: Synthesis of 2-(4-chlorophenyl)-2-oxoethyl 2-((tert-butoxycarbonyl)amino)-2-methyl propanoate

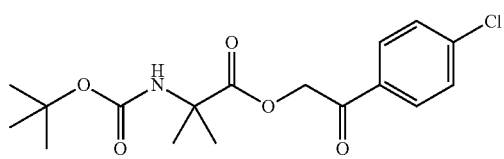 [SMILES: CC(C)(C)OC(=O)NC(C)(C)C(=O)OCC(=O)c1ccc(Cl)cc1]

To a stirred solution of 2-((tert-butoxycarbonyl)amino)-2-methylpropanoic acid (11.0 g, 54.18 mmol, 1.0 eq) in DCM (250 ml) at 0° C. was added DIPEA (48 ml, 270.93 mmol, 5.0 eq) and 2-bromo-1-(4-chlorophenyl)ethan-1-one (15.2 g, 65.01 mmol, 1.2 eq). The reaction mixture was stirred at room temperature for overnight. TLC indicated starting material was consumed and the desired product was observed. The reaction mixture was diluted with water (200 ml) and extracted with DCM (3×150 ml). The combined organic extracts were dried over sodium sulfate, filtered and evaporated under reduced pressure. The residue was purified by silicagel column chromatography by using DCM as an eluent to obtain the desired product (18.5 g, yield: 96.2%) as a yellow solid. 1H NMR (300 MHz, CDCl$_3$): δ ppm 7.85 (d, J=8.7 Hz, 2H), 7.47 (d, J=8.7 Hz, 2H), 5.34 (s, 2H), 1.61 (s, 6H), 1.44 (s, 9H); ESI-MS: m/z 378.0 (M+Na)$^+$.

Step 2: Synthesis of tert-butyl (2-(5-(4-chlorophenyl)-1H-imidazol-2-yl)propan-2-yl)carbamate

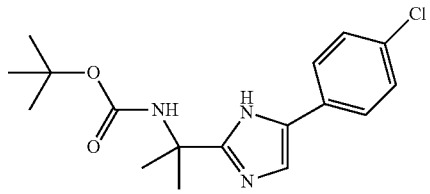 [SMILES: CC(C)(C)OC(=O)NC(C)(C)c1ncc(-c2ccc(Cl)cc2)[nH]1]

To a stirred solution of compound 2-(4-chlorophenyl)-2-oxoethyl 2-((tert-butoxy carbonyl)amino)-2-methylpropanoate (step 1, 18.5 g, 52.09 mmol, 1.0 eq) in toluene (300 ml) was added ammonium acetate (60.23 g, 781.42 mmol, 15.0 eq) and heated to reflux for overnight. TLC indicated starting material was consumed and the desired product was observed. The reaction mixture was evaporated under reduced pressure, diluted with water (300 ml) and extracted with DCM (3×300 ml). The combined organic extracts were dried over sodium sulfate, filtered and evaporated under reduced pressure. The residue was purified by silicagel column chromatography by using 2% MeOH in DCM as an eluent to obtain the desired product (13.0 g, yield: 74.5%) as a yellow solid. 1H NMR (300 MHz, CDCl$_3$): δ ppm 7.62 (d, J=8.1 Hz, 2H), 7.33 (d, J=8.4 Hz, 2H), 7.20 (s, 1H), 5.08 (s, 1H), 1.78 (s, 6H), 1.45 (s, 9H); ESI-MS: m/z 336.1 (M+H)$^+$.

Step 3: Synthesis of 2-(5-(4-chlorophenyl)-1H-imidazol-2-yl)propan-2-amine hydrochloride To tert-butyl (2-(5-(4-chlorophenyl)-1H-imidazol-2-yl)propan-2-yl)carbamate (step 2, 4.0 g, 11.93 mmol, 1.0 eq) in RB flask at 0° C. was added 3N HCl in methanol (100 ml). The reaction mixture was allowed to stir at room temperature for overnight. TLC indicated starting material was consumed and the desired product was observed. The reaction mixture was evaporated to dryness, washed with n-hexane (100 mL) and dried under vacuum to obtain the desired product (3.0 g, yield: 92.8%) as a yellow solid.

Intermediate 11: Preparation of N-(4-chlorobenzyl)-N$^2$,N$^2$-dimethylethane-1,2-diamine

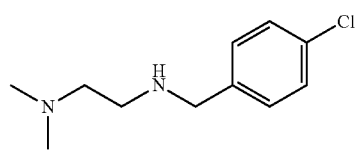

To a stirred solution of 4-chlorobenzaldehyde (15.0 g, 107.14 mmol, 1.0 eq) in MeOH (250 ml) at 0° C. was added N$^1$,N$^1$-dimethylethane-1,2-diamine (11.65 ml, 107.14 mmol, 1.0 eq) and sodium borohydride (3.85 g, 107.14 mmol, 1.0 eq). The reaction mixture was allowed to stir at room temperature for about 16 hours. After completion of the reaction (monitored by TLC), the reaction mixture was cooled to 0° C., quenched with saturated ammonium chloride solution (20 ml) and extracted with ethyl acetate (3×200 ml). The combined organic extracts were washed with water (100 ml), dried over sodium sulfate, filtered and evaporated under reduced pressure to obtain the desired product (15.0 g, yield: 66%) as a colour less liquid. 1H NMR (300 MHz, DMSO-d$_6$): δ ppm 7.32-7.23 (m, 4H), 3.76 (s, 2H), 2.66 (t, J=6.3 Hz, 2H), 2.41 (t, J=6.3 Hz, 2H), 2.19 (s, 6H); ESI-MS: m/z 213.08 (M+H)$^+$.

EXAMPLES

Example 1: Preparation of (1R,3S)-3-(((((3aR,5aR,5bR,7aR,9S,11aR,11bR,13aS)-1-isopropyl-5a,5b,8,8,11a-pentamethyl-2-oxo-3a-((S)-2-(5-phenyl-1H-imidazol-2-yl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethlcyclobutane-1-carboxylic acid

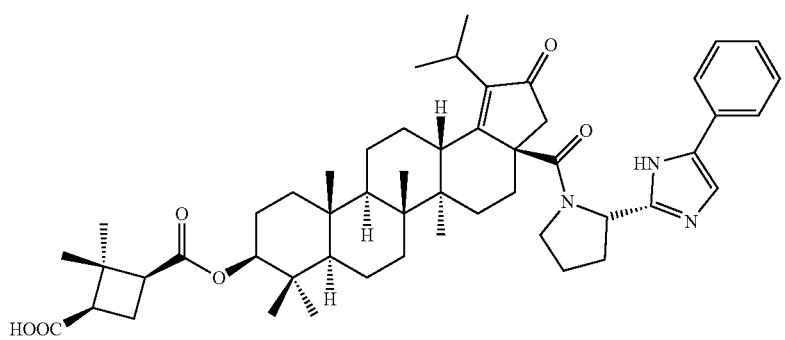

Step 1: Synthesis of ((1R,3aS,5aR,5bR,7aR,9S,11aR,11bR,13aR,13bR)-9-acetoxy-5a,5b,8,8,11a-pentamethyl-1-(prop-1-en-2-yl)icosahydro-3aH-cyclopenta[a]chrysen-3a-yl)methyl acetate

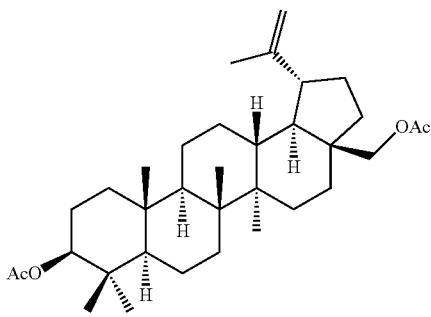

A mixture of (1R,3aS,5aR,5bR,7aR,9S,11aR,11bR,13aR,13bR)-3a-(hydroxymethyl)-5a,5b,8,8,11a-pentamethyl-1-(prop-1-en-2-yl)icosahydro-1H-cyclopenta[a]chrysen-9-ol (150 g, 0.339 mol, 1.0 eq) and acetic anhydride (1.28 Ltr) were stirred at 140° C. for about 1.5 hours. After completion of the reaction (monitored by TLC), the reaction mixture was cooled down to room temperature and then stirred at 0° C. for about 30 minutes. The obtained solid was filtered, washed with n-hexane (50 ml) and dried under vacuum to obtain the desired product (160 g, yield: 90%) as an off-white solid. 1H NMR (300 MHz, CDCl$_3$): δ ppm 4.68 (s, 1H), 4.59 (s, 1H), 4.50-4.43 (m, 1H), 4.25 (d, J=10.8 Hz, 1H), 3.85 (d, J=11.1 Hz, 1H), 2.50-2.40 (m, 1H), 2.07 (s, 3H), 2.04 (s, 3H), 2.0-0.94 (m, 23H), 1.68 (s, 3H), 1.03 (s, 3H), 0.96 (s, 3H), 0.88-0.75 (m, 10H).

Step 2: Synthesis of ((3aS,5aR,5bR,7aR,9S,11aR,11bR,13aS)-9-acetoxy-1-isopropyl-5a,5b,8,8,11a-pentamethyl-2,3,4,5,5a,5b,6,7,7a,8,9,10,11,11a,11b,12,13,13a-octadecahydro-3aH-cyclopenta[a]chrysen-3a-yl)methyl acetate

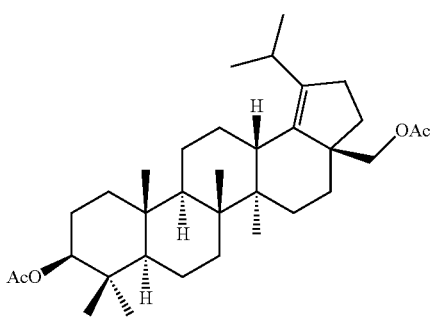

HBr in acetic acid (160 ml, 33%), was added to a suspension of ((1R,3aS,5aR,5bR,7aR,9S,11aR,11bR,13aR,13bR)-9-acetoxy-5a,5b,8,8,11a-pentamethyl-1-(prop-1-en-2-yl)icosahydro-3aH-cyclopenta[a]chrysen-3a-yl)methyl acetate (step 1, 80 g, 152.09 mmol, 1.0 eq) in toluene (160 ml), Ac$_2$O (160 ml) and acetic acid (160 ml) previously heated at 105° C. The reaction mixture was stirred and heated at this temperature for about 1.5 hours. After cooling down to room temperature, another 80 g batch with the same procedure was combined and quenched with sodium acetate (192 g). The resulting reaction mixture was evaporated to dryness. The pale brownish residue was taken up in CH$_2$Cl$_2$ (1200 ml) and the organic phase was washed with water (2×500 ml). The organic layer was dried over sodium sulfate and evaporated under reduced pressure. The residue was recrystallized over ethanol and CH$_2$Cl$_2$ gave the desired product (110 g, yield: 68.7%) as a white solid. 1H NMR (300 MHz, CDCl$_3$): δ ppm 4.52-4.45 (m, 1H), 4.03 (d, J=10.8 Hz, 1H), 3.98 (d, J=10.8 Hz, 1H), 3.19-3.08 (m, 1H), 2.46-2.38 (m, 1H), 2.28-2.22 (m, 2H), 2.04 (s, 3H), 2.03 (s, 3H), 2.0-1.83 (m, 2H), 1.78-1.61 (m, 6H), 1.57-1.44 (m, 3H), 1.43-1.08 (m, 8H), 1.06 (s, 3H), 1.02-0.88 (m, 12H), 0.84 (s, 3H), 0.83 (s, 3H), 0.78 (m, 1H); ESI-MS: m/z 549.43 (M+Na)$^+$.

Step 3: Synthesis of ((3aR,5aR,5bR,7aR,9S,11aR,11bR,13aS)-9-acetoxy-1-isopropyl-5a,5b,8,8,11a-pentamethyl-2-oxo-2,3,4,5,5a,5b,6,7,7a,8,9,10,11,11a,11b,12,13,13a-octadecahydro-3aH-cyclopenta[a]chrysen-3a-yl)methyl acetate

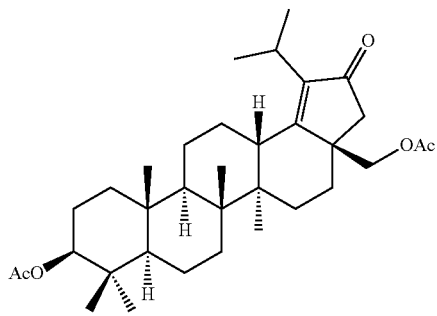

To a stirred solution of ((3aS,5aR,5bR,7aR,9S,11aR,11bR,13aS)-9-acetoxy-1-iso propyl-5a,5b,8,8,11a-pentamethyl-2,3,4,5,5a,5b,6,7,7a,8,9,10,11,11a,11b,12,13,13a-octadecahydro-3aH-cyclopenta[a]chrysen-3a-yl)methyl acetate (step 2, 90 g, 171.10 mmol, 1.0 eq) in Toluene (1000 ml) was added AcOH (1190 ml), Ac$_2$O (290 ml), sodium dichromate dihydrate (61.18 g, 205.3 mmol, 1.2 eq) and sodium acetate (84.18 g, 1026.6 mmol, 6.0 eq). The reaction mixture was stirred and heated at 60° C. for about 16 hours. TLC indicated starting material was consumed and the desired product was observed. After cooling down, the reaction mixture was diluted with water (500 ml) and extracted with ethyl acetate (3×350 ml). The organic phase was washed successively with water (200 ml), saturated solution of sodium carbonate (2×200 ml) and brine solution (2×200 ml). The organic layer was dried over sodium sulfate, filtered and concentrated under reduced pressure to afford a sticky oil. The sticky oil was triturated with methanol (500 ml), precipitates formed were collected by filtration and dried under vacuum to obtain the desired product (74 g, yield: 80%) as a white solid. 1H NMR (300 MHz, CDCl$_3$): δ ppm 4.48 (dd, J=10.2, 6.3 Hz, 1H), 4.33 (d, J=10.8 Hz, 1H), 4.05 (d, J=11.1 Hz, 1H), 3.22-3.12 (m, 1H), 2.86 (dd, J=12.3, 3.3 Hz, 1H), 2.38 (d, J=18.6 Hz, 1H), 2.05 (s, 3H), 1.99 (s, 3H), 1.93-0.75 (m, 40H).

Step 4: Synthesis of (3aR,5aR,5bR,7aR,9S,11aR, 11bR,13aS)-3a-(hydroxymethyl)-1-isopropyl-5a,5b, 8,8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl acetate

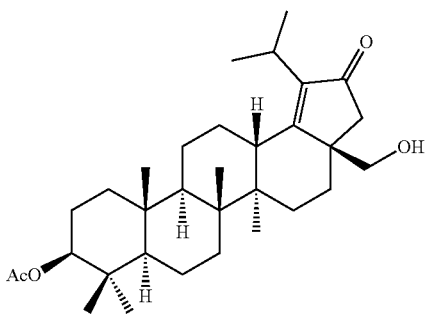

To a stirred solution of ((3aR,5aR,5bR,7aR,9S,11aR, 11bR,13aS)-9-acetoxy-1-iso propyl-5a,5b,8,8,8,11a-pentamethyl-2-oxo-2,3,4,5,5a,5b,6,7,7a,8,9,10,11,11a,11b,12, 13,13a-octadecahydro-3 aH-cyclopenta[a]chrysen-3a-yl) methyl acetate (step 3, 74 g, 137.03 mmol, 1.0 eq) in a mixture of ethanol (2 L):toluene (2 L) (1:1) was added potassium hydroxide (9.2 g, 164.44 mmol, 1.2 eq). The reaction mixture was stirred vigorously at room temperature for about 1 hour. After completion of the reaction (monitored by TLC), the reaction mixture was neutralized with aqueous 1N HCl to pH-7 and evaporated to dryness. The obtained residue was taken up in water (200 ml) and a small amount of acetone (20 ml). The precipitates formed were collected by filtration, washed with water (50 ml) and dried in vacuo to obtain the desired product (60 g, yield: 88%) as a white solid. 1H NMR (300 MHz, CDCl$_3$): δ ppm 4.49 (dd, J=10.5, 5.7 Hz, 1H), 3.73 (d, J=10.8 Hz, 1H), 3.66 (d, J=10.8 Hz, 1H), 3.25-3.14 (m, 1H), 2.78 (dd, J=12.3, 3.3 Hz, 1H), 2.43 (d, J=18.6 Hz, 1H), 2.05 (s, 3H), 2.02-1.65 (m, 8H), 1.62-1.25 (m, 8H), 1.24-1.17 (m, 7H), 1.13 (s, 3H), 1.12-0.97 (m, 1H), 0.94 (s, 3H), 0.92 (s, 3H), 0.86 (s, 3H), 0.85 (s, 3H), 0.80 (m, 1H); ESI-MS: m/z 521.35 (M+Na)$^+$.

Step 5: Synthesis of (3aR,5aR,5bR,7aR,9S,11aR, 11bR,13aS)-3a-formyl-1-isopropyl-5a,5b,8,8,11a-pentamethyl-2-oxo-3,3a,4,5,5a,5b,6,7,7a,8,9,10,11, 11a,11b,12,13,13a-octadecahydro-2H-cyclopenta[a] chrysen-9-yl acetate

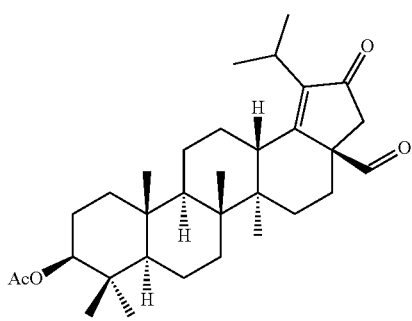

To a stirred solution of (3aR,5aR,5bR,7aR,9S,11aR,11bR, 13aS)-3a-(hydroxymethyl)-1-isopropyl-5a,5b,8,8,11a-pentamethyl-2-oxo-3,3a,4,5,5a,5b,6,7,7a,8,9,10,11,11a,11b,12, 13,13a-octadecahydro-2H-cyclopenta[a]chrysen-9-yl acetate (step 4, 60 g, 120.48 mmol, 1.0 eq) in CH$_2$Cl$_2$ (1.5 L) at room temperature was added pyridinium chlorochromate (77.71 g, 361.44 mmol, 3.0 eq) and silicagel (100-200 mesh) (77 g). The reaction mixture was stirred at room temperature for about 1 hour. After completion of the reaction (monitored by TLC), the reaction mixture was diluted with water (50 ml) and extracted with CH$_2$Cl$_2$ (3×500 ml). The combined organic extracts were washed with water (2×250 ml) and saturated sodium bicarbonate solution (200 ml). The organic layer was dried over sodium sulfate and evaporated under reduced pressure. The residue was purified by silicagel column chromatography by using 8% ethyl acetate in hexanes as an eluent to obtain the desired product (39 g, 65% yield) as a white solid. 1H NMR (300 MHz, CDCl$_3$): δ ppm 9.31 (s, 1H), 4.48 (dd, J=10.5, 6.0 Hz, 1H), 3.32-3.18 (m, 1H), 2.59-2.51 (m, 1H), 2.43-2.33 (m, 2H), 2.10-2.0 (m, 2H), 2.05 (s, 3H), 1.97-1.80 (m, 2H), 1.80-1.60 (m, 3H), 1.53-1.18 (m, 15H), 1.12-1.05 (m, 1H), 1.03 (s, 3H), 0.94 (s, 3H), 0.90 (s, 3H), 0.85 (s, 3H), 0.84 (s, 3H), 0.79 (m, 1H).

Step 6: Synthesis of (3aR,5aR,5bR,7aR,9S,11aR, 11bR,13aS)-9-acetoxy-1-isopropyl-5a,5b,8,8,11a-pentamethyl-2-oxo-2,3,4,5,5a,5b,6,7,7a,8,9,10,11, 11a,11b,12,13,13a-octadecahydro-3aH-cyclopenta[a] chrysene-3a-carboxylic acid

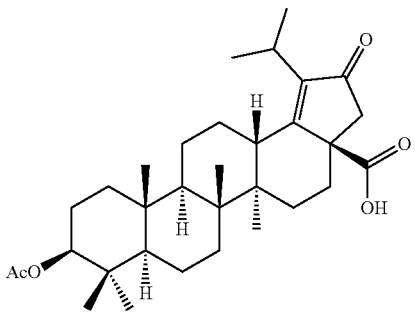

To a stirred solution of (3aR,5aR,5bR,7aR,9S,11aR,11bR, 13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (step 5, 10.0 g, 20.16 mmol, 1.0 eq) in t-butanol (1000 ml), THF (200 ml) and 2-methyl-2-butene (6 ml) at 0° C. was added slowly a solution of NaClO$_2$ (21.77 g, 241.93 mmol, 12.0 eq) and NaH$_2$PO$_4$ (24.19 g, 201.6 mmol, 10.0 eq) in water (200 ml) and stirred over 15 minutes. After stirring at 0° C. for about 10 minutes, the reaction mixture was warmed to room temperature and stirred for another 30 minutes. TLC indicated starting material was consumed and the desired product was observed. The reaction mixture was diluted with EtOAc (200 ml), organic layer was separated and was washed with water (250 ml). The organic layer was dried over sodium sulfate, filtered and evaporated under reduced pressure. The crude compound was washed with n-hexane (50 ml) followed by MTBE (20 ml), filtered and dried under vacuum to obtain the desired product (7.0 g, yield: 68%) as a white solid. 1H NMR (300 MHz, DMSO-d$^6$): δ ppm 12.63 (brs, 1H), 4.42-4.35 (m, 1H), 3.22-3.10 (m, 1H), 2.74-2.63 (m, 1H), 2.41-2.25 (m, 2H), 2.13 (d, J=18.6 Hz, 1H), 2.03 (s, 3H), 1.95-1.62 (m, 5H), 1.62-1.18 (m, 11H), 1.15-1.02 (m, 7H), 0.98 (s, 3H), 0.90 (s, 3H), 0.86 (s, 3H), 0.80 (s, 6H); ESI-MS: m/z 535.3 (M+Na)⁺.

Step 7: Synthesis of (3aR,5aR,5bR,7aR,9S,11aR, 11bR,13aS)-3a-(chlorocarbonyl)-1-isopropyl-5a,5b, 8,8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl acetate

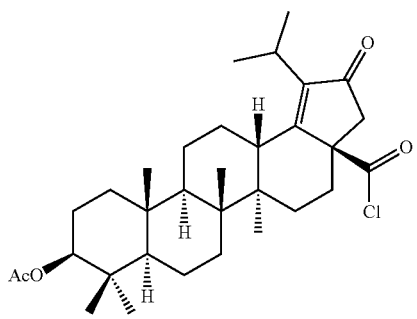

To a stirred solution of (3aR,5aR,5bR,7aR,9S,11aR,11bR, 13aS)-9-acetoxy-1-iso propyl-5a,5b,8,8,8,11a-pentamethyl-2-oxo-2,3,4,5,5a,5b,6,7,7a,8,9,10,11,11a,11b,12,13,13a-octadecahydro-3aH-cyclopenta[a]chrysene-3a-carboxylic acid (step 6, 2.0 g, 3.90 mmol, 1.0 eq) in DCM (20 ml) at 0° C. under nitrogen atmosphere was added oxalyl chloride (10.2 ml, 117 mmol, 30 eq). The reaction mixture was allowed to stir at room temperature for about 4 hours. After completion of the reaction (monitored by TLC), the reaction mixture was evaporated under reduced pressure to obtain the desired product (2.07 g) as an oil, which is used as such for next step without further purification.

Step 8: Synthesis of (3aR,5aR,5bR,7aR,9S,11aR, 11bR,13aS)-1-isopropyl-5a,5b,8,8,11a-pentamethyl-2-oxo-3a-((S)-2-(5-phenyl-1H-imidazol-2-yl)pyrrolidine-1-carbonyl)-3,3a,4,5,5a,5b,6,7,7a,8,9,10,11,11a, 11b,12,13,13a-octadecahydro-2H-cyclopenta[a] chrysen-9-yl acetate

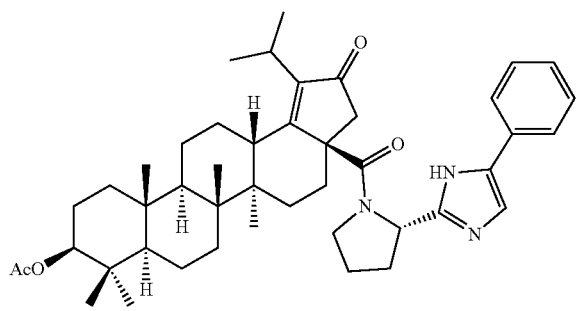

To a stirred solution of (S)-5-phenyl-2-(pyrrolidin-2-yl)-1H-imidazole hydrochloride (prepared as described in WO 2014/105926 A1, 1.66 g, 7.80 mmol, 2.0 eq) in DCM (30 ml) at 0° C. under nitrogen atmosphere was added Et₃N (2.71 ml, 19.5 mmol, 5.0 eq) and (3aR, 5aR,5bR,7aR,9S, 11aR,11bR,13aS)-3a-(chlorocarbonyl)-1-isopropyl-5a,5b,8, 8,8,11a-pentamethyl-2-oxo-3,3a,4,5,5a,5b,6,7,8,9,10,11, 11a,11b,12,13,13a-octadecahydro-2H-cyclopenta[a]chrysen-9-yl acetate (step 7, 2.07 g, 3.90 mmol, 1.0 eq) in DCM (10 ml). The reaction mixture was stirred at room temperature for about 16 hours. After completion of the reaction (monitored by TLC), the reaction mixture was diluted with water (50 ml) and extracted with CH₂Cl₂ (3×50 ml). The combined organic extracts were washed with water (2×100 ml), dried over Na₂SO₄, filtered and evaporated under reduced pressure. The crude compound was purified by silicagel column chromatography by using 60% ethyl acetate in hexane as an eluent to obtain the desired product (1.8 g, yield: 65.4%) as an off-white solid. 1H NMR (300 MHz, CDCl₃): δ ppm 10.49 (s, 0.3H), 10.12 (brs, 0.6H), 7.75 (d, J=7.5 Hz, 1H), 7.50-7.30 (m, 3H), 7.25-7.14 (m, 2H), 5.30 (dd, J=7.8, 4.8 Hz, 1H), 4.43 (dd, J=10.5, 4.2 Hz, 1H), 3.30-3.12 (m, 3H), 2.96-2.79 (m, 1H), 2.78-2.68 (m, 1H), 2.55-2.45 (m, 1H), 2.40-2.17 (m, 3H), 2.16-2.08 (m, 1H), 2.07-2.0 (m, 1H), 2.03 (s, 3H), 1.99-1.13 (m, 23H), 1.05-0.57 (m, 15H); ESI-MS: m/z 730.6 (M+Na)⁺.

Step 9: Synthesis of (3aR,5aR,5bR,7aR,9S,11aR, 11bR,13aS)-9-hydroxy-1-isopropyl-5a,5b,8,8,11a-pentamethyl-3a-((S)-2-(5-phenyl-H-imidazol-2-yl) pyrrolidine-1-carbonyl)-3,3a,4,5,5a,5b,6,7,7a,8,9,10, 11,11a,11b,12,13,13a-octadecahydro-2H-cyclopenta [a]chrysen-2-one

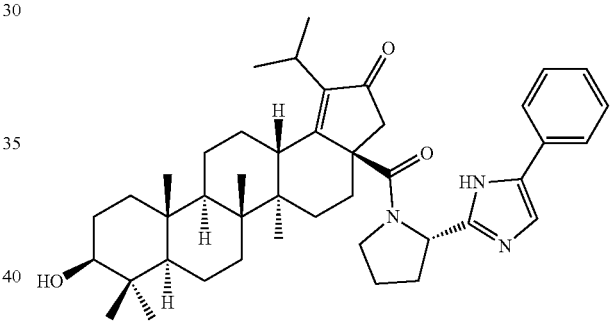

To a stirred solution of (3aR,5aR,5bR,7aR,9S,11aR,11bR, 13aS)-1-isopropyl-5a,5b,8,8,11a-pentamethyl-2-oxo-3a-((S)-2-(5-phenyl-1H-imidazol-2-yl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl acetate (step 8, 1.8 g, 2.54 mmol, 1.0 eq) in 1,4-dioxane (80 ml) was added concentrated HCl (28 ml). The reaction mixture was stirred at room temperature for overnight. TLC indicated starting material was consumed and the desired product was observed. The reaction mixture was diluted with water (50 ml) and extracted with EtOAc (2×100 ml). The combined organic extracts were washed with water (100 ml), dried over sodium sulfate, filtered and evaporated under reduced pressure. The residue was purified by silica gel column chromatography by using 60% ethyl acetate in hexanes as an eluent to obtain the desired product (1.0 g, yield: 59%) as a white solid. 1H NMR (300 MHz, DMSO-d₆): δ ppm 14.6 (brs, 1H), 8.08 (brs, 1H), 7.87 (d, J=7.2 Hz, 2H), 7.54-7.32 (m, 1H), 5.11 (t, J=7.8 Hz, 1H), 3.30-3.10 (m, 3H), 3.0-2.92 (m, 1H), 2.72 (m, 1H), 2.66 (m, 1H), 2.43-2.31 (m, 2H), 2.25-2.06 (m, 3H), 2.04-0.71 (m, 24H), 0.84 (s, 3H), 0.82 (s, 3H), 0.58 (s, 6H), 0.46 (s, 3H); ESI-MS: m/z 666.5 (M+H)⁺.

Step 10: Synthesis of 1-benzyl 3-((3aR,5aR,5bR,7aR,9S,11aR,11bR,13aS)-1-isopropyl-5a,5b,8,8,11a-pentamethyl-2-oxo-3a-((S)-2-(5-phenyl-1H-imidazol-2-yl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate

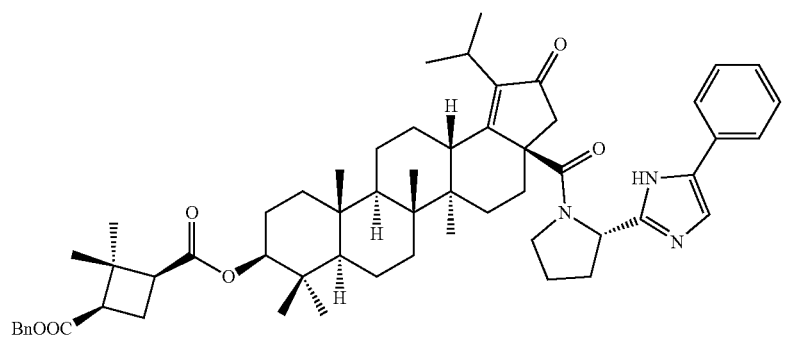

To a stirred solution of (3aR,5aR,5bR,7aR,9S,11aR,11bR,13aS)-9-hydroxy-1-isopropyl-5a,5b,8,8,11a-pentamethyl-3a-((S)-2-(5-phenyl-1H-imidazol-2-yl)pyrrolidine-1-carbonyl)-3,3a,4,5,5a,5b,6,7,7a,8,9,10,11,11a,11b,12,13,13a-octadecahydro-2H-cyclopenta[a]chrysen-2-one (step 9, 1.0 g, 1.50 mmol, 1.0 eq) in toluene (10 ml) at 0° C. under nitrogen atmosphere was added DMAP (0.366 g, 3.0 mmol, 2.0 eq) and (1S,3R)-3-((benzyloxy)carbonyl)-2,2-dimethylcyclobutane-1-carboxylic 2,4,6-trichlorobenzoic anhydride (prepared as described in WO 2013/160810 A2, 1.4 g, 3.0 mmol, 2.0 eq) in toluene (5 ml). The reaction mixture was warmed to room temperature and heated to reflux for overnight. TLC indicated starting material was consumed and the desired product was observed. The reaction mixture was evaporated under reduced pressure, diluted with $CH_2Cl_2$ (200 ml), washed with water (2×50 ml) and brine solution (20 ml). The organic layer was dried over $Na_2SO_4$, filtered and evaporated under reduced pressure. The residue was purified by silicagel column chromatography by using 2% MeOH in DCM as an eluent to obtain the desired product (0.450 g, yield: 33%) as a white solid. 1H NMR (300 MHz, $CDCl_3$): δ ppm 10.52 (brs, 0.3H), 10.14 (brs, 0.6H), 7.78-7.68 (m, 2H), 7.40-7.30 (m, 8H), 7.22-7.15 (m, 1H), 5.40-5.27 (m, 1H), 5.14, 5.09 (ABq, $J_{AB}$=12.3 Hz, 2H), 4.39 (dd, J=11.1, 4.2 Hz, 1H), 3.28-3.12 (m, 3H), 2.90-2.45 (m, 5H), 2.38-2.20 (m, 4H), 2.14-1.10 (m, 26H), 1.03-0.56 (m, 21H); ESI-MS: m/z 910.7 $(M+H)^+$.

Step 11: Synthesis of (1R,3S)-3-((((3aR,5aR,5bR,7aR,9S,11aR,11bR,13aS)-1-isopropyl-5a,5b,8,8,11a-pentamethyl-2-oxo-3a-((S)-2-(5-phenyl-1H-imidazol-2-yl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a suspension of wet 10% Pd/C (0.350 g) in EtOAc (10 ml) was added 1-benzyl 3-((3aR,5aR,5bR,7aR,9S,1aR,11bR,13aS)-1-isopropyl-5a,5b,8,8,11a-pentamethyl-2-oxo-3a-((S)-2-(5-phenyl-1H-imidazol-2-yl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 10, 0.450 g, 0.495 mmol, 1.0 eq) in MeOH (10 ml). To this stirred reaction mixture, ammonium formate (0.156 g, 2.47 mmol, 5.0 eq) was added portion wise and stirred at room temperature for about 16 hours. TLC indicated starting material was consumed and the desired product was observed. The reaction mixture was filtered through a pad of celite, washed with EtOAc (100 ml) and the filtrate was evaporated under reduced pressure. The residue was purified by silicagel column chromatography (eluent: 5% MeOH:$CH_2Cl_2$) to afford a solid, which was taken into n-hexane (10 ml), heated to reflux for about 30 minutes, then cooled to 0° C., filtered and dried under vacuum to give the desired product (0.11 g, yield: 27%) as a white solid. 1H NMR (300 MHz, DMSO-$d_6$): δ ppm 12.18 (brs, 1H), 11.9 (s, 1H), 7.76-7.65 (m, 2H), 7.39 (s, 1H), 7.30-7.23 (m, 2H), 7.14-7.07 (m, 1H), 5.16 (dd, J=7.5, 3.6 Hz, 1H), 4.33-4.26 (m, 1H), 3.25-3.07 (m, 3H), 2.83-2.71 (m, 3H), 2.35-2.25 (m, 3H), 2.14-2.02 (m, 3H), 1.98-0.98 (m, 27H), 0.97-0.65 (m, 14H), 0.75 (s, 3H), 0.69 (s, 3H); ESI-MS: m/z 820.5 (M+H)+; HPLC purity: 91.4%.

Example 2: Preparation of (1R,3S)-3-((((3aR,5aR, 5bR,7aR,9S,11aR,11bR,13aS)-3a-((S)-2-(5-(4-fluorophenyl)-1H-imidazol-2-yl)pyrrolidine-1-carbonyl)-1-isopropyl-5a,5b,8,8,11a-pentamethyl-2-oxo-3,3a,4, 5,5a,5b,6,7,7a,8,9,10,11,11a,11b,12,13,13a-octadecahydro-2H-cyclopenta[a]chrysen-9-yl)oxy) carbonyl)-2,2-dimethlcyclobutane-1-carboxylic acid

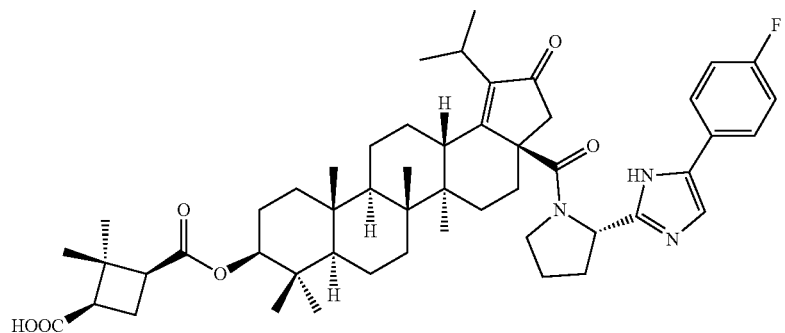

Step 1: Synthesis of (3aR,5aR,5bR,7aR,9S,11aR, 11bR,13aS)-3a-((S)-2-(5-(4-fluorophenyl)-1H-imidazol-2-yl)pyrrolidine-1-carbonyl)-1-isopropyl-5a, 5b,8,8,11a-pentamethyl-2-oxo-3,3a,4,5,5a,5b,6,7,7a, 8,9,10,11,11a,12,13,13a-octadecahydro-2H-cyclopenta[a]chrysen-9-yl acetate Step 2: Synthesis of (3aR,5aR,5bR,7aR,9S,11aR, 11bR,13aS)-3a-((S)-2-(5-(4-fluorophenyl)-1H-imidazol-2-yl)pyrrolidine-1-carbonyl)-9-hydroxy-1-isopropyl-5a,5b,8,8,11a-pentamethyl-3,3a,4,5,5a,5b, 6,7,7a,8,9,10,11,11a,11b,12,13,13a-octadecahydro-2H-cyclopenta[a]chrysen-2-one

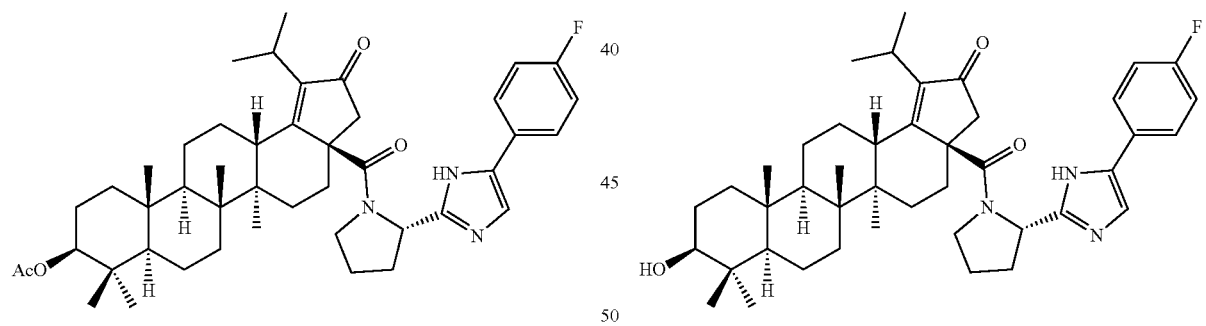

To a stirred solution of (S)-5-(4-fluorophenyl)-2-(pyrrolidin-2-yl)-d: 87.7%) as a yellow 1H-imidazole hydrochloride (prepared as described in WO 2014/105926 A1, 3.91 g, 14.14 mmol, 1.5 eq) in DCM (100 ml) at 0° C. under nitrogen atmosphere was added Et₃N (9.18 ml, 66.0 mmol, 7.0 eq) and (3aR,5aR,5bR,7aR,9S,11aR,11bR,13aS)-3a-(chlorocarbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (Example 1-step 7, 5.0 g, 9.42 mmol, 1.0 eq) in DCM (25 ml). The reaction mixture was allowed to stir at room temperature for overnight. TLC indicated starting material was consumed and the desired product was observed. The reaction mixture was diluted with water (200 ml) and extracted with CH₂Cl₂ (2×200 ml). The combined organic extracts were dried over Na₂SO₄, filtered and evaporated under reduced pressure. The residue was purified by silicagel column chromatography by using 2% MeOH in DCM as an eluent to obtain the desired product (6.0 g, yield: 87.7%) as a yellow solid. H NMR (300 MHz, CDCl₃): δ ppm 10.16 (brs, 0.6H), 7.74-7.68 (m, 2H), 7.10-7.02 (m, 3H), 5.29 (dd, J=7.5, 5.1 Hz, 1H), 4.43 (dd, J=11.7, 5.4 Hz, 1H), 3.33-3.12 (m, 3H), 2.88-2.78 (m, 1H), 2.74-2.66 (m, 1H), 2.49 (d, J=19.2 Hz, 1H), 2.39-2.07 (m, 5H), 2.03 (s, 3H), 2.01-0.84 (m, 22H), 0.91 (s, 3H), 0.81 (s, 3H), 0.78 (s, 3H), 0.74-0.68 (m, 1H), 0.57-0.53 (m, 6H); ESI-MS: m/z 748.5 (M+Na)+.

To a stirred solution of (3aR,5aR,5bR,7aR,9S,11aR,11bR, 13aS)-3a-((S)-2-(5-(4-fluorophenyl)-1H-imidazol-2-yl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl acetate (step 1, 6.0 g, 8.27 mmol, 1.0 eq) in MeOH (200 ml), THF (100 ml) and water (50 ml) at 0° C. was added KOH (4.63 g, 82.7 mmol, 10.0 eq). The reaction mixture was allowed to stir at room temperature for overnight. TLC indicated starting material was consumed and the desired product was observed. The reaction mixture was evaporated under reduced pressure, diluted with water (200 ml) and extracted with DCM (3×100 ml). The combined organic extracts were dried over sodium sulfate, filtered and evaporated under reduced pressure. The residue was purified by silicagel column chromatography by using 2% MeOH in DCM as an eluent to obtain the desired product (5.0 g, yield: 88.5%) as a light yellow solid. $^1$H NMR (300 MHz, CDCl$_3$): δ ppm 10.18 (brs, 1H), 7.74-7.64 (m, 2H), 7.10-7.01 (m, 3H), 5.32-5.28 (m, 1H), 3.30-3.12 (m, 4H), 2.90-2.79 (m, 1H), 2.76-2.67 (m, 1H), 2.49 (d, J=19.2 Hz, 1H), 2.40-2.20 (m, 3H), 2.19-2.02 (m, 3H), 2.01-1.89 (m, 2H), 1.89-0.80 (m, 26H), 0.71 (s, 3H), 0.59-0.55 (m, 6H); ESI-MS: m/z 684.5 (M+H)$^+$.

Step 3: Synthesis of 1-benzyl 3-((3aR,5aR,5bR, 7aR,9S,11aR,11bR,13aS)-3a-((S)-2-(5-(4-fluorophenyl)-1H-imidazol-2-yl)pyrrolidine-1-carbonyl)-1-isopropyl-5a,5b,8,8,11a-pentamethyl-2-oxo-3,3a,4,5, 5a,5b,6,7,7a,8,9,10,11,11a,11b,12,13,13a-octadecahydro-2H-cyclopenta[a]chrysen-9-yl) (1R, 3S)-2,2-dimethylcyclobutane-1,3-dicarboxylate Step 4: Synthesis of (1R,3S)-3-((((3aR,5aR,5bR, 7aR,9S,11aR,11bR,13aS)-3a-((S)-2-(5-(4-fluorophenyl)-1H-imidazol-2-yl)pyrrolidine-1-carbonyl)-1-isopropyl-5a,5b,8,8,11a-pentamethyl-2-oxo-3,3a,4,5, 5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid To a suspension of wet 10% Pd/C (0.5 g) in EtOAc (15 ml) was added 1-benzyl 3-((3aR,5aR,5bR,7aR,9S,1aR,

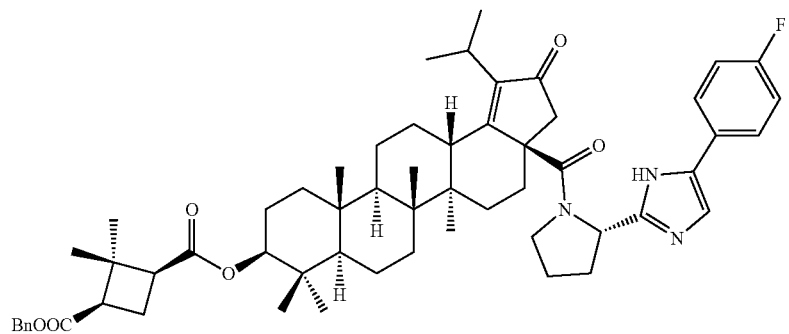

To a stirred solution of (3aR,5aR,5bR,7aR,9S,11aR,11bR, 13aS)-3a-((S)-2-(5-(4-fluorophenyl)-1H-imidazol-2-yl)pyrrolidine-1-carbonyl)-9-hydroxy-1-isopropyl-5a,5b,8,8,11a-pentamethyl-3,3a,4,5,5a,5b,6,7,7a,8,9,10,11,11a,11b,12,13, 13a-octadecahydro-2H-cyclopenta[a]chrysen-2-one (step 2, 1.0 g, 1.46 mmol, 1.0 eq) in toluene (30 ml) at 0° C. under nitrogen atmosphere was added DMAP (0.35 g, 2.92 mmol, 2.0 eq) and (1S,3R)-3-((benzyl oxy)carbonyl)-2,2-dimethylcyclobutane-1-carboxylic 2,4,6-trichlorobenzoic anhydride (prepared as described in WO 2013/160810 A2, 0.82 g, 1.752 mmol, 1.2 eq) in toluene (5 ml). The reaction mixture was heated to reflux for overnight. TLC indicated starting material was consumed and the desired product was observed. The organic phase was evaporated under reduced pressure, diluted with water (30 ml) and extracted with DCM (3×30 ml). The combined organic extracts were dried over sodium sulfate, filtered and evaporated under reduced pressure. The residue was purified by silicagel column chromatography by using 2% MeOH in DCM as an eluent to obtain the desired product (0.8 g, yield: 58.9%) as a yellow solid. 1H NMR (300 MHz, CDCl$_3$): δ ppm 10.2 (brs, 0.5H), 7.74-7.67 (m, 2H), 7.38-7.32 (m, 5H), 7.14-7.01 (m, 3H), 5.32-5.26 (m, 1H), 5.15, 5.09 (ABq, J$_{AB}$=12.3 Hz, 2H), 4.40 (dd, J=11.1, 3.9 Hz, 1H), 3.27-3.14 (m, 3H), 2.97-2.57 (m, 5H), 2.54-2.25 (m, 3H), 2.22-1.0 (m, 28H), 0.95 (s, 3H), 0.91 (s, 3H), 0.90-0.84 (m, 1H), 0.81 (s, 3H), 0.78 (s, 3H), 0.74-0.67 (m, 1H), 0.59-0.52 (m, 6H); ESI-MS: m/z 950.5 (M+Na)$^+$.

11bR,13aS)-3a-((S)-2-(5-(4-fluorophenyl)-1H-imidazol-2-yl)pyrrolidine-1-carbonyl)-1-isopropyl-5a,5b,8,8,11a-pentamethyl-2-oxo-3,3a,4,5,5a,5b,6,7,7a, 8,9,10,11,11a,11b,12, 13,13a-octadecahydro-2H-cyclopenta[a]chrysen-9-yl) (1R, 3S)-2,2-di methylcyclobutane-1,3-dicarboxylate (step 3, 0.8 g, 0.86 mmol, 1.0 eq) in MeOH (15 ml), followed by ammonium formate (0.271 g, 4.31 mmol, 5.0 eq). The reaction mixture was stirred at room temperature for about 2 hours. TLC indicated starting material was consumed and the desired product was observed. The reaction mixture was filtered through a pad of celite, washed with MeOH (200 ml) and the filtrate was evaporated under reduced pressure. The residue was dissolved in DCM (100 ml), washed with water (100 ml), dried over Na$_2$SO$_4$, filtered, evaporated under reduced pressure and purified by silicagel column chromatography by using 2% MeOH in DCM as an eluent to obtain the desired product (0.05 g, yield: 7%) as a white solid. $^1$H NMR (300 MHz, CDCl$_3$): δ ppm 10.59 (s, 0.2H), 10.19 (brs, 0.6H), 7.75-7.68 (m, 2H), 7.12-7.0 (m, 3H), 5.33-5.25 (m, 1H), 4.45-4.38 (m, 1H), 3.27-3.13 (m, 3H), 2.87-2.45 (m, 5H), 2.41-2.20 (m, 3H), 2.18-1.84 (m, 6H), 1.83-0.87 (m, 20H), 1.37 (s, 3H), 1.06 (s, 3H), 0.91 (s, 3H), 0.83 (s, 3H), 0.79 (s, 3H), 0.75-0.68 (m, 1H), 0.55 (s, 3H), 0.53 (s, 3H); ESI-MS: m/z 860.6 (M+Na)+; HPLC: 96.9%.

Example 3: Preparation of (1R,3S)-3-((((3aR,5aR, 5bR,7aR,9S,11aR,11bR,13aS)-1-isopropyl-5a,5b,8, 8,11a-pentamethyl-2-oxo-3a-((S)-2-(5-(pyridin-3-yl)-1H-imidazol-2-yl)pyrrolidine-1-carbonyl)-3,3a,4, 5,5a,5b,6,7,7a,8,9,10,11,11a,11b,12,13,13a-octadecahydro-2H-cyclopenta[a]chrysen-9-yl)oxy) carbonyl)-2,2-dimethlcyclobutane-1-carboxylic acid

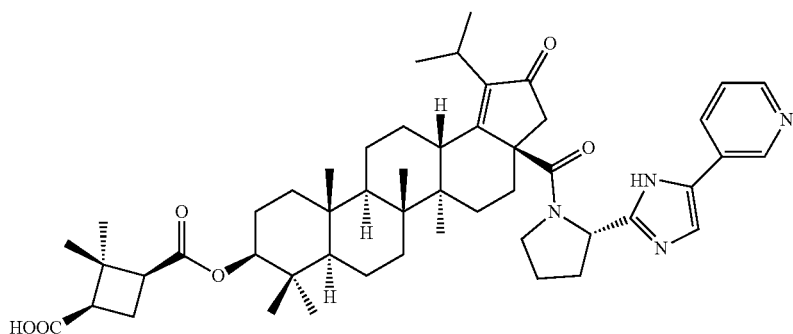

Step 1: Synthesis of (3aR,5aR,5bR,7aR,9S,11aR, 11bR,13aS)-1-isopropyl-5a,5b,8,8,11a-pentamethyl-2-oxo-3a-((S)-2-(5-(pyridin-3-yl)-1H-imidazol-2-yl) pyrrolidine-1-carbonyl)-3,3a,4,5,5a,5b,6,7,7a,8,9,10, 11,11a,11b,12,13,13a-octadecahydro-2H-cyclopenta [a]chrysen-9-yl acetate

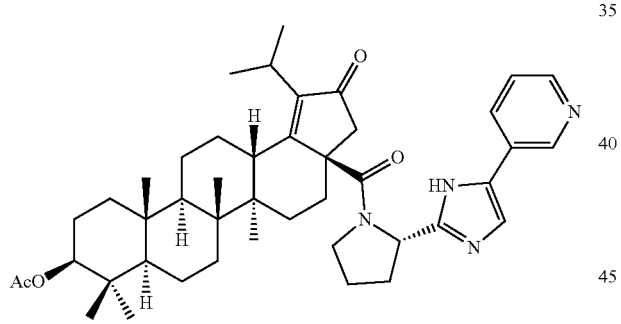

To a stirred solution of (S)-3-(2-(pyrrolidin-2-yl)-1H-imidazol-5-yl)pyridine (prepared as described in WO 2014/105926 A1, 2.42 g, 11.32 mmol, 1.2 eq) in DCM (25 ml) at 0° C. under nitrogen atmosphere was added Et$_3$N (6.57 ml, 47.25 mmol, 5.0 eq) and (3aR, 5aR,5bR,7aR,9S,11aR,11bR, 13aS)-3a-(chlorocarbonyl)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl acetate (Example 1-step 7, 5.0 g, 9.43 mmol, 1.0 eq) dissolved in DCM (25 ml). The reaction mixture was stirred at room temperature for overnight. After completion of the reaction monitored by TLC, the reaction mixture was diluted with DCM (150 ml), washed with water (100 ml), dried over Na$_2$SO$_4$, filtered and evaporated under reduced pressure. The residue was purified by silicagel column chromatography by using 3% MeOH in DCM as an eluent to obtain the desired product (5.0 g, yield: 74.6%) as a light yellow solid. 1H NMR (300 MHz, CDCl$_3$): δ ppm 10.24 (brs, 1H), 8.97 (d, J=1.8 Hz, 1H), 8.45 (dd, J=4.8, 1.5 Hz, 1H), 8.08 (dt, J=8.4, 1.8 Hz, 1H), 7.30-7.22 (m, 2H), 5.33-5.26 (m, 1H), 4.42 (dd, J=11.1, 4.2 Hz, 1H), 3.32-3.12 (m, 3H), 2.91-2.79 (m, 1H), 2.75-2.66 (m, 1H), 2.49 (d, J=19.2, 1H), 2.40-2.20 (m, 3H), 2.17-2.08 (m, 1H), 2.08-2.01 (m, 1H), 2.03 (s, 3H), 2.0-0.83 (m, 22H), 0.91 (s, 3H), 0.80 (s, 3H), 0.76 (s, 3H), 0.74-0.68 (m, 1H), 0.54 (s, 3H), 0.52 (s, 3H); ESI-MS: m/z 731.4 (M+Na)$^+$.

Step 2: Synthesis of (3aR,5aR,5bR,7aR,9S,11aR, 11bR,13aS)-9-hydroxy-1-isopropyl-5a,5b,8,8,11,a-pentamethyl-3a-((S)-2-(5-(pyridin-3-yl)-1H-imidazol-2-yl)pyrrolidine-1-carbonyl)-3,3a,4,5,5a,5b,6,7, 7a,8,9,10,11,11a,11b,12,13,13a-octadecahydro-2H-cyclopenta[a]chrysen-2-one

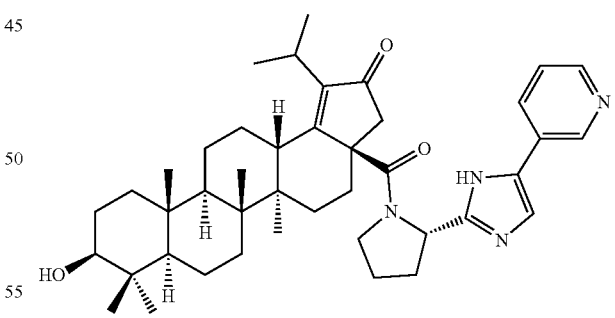

To a stirred solution of (3aR,5aR,5bR,7aR,9S,11aR,11bR, 13aS)-1-isopropyl-5a,5b,8,8,11a-pentamethyl-2-oxo-3a-((S)-2-(5-(pyridin-3-yl)-H-imidazol-2-yl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl acetate (step 1, 3.0 g, 4.23 mmol, 1.0 eq) in MeOH (88 ml), THF (44 ml) and water (22 ml) at 0° C. was added NaOH (1.69 g, 42.3 mmol, 10.0 eq). The reaction mixture was allowed to stir at room temperature for overnight. TLC indicated starting material was consumed and the desired product was observed. The reaction mixture was evaporated under reduced pressure, diluted with EtOAc (100 ml), washed with water (50 ml), dried over sodium sulfate, filtered and evaporated under reduced pressure. The residue was purified by silicagel column chromatography by using 5% MeOH in DCM as an eluent to obtain the desired product (2.5 g, yield: 88.5%) as a light yellow solid. 1H NMR (300 MHz, CD$_3$OD): δ ppm 8.95 (d, J=1.5 Hz, 1H), 8.35 (dd, J=5.1, 1.5 Hz, 1H), 8.18 (dt, J=8.1, 1.8 Hz, 1H), 7.47 (brs, 1H), 7.41 (dd, J=7.8, 5.1 Hz, 1H), 5.25 (t, J=6.6 Hz, 1H), 3.57-3.47 (m, 1H), 3.35-3.22 (m, 2H), 3.12-3.04 (m, 1H), 2.63-2.53 (m, 2H), 2.46-2.32 (m, 1H), 2.26-2.13 (m, 3H), 2.07-1.91 (m, 4H), 1.80-0.85 (m, 28H), 0.65 (s, 3H), 0.43 (s, 3H), 0.42 (s, 3H); ESI-MS: m/z 689.5 (M+Na)$^+$.

Step 3: Synthesis of (3aR,5aR,5bR,7aR,9S,11aR, 11bR,13aS)-1-isopropyl-5a,5b,8,8,11a-pentamethyl-2-oxo-3a-((S)-2-(5-(pyridin-3-yl)-1H-imidazol-2-yl)pyrrolidine-1-carbonyl)-3,3a,4,5,5a,5b,6,7,7a,8,9,10, 11,11a,11b,12,13,13a-octadecahydro-2H-cyclopenta [a]chrysen-9-yl(1S,3R)-2,2-dimethyl-3-(2-phenylacetoxy)cyclobutane-1-carboxylate

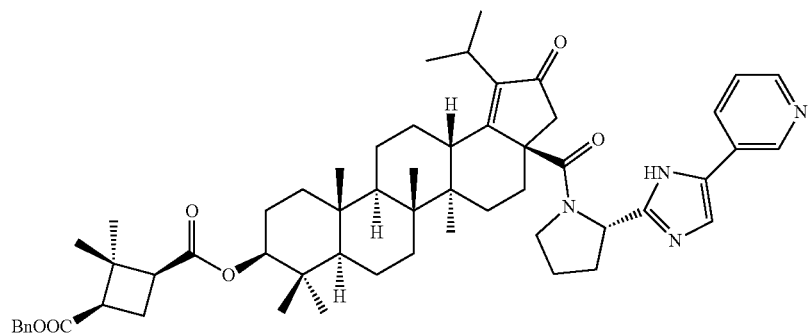

To a stirred solution of (3aR,5aR,5bR,7aR,9S,11aR,11bR, 13aS)-9-hydroxy-1-iso propyl-5a,5b,8,8,11a-pentamethyl-3a-((S)-2-(5-(pyridin-3-yl)-1H-imidazol-2-yl)pyrrolidine-1-carbonyl)-3,3a,4,5,5a,5b,6,7,7a,8,9,10,11,11a,11b,12,13, 13a-octadecahydro-2H-cyclopenta[a]chrysen-2-one (step 2, 1.0 g, 1.50 mmol, 1.0 eq) in toluene (10 ml) under nitrogen atmosphere was added (1S,3R)-3-((benzyloxy)carbonyl)-2,2-dimethylcyclobutane-1-carboxylic 2,4,6-trichlorobenzoic anhydride (prepared as described in WO 2013/160810 A2, 1.05 g, 2.25 mmol, 1.5 eq) dissolved in toluene (5 ml) and DMAP (0.915 g, 7.5 mmol, 5.0 eq). The reaction mixture was heated to reflux for overnight. TLC indicated starting material was consumed and the desired product was observed. The reaction mixture was evaporated under reduced pressure, diluted with EtOAc (200 ml), washed with water (2×50 ml), dried over Na$_2$SO$_4$, filtered and evaporated under reduced pressure. The residue was purified by silicagel column chromatography by using 4% MeOH in DCM as an eluent to obtain the desired product (0.6 g, yield: 43.8%) as a light yellow solid. 1H NMR (300 MHz, CD$_3$OD): δ ppm 8.95 (brs, 1H), 8.36-8.20 (m, 1H), 8.22-8.16 (m, 1H), 7.47 (brs, 1H), 7.44-7.29 (m, 6H), 5.23 (t, J=6.6 Hz, 1H), 5.14, 5.07 (ABq, J$_{AB}$=12.3 Hz, 2H), 4.39-4.31 (m, 1H), 3.33-3.22 (m, 3H), 2.92-2.77 (m, 3H), 2.62-2.48 (m, 4H), 2.48-2.28 (m, 2H), 2.26-2.10 (m, 2H), 2.10-0.98 (m, 26H), 0.95-0.83 (m, 6H), 0.79 (s, 3H), 0.75 (s, 3H), 0.69 (m, 1H), 0.40 (s, 3H), 0.38 (s, 3H).

Step 4: Synthesis of (1R,3S)-3-((((3aR,5aR,5bR, 7aR,9S,11aR,11bR,13aS)-1-isopropyl-5a,5b,8,8,11a-pentamethyl-2-oxo-3a-((S)-2-(5-(pyridin-3-yl)-1H-imidazol-2-yl)pyrrolidine-1-carbonyl)-3,3a,4,5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid To a suspension of wet 10% Pd/C (0.200 g) in EtOAc (10 ml) was added (3aR,5aR, 5bR,7aR,9S,11aR,11bR,13aS)-1-isopropyl-5a,5b,8,8,11a-pentamethyl-2-oxo-3a-((S)-2-(5-(pyridin-3-yl)-1H-imidazol-2-yl)pyrrolidine-1-carbonyl)-3, 3a,4,5,5a,5b,6,7,7a,8,9,10,11,11a,11b,12,13,13a-octadecahydro-2H-cyclopenta[a]chrysen-9-yl (1S,3R)-2,2-dimethyl-3-(2-phenylacetoxy)cyclobutane-1-carboxylate (step 3, 0.5 g, 0.54 mmol, 1.0 eq) dissolved in MeOH (10 ml). To this stirred reaction mixture, ammonium formate (0.17 g, 2.74 mmol, 5.0 eq) was added portion wise and stirred at room temperature for about 3 hours. TLC indicated starting material was consumed and the desired product was observed. The reaction mixture was filtered through a pad of celite, washed with EtOAc and MeOH (1:1, 100 ml). The filtrate was evaporated under reduced pressure and the residue was purified by silicagel column chromatography by using 7% MeOH in CH$_2$Cl$_2$ as an eluent to obtain the desired product (0.1 g, yield: 22%) as a light yellow solid. $^1$H NMR (300 MHz, DMSO-d$^6$): δ ppm 12.1 (brs, 2H), 8.96 (d, J=1.2 Hz, 1H), 8.32 (dd, J=4.8, 1.2 Hz, 1H), 8.05 (dt, J=7.8, 1.8 Hz, 1H), 7.54 (d, J=1.5 Hz, 1H), 7.295 (dd, J=7.8, 4.8 Hz, 1H), 5.15 (dd, J=7.5, 3.6 Hz, 1H), 4.28 (dd, J=10.5, 4.2 Hz, 1H), 3.38 (m, 1H), 3.23-3.09 (m, 2H), 2.82-2.71 (m, 2H), 2.59 (d, J=19.2 Hz, 1H), 2.47-2.42 (m, 3H), 2.37-2.24 (m, 2H), 2.14-2.03 (m, 2H), 2.0-0.98 (m, 26H), 0.89 (s, 3H), 0.83 (s, 3H), 0.81-0.78 (m, 1H), 0.74 (s, 3H), 0.69 (s, 3H), 0.62 (m, 1H), 0.30 (s, 3H), 0.25 (s, 3H); ESI-MS: m/z 821.5 (M+H)$^+$; HPLC: 97.7%.

Example 4: Preparation of (1R,3S)-3-((((3aR,5aR,5bR,7aR,9S,11aR,11bR,13aS)-3a-((R)-[1,3'-bipyrrolidine]-1'-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

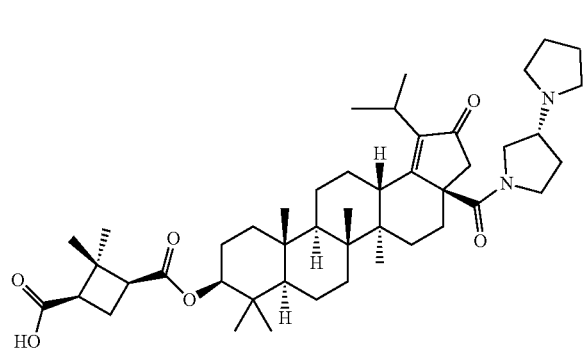

Step 1: Synthesis of (3aR,5aR,5bR,7aR,9S,11aR,11bR,13aS)-3a-((R)-[1,3'-bipyrrolidine]-1'-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate

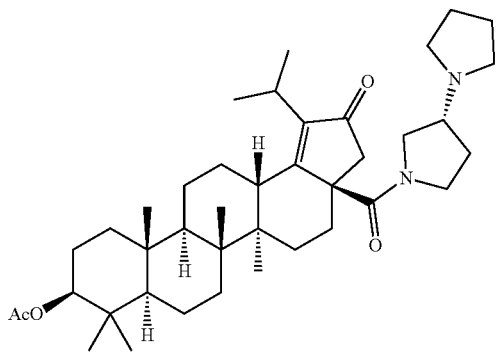

To a stirred solution of (R)-1,3'-bipyrrolidine hydrochloride (Intermediate 4, 1.0 g, 4.67 mmol) in DCM (10 ml) and NEt$_3$ (2.0 ml, 14.41 mmol), was added a solution of (3aR,5aR,5bR,7aR,9S,11aR,11bR,13aS)-3a-(chlorocarbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (Example 1-step 7, 2.4 g, 4.67 mmol) in DCM (25 ml) at 0° C. and allowed to stir at room temperature for about 16 hours. After completion of the reaction (monitored by TLC), the reaction mixture was diluted with DCM, washed with water, brine and dried over Na$_2$SO$_4$. The solvent was evaporated and purified by silica gel column (elution 2% MeOH in DCM) to afford the title compound (2.0 g, yield: 68%) as an off white solid. $^1$H NMR (300 MHz, CDCl$_3$): δ 4.51-4.46 (m, 1H), 3.83-3.67 (m, 2H), 3.56-3.40 (m, 2H), 3.21-3.16 (m, 1H), 3.04-2.97 (m, 1H), 2.71-2.43 (m, 7H), 2.11-1.98 (m, 6H), 1.80-1.07 (m, 26H), 1.03-0.79 (m, 16H).

Step 2: Synthesis of Synthesis of (3aR,5aR,5bR,7aR,9S,11aR,11bR,13aS)-3a-((R)-[1,3'-bipyrrolidine]-1'-carbonyl)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-2-one

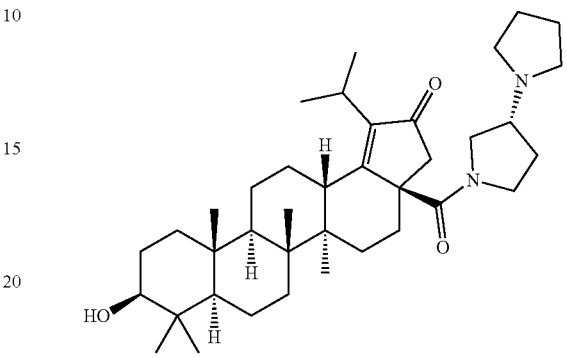

To a stirred solution of (3aR,5aR,5bR,7aR,9S,11aR,11bR,13aS)-3a-((R)-[1,3'-bipyrrolidine]-1'-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (step 1, 2.0 g, 3.14 mmol) in MeOH: THF (10 ml: 10 ml), was added 6N NaOH (10 ml) at 0° C. and allowed to stir at room temperature for about 12 hours. After completion of the reaction (monitored by TLC), the reaction mixture was concentrated under reduced pressure. The reaction mixture was diluted with DCM, washed with water, brine and dried over Na$_2$SO$_4$. The solvent was evaporated, the resulting solid was taken in hexane and stirred for about one hour and filtered to afford the title compound (1.5 g, yield: 80%) as a white solid. $^1$H NMR (300 MHz, CDCl$_3$): δ 3.83-3.66 (m, 2H), 3.55-3.35 (m, 2H), 3.21-3.18 (m, 2H), 3.03-3.00 (m, 1H), 2.75-2.43 (m, 7H), 2.06-1.98 (m, 3H), 1.79-1.15 (m, 25H), 1.02-0.69 (m, 18H).

Step 3: Synthesis of 1-((3aR,5aR,5bR,7aR,9S,11aR,11bR,13aS)-3a-((R)-[1,3'-bipyrrolidine]-1'-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 3-benzyl (1S,3R)-2,2-dimethylcyclobutane-1,3-dicarboxylate

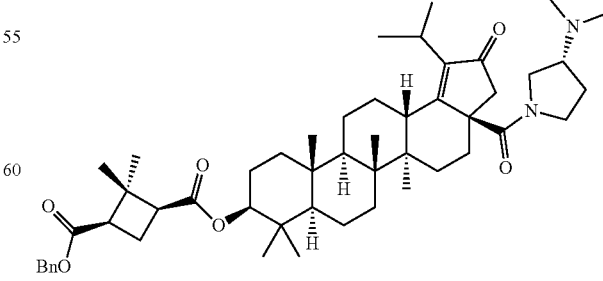

To a stirred solution of (3aR,5aR,5bR,7aR,9S,11aR,11bR,13aS)-3a-((R)-[1,3'-bipyrrolidine]-1'-carbonyl)-9-hydroxy- 1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-2-one (step 2, 1.5 g, 2.53 mmol) and (1S,3R)-3-((benzyloxy)carbonyl)-2,2-dimethylcyclobutane-1-carboxylic acid (prepared as described in WO 2013/160810 A2, 0.972 g, 3.80 mmol) and DMAP (0.06 g, 0.50 mmol) in DCM (30 ml), was slowly added DCC (1.02 g, 5.06 mmol) in DCM (7 ml) at 0° C. and allowed to stir at room temperature for about 12 hours. After completion of the reaction (monitored by TLC), the reaction mixture was diluted with DCM, washed with water, saturated NaHCO$_3$ solution, brine and dried over Na$_2$SO$_4$. The solvent was evaporated and to the resulting solid, was added DCM (10 ml) and stirred for about 1 hour and filtered. The filtrate was concentrated under reduced pressure to afford the title compound (0.9 g, yield: 42%) as a white solid.

Step 4: Synthesis of (1R,3S)-3-((((3aR,5aR,5bR,7aR,9S,11aR,11bR,13aS)-3a-((R)-[1,3'-bipyrrolidine]-1'-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-((3aR,5aR,5bR,7aR,9S,11aR,11bR,13aS)-3a-((R)-[1,3'-bipyrrolidine]-1'-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) 3-benzyl(1S,3R)-2,2-dimethylcyclobutane-1,3-dicarboxylate (step 3, 0.9 g, 1.05 mmol) in THF (15 ml), was added 10% Pd/C (0.05 g) and purged with nitrogen. The reaction mixture was stirred for about 12 hours under H$_2$ atmosphere. After completion of the reaction (monitored by TLC), the reaction mixture was filtered, filtrate was concentrated and purified by silica gel column (elution 5% MeOH in DCM) to afford the desired compound (0.32 g, yield: 41%) as an off white solid. $^1$H NMR (300 MHz, CDCl$_3$): δ 4.48-4.44 (m, 1H), 4.02 (m, 1H), 3.77 (m, 1H), 3.53 (m, 2H), 3.25-3.09 (m, 3H), 2.83-2.59 (m, 7H), 2.43-2.39 (m, 3H), 2.23-1.17 (m, 29H), 1.10-0.79 (m, 22H); ES Mass: 747.53 [M+H]+; HPLC: 91.47%.

Example 5: Preparation of (1R,3S)-3-((((3aR,5aR,5bR,7aR,9S,11aR,11bR,13aS)-3a-((S)-2-(((S)-2-(hydroxymethyl)pyrrolidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethlcyclobutane-1-carboxylic acid Step 1: Synthesis of (3aR,5aR,5bR,7aR,9S,11aR,11bR,13aS)-3a-((S)-2-(((S)-2-((benzyloxy)methyl)pyrrolidin-1-yl)methyl)pyrrolidine-1-carbonyl)-1-isopropyl-5a,5b,8,8,a-pentamethyl-2-oxo-3,3a,4,5,5a,5b,6,7,7a,8,9,10,11,11a,11b,12,13,13a-octadecahydro-2H-cyclopenta[a]chrysen-9-yl acetate

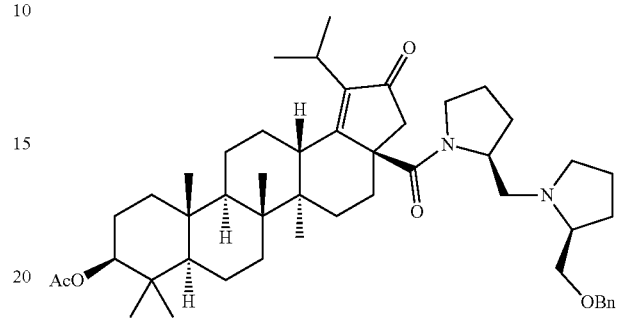

To a stirred solution of (S)-2-((benzyloxy)methyl)-1-(((S)-pyrrolidin-2-yl)methyl)pyrrolidine hydrochloride (Intermediate 6, 1.32 g, 3.84 mmol) in DCM (15 ml) and NEt$_3$ (3.4 ml, 24.5 mmol), was added a solution of (3aR,5aR,5bR,7aR,9S,11aR,11bR,13aS)-3a-(chlorocarbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (Example 1-step 7, 1.7 g, 3.2 mmol) in DCM (15 ml) at 0° C. and allowed to stir at room temperature for about 16 hours. After completion of the reaction (monitored by TLC), the reaction mixture was diluted with DCM, washed with water, brine and dried over Na$_2$SO$_4$. The solvent was evaporated and purified by silica gel column (elution 2% MeOH in DCM) to afford the title compound as an off white solid (1.0 g, yield: 41%). $^1$H NMR (300 MHz, CDCl$_3$): δ 7.32-7.31 (m, 5H), 4.56-4.45 (m, 3H), 4.36 (m, 1H), 3.45-2.97 (m, 6H), 2.77-2.40 (m, 7H), 2.21-1.32 (m, 24H), 1.25-0.79 (m, 26H).

Step 2: Synthesis of (3aR,5aR,5bR,7aR,9S,11aR,11bR,13aS)-3a-((S)-2-(((S)-2-((benzyloxy)methyl)pyrrolidin-1-yl)methyl)pyrrolidine-1-carbonyl)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-2-one

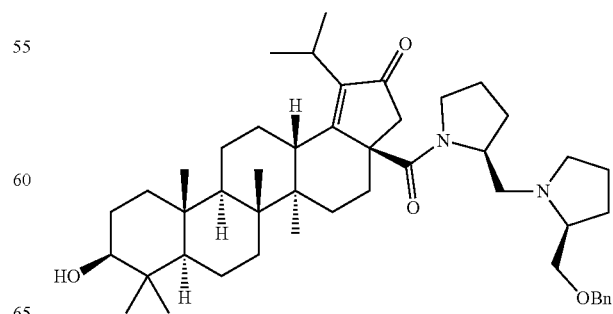

To a stirred solution of (3aR,5aR,5bR,7aR,9S,11aR,11bR, 13aS)-3a-((S)-2-(((S)-2-((benzyloxy)methyl)pyrrolidin-1-yl)methyl)pyrrolidine-1-carbonyl)-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl acetate (step 1, 1.0 g, 1.30 mmol) in MeOH:THF (5 ml: 5 ml), was added 6N NaOH (5 ml) at 0° C. and allowed to stir at room temperature for about 12 hours. After completion of the reaction (monitored by TLC), the reaction mixture was concentrated under reduced pressure. The reaction mixture was diluted with DCM, washed with water, brine and dried over $Na_2SO_4$. The solvent was evaporated and the resulting solid was taken in hexane and stirred for about one hour and filtered to afford the title compound (0.90 g, yield: 96%) as a white solid. $^1H$ NMR (300 MHz, DMSO-$d_6$): δ 7.32-7.26 (m, 5H), 4.44 (ABq, J=12.3 Hz, 2H), 4.27 (d, J=5.1 Hz, 1H), 4.20-4.18 (m, 1H), 3.43-3.34 (m, 2H), 3.17-2.94 (m, 5H), 2.60-1.27 (m, 28H), 1.16-0.64 (m, 26H).

Step 3: Synthesis of 1-benzyl 3-((3aR,5aR,5bR, 7aR,9S,11aR,11bR,13aS)-3a-((S)-2-(((S)-2-((benzyloxy)methyl)pyrrolidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) (1R,3S)-2,2-dimethylcyclobutane-1,3-dicarboxylate

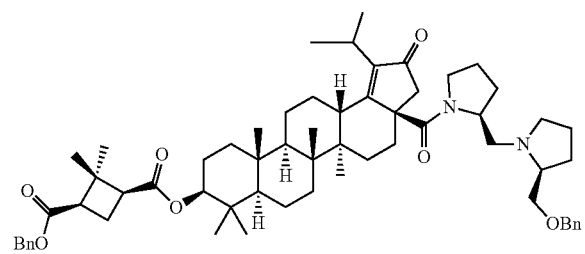

To a stirred solution (3aR,5aR,5bR,7aR,9S,11aR,11bR, 13aS)-3a-((S)-2-(((S)-2-((benzyloxy)methyl)pyrrolidin-1-yl)methyl)pyrrolidine-1-carbonyl)-9-hydroxy-1-isopropyl-5a,5b,8,8,11a-pentamethyl-3,3a,4,5,5a,5b,6,7,7a,8,9,10,11, 11a,11b,12,13,13a-octadecahydro-2H-cyclopenta[a]chrysen-2-one (step 2, 0.90 g, 1.23 mmol) and (1S,3R)-3-((benzyloxy)carbonyl)-2,2-dimethylcyclobutane-1-carboxylic acid (prepared as described in WO 2013/160810 A2, 0.48 g, 1.85 mmol) and DMAP (0.03 g, 0.24 mmol) in DCM (15 ml), was slowly added DCC (0.51 g, 2.46 mmol) in DCM (5 ml) at 0° C. and allowed to stir at room temperature for about 12 hours. After completion of the reaction (monitored by TLC), the reaction mixture was diluted with DCM, washed with water, saturated $NaHCO_3$ solution, brine and dried over $Na_2SO_4$. The solvent was evaporated and to the resulting solid, was added DCM (5 ml) and stirred for about one hour and filtered. The filtrate was concentrated under reduced pressure to afford the title compound (0.9 g, yield: 75%) as a white solid. $^1H$ NMR (300 MHz, $CDCl_3$): δ 7.35-7.32 (m, 10H), 5.12 (ABq, J=12.6 Hz, 2H), 4.52 (s, 2H), 4.47-4.42 (m, 1H), 4.37 (m, 1H), 3.47-1.54 (m, 31H), 1.41-0.78 (m, 39H).

Step 4: Synthesis of (1R,3S)-3-(((((3aR,5aR,5bR, 7aR,9S,11aR,11bR,13aS)-3a-((S)-2-(((S)-2-(hydroxymethyl)pyrrolidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11a,11b,12,13,13a-octadecahydro-2H-cyclopenta[a]chrysen-9-yl)oxy) carbonyl)-2,2-dimethylcyclobutane-1-carboxylic acid To a stirred solution of 1-benzyl 3-((3aR,5aR,5bR,7aR, 9S,11aR,11bR,13aS)-3a-((S)-2-(((S)-2-((benzyloxy)methyl) pyrrolidin-1-yl)methyl)pyrrolidine-1-carbonyl)-1-isopropyl-5a,5b,8,8,11a-pentamethyl-2-oxo-3,3a,4,5,5a,5b,6,7,7a, 8,9,10,11,11a,11b,12,13,13a-octadecahydro-2H-cyclopenta [a]chrysen-9-yl) (1R,3S)-2,2-dimethylcyclobutane-1,3-dicarboxylate (step 3, 0.9 g, 0.928 mmol) in THF (15 ml), was added 10% Pd/C (0.05 g) and purged with nitrogen. The reaction mixture was stirred for about 12 hours under $H_2$ atmosphere. After completion of the reaction (monitored by TLC), the reaction mixture was filtered and filtrate was concentrated and purified by silica gel column (elution 5% MeOH in DCM) to afford the desired compound (0.32 g, yield: 43.7%) as an off white solid. $^1H$ NMR (300 MHz, DMSO-$d_6$): δ 12.20 (brs, 1H), 4.38-4.33 (m, 1H), 4.19 (m, 1H), 3.21-2.76 (m, 8H), 2.58-1.36 (m, 32H), 1.26-0.81 (m, 31H); ES Mass: 791.57 [M+H]+; HPLC: 94.88%.

Example 6: Preparation of (1R,3S)-3-((((3aR,5aR, 5bR,7aR,9S,11aR,11bR,13aS)-3a-((S)-2-((3,3-difluoropyrrolidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

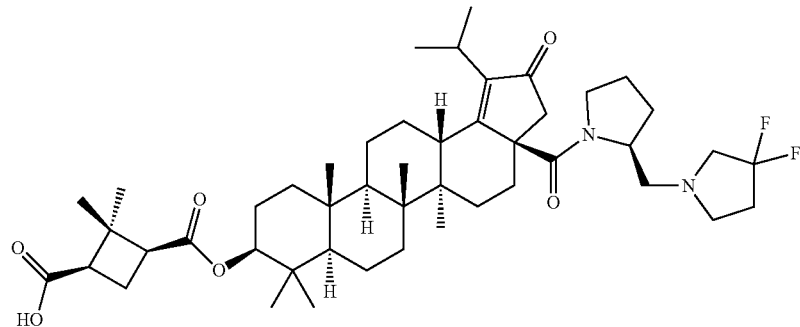

Step 1: Synthesis of (3aR,5aR,5bR,7aR,9S,11aR,11bR,13aS)-3a-((S)-2-((3,3-difluoropyrrolidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate

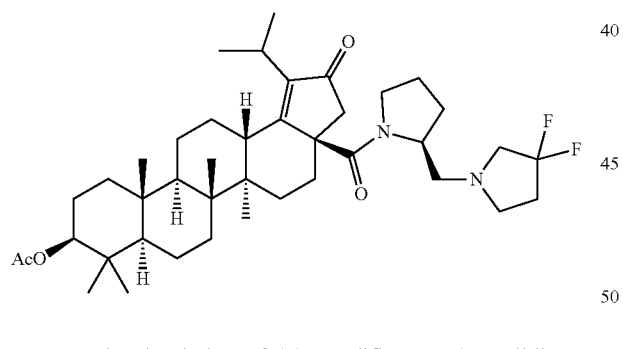

To a stirred solution of (S)-3,3-difluoro-1-(pyrrolidin-2-ylmethyl)pyrrolidine (Intermediate 8, 0.57 g, 3.0 mmol) in DCM (15 ml) and NEt$_3$ (3.2 ml, 23.8 mmol), was added a solution of (3aR,5aR,5bR,7aR,9S,11aR,11bR,13aS)-3a-(chlorocarbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (Example 1-step 7, 1.6 g, 3.01 mmol) in DCM (20 ml) at 0° C. and allowed to stir at room temperature for about 16 hours. After completion of the reaction (monitored by TLC), the reaction mixture was diluted with DCM, washed with water, brine and dried over Na$_2$SO$_4$. The solvent was evaporated and purified by silica gel column (elution 2% MeOH/DCM) to afford the title compound (1.0 g, yield: 50%) as an off white solid. $^1$H NMR (300 MHz, CDCl$_3$): δ 4.51-4.45 (m, 1H), 4.13 (m, 1H), 3.45 (m, 1H), 3.21-2.15 (m, 9H), 2.05 (s, 3H), 1.95-1.03 (m, 32H), 0.97-0.84 (m, 15H).

Step 2: Synthesis of (3aR,5aR,5bR,7aR,9S,11aR,11bR,13aS)-3a-((S)-2-((3,3-difluoropyrrolidin-1-yl)methyl)pyrrolidine-1-carbonyl)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-2-one To a stirred solution of (3aR,5aR,5bR,7aR,9S,11aR,1bR,1aS)-3a-((S)-2-((3,3-difluoropyrrolidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (step 1, 1.0 g, 1.46 mmol) in MeOH:THF (5 ml: 5 ml), was added 4N NaOH (5 ml) at 0° C. and allowed to stir at room temperature for about 12 hours. After completion of the reaction (monitored by TLC), the reaction mixture was concentrated under reduced pressure. The reaction mixture was diluted with DCM, washed with water, brine and dried over Na$_2$SO$_4$. The solvent was evaporated and the resulting solid was taken in hexane and stirred for about one hour and filtered to afford the title compound (0.8 g, yield: 88%) as a white solid. ¹H NMR (300 MHz, CDCl₃): δ 4.05-4.02 (m, 1H), 3.50-3.45 (m, 2H), 3.28-2.30 (m, 9H), 1.95-1.05 (m, 31H), 1.03-0.69 (m, 16H).

Step 3: Synthesis of 1-benzyl 3-((3aR,5aR,5bR, 7aR,9S,11aR,11bR,13aS)-3a-((S)-2-((3,3-difluoropyrrolidin-1-yl)methyl)pyrrolidine-1-carbonyl)-1-isopropyl-5a,5b,8,8,11a-pentamethyl-2-oxo-3,3a,4,5,5a, 5b,6,7,7a,8,9,10,11,11a,11b,12,13,13a-octadecahydro-2H-cyclopenta[a]chrysen-9-yl) (1R, 3S)-2,2-dimethylcyclobutane-1,3-dicarboxylate

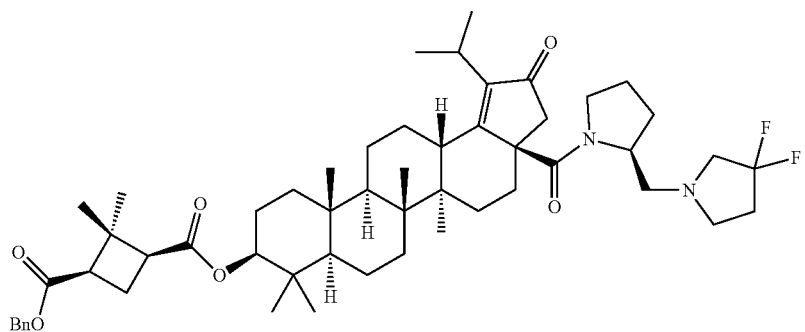

To a stirred solution of (3aR,5aR,5bR,7aR,9S,11aR,11bR, 13aS)-3a-((S)-2-((3,3-difluoropyrrolidin-1-yl)methyl)pyrrolidine-1-carbonyl)-9-hydroxy-1-isopropyl-5a,5b,8,8,11a-pentamethyl-3,3a,4,5,5a,5b,6,7,7a,8,9,10,11,11a,11b,12,13, 13a-octadecahydro-2H-cyclopenta[a]chrysen-2-one (step 2, 0.8 g, 1.24 mmol) and (1S,3R)-3-((benzyloxy)carbonyl)-2, 2-dimethyl cyclobutane-1-carboxylic acid (prepared as described in WO 2013/160810 A2, 0.488 g, 1.86 mmol) and DMAP (0.03 g, 0.24 mmol) in DCM (15 ml), was slowly added DCC (0.51 g, 2.48 mmol) in DCM (8 ml) at 0° C. and allowed to stir at room temperature for about 12 hours. After completion of the reaction (monitored by TLC), the reaction mixture was diluted with DCM, washed with water, saturated NaHCO₃ solution, brine and dried over Na₂SO₄. The solvent was evaporated and to the resulting solid, was added DCM (5 ml) and stirred for about one hour and filtered. The filtrate was concentrated under reduced pressure to afford the title compound (0.6 g, yield: 54%) as a white solid. ¹H NMR (300 MHz, CDCl₃): δ 7.35 (m, 5H), 5.13 (ABq, J=12.3 Hz, 2H), 4.34-4.32 (m, 1H), 4.23-4.20 (m, 1H), 3.49-3.44 (m, 1H), 3.19-1.67 (m, 30H), 1.50-1.03 (m, 14H), 0.97-0.78 (m, 22H).

Step 4: Synthesis of (1R,3S)-3-((((3aR,5aR,5bR, 7aR,9S,11aR,11bR,13aS)-3a-((S)-2-((3,3-difluoropyrrolidin-1-yl)methyl)pyrrolidine-1-carbonyl)-1-isopropyl-5a,5b,8,8,11a-pentamethyl-2-oxo-3,3a,4,5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid To a stirred solution of 1-benzyl 3-((3aR,5aR,5bR,7aR, 9S,11aR,11bR,13aS)-3a-((S)-2-((3,3-difluoropyrrolidin-1-yl)methyl)pyrrolidine-1-carbonyl)-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl) (1R,3S)-2,2-dimethylcyclobutane-1,3-dicarboxylate (step 3, 0.6 g, 0.67 mmol) in THF (12 ml), was added 10% Pd/C (0.1 g) and purged with nitrogen. The reaction mixture was stirred for about 12 hours under H₂ atmosphere. After completion of the reaction (monitored by TLC), the reaction mixture was filtered and filtrate was concentrated and purified by silica gel column (elution 2% MeOH in DCM) to afford the desired compound as a white solid (0.21 g, Yield: 39%). ¹H NMR (300 MHz, DMSO-d₆): δ 12.16 (s, 1H), 4.38-4.33 (m, 1H), 4.18 (m, 1H), 3.19-2.76 (m, 9H), 2.31-1.36 (m, 27H), 1.26-0.81 (m, 31H). ES Mass: 797.49 [M+H]⁺. HPLC: 93.0%.

Example 7: Preparation of (1R,3S)-3-((((3aR,5aR, 5bR,7aR,9S,11aR,11bR,13aS)-3a-((S)-2-((4,4-difluoropiperidin-1-yl)methyl)pyrrolidine-1-carbonyl)-1-isopropyl-5a,5b,8,8,11a-pentamethyl-2-oxo-3,3a,4,5,5a,5b,6,7,7a,89,10,11,11a,11b,12,13,13a-octadecahydro-2H-cyclopenta[a]chrysen-9-yl)oxy)carbonyl)-2,2-dimethylcyclobutane-1-carboxylic acid

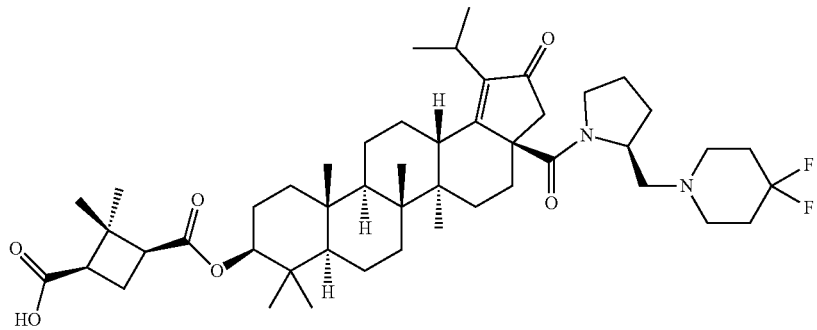

Step 1: Synthesis of (3aR,5aR,5bR,7aR,9S,11aR,11bR,13aS)-3a-((S)-2-((4,4-difluoropiperidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate

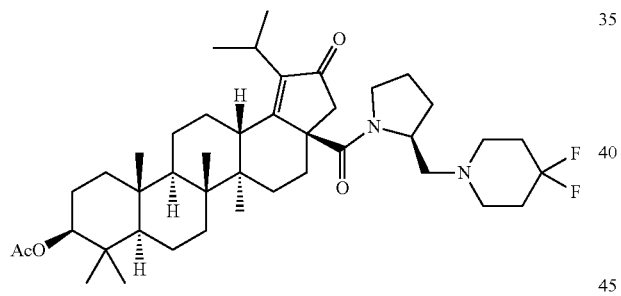

To a stirred solution of (S)-4,4-difluoro-1-(pyrrolidin-2-ylmethyl)piperidine (Intermediate 9, 0.21 g, 1.0 mmol) in DCM (5 ml) and NEt$_3$ (1.0 ml, 7.44 mmol), was added a solution of (3aR,5aR,5bR,7aR,9S,11aR,11bR,13aS)-3a-(chlorocarbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (Example 1-step 7, 0.46 g, 0.87 mmol) in DCM (8 ml) at 0° C. and allowed to stir at room temperature for about 16 hours. After completion of the reaction (monitored by TLC), the reaction mixture was diluted with DCM, washed with water, brine and dried over Na$_2$SO$_4$. The solvent was evaporated and purified by silica gel column (elution 2% MeOH/DCM) to afford the title compound (0.4 g, yield: 67%) as an off white solid. $^1$H NMR (300 MHz, CDCl$_3$): δ 4.51-4.45 (m, 1H), 4.23-4.16 (m, 1H), 3.23-3.12 (m, 1H), 2.78-2.07 (m, 10H), 2.05 (s, 3H), 2.01-1.07 (m, 27H), 1.03-0.84 (m, 21H); ES Mass: 699.44 [M+H]$^+$.

Step 2: Synthesis of (3aR,5aR,5bR,7aR,9S,11aR,11bR,13aS)-3a-((S)-2-((4,4-difluoropiperidin-1-yl)methyl)pyrrolidine-1-carbonyl)-9-hydroxy-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-2-one

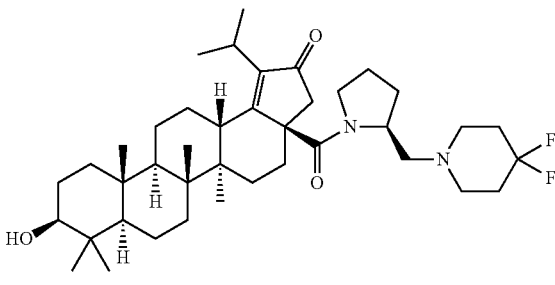

To a stirred solution of (3aR,5aR,5bR,7aR,9S,11aR,1bR,1aS)-3a-((S)-2-((4,4-difluoropiperidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (step 1, 0.4 g, 0.57 mmol) in MeOH:THF (4 ml: 4 ml), was added 4N NaOH (4 ml) at 0° C. and allowed to stir at room temperature for about 12 hours. After completion of the reaction (monitored by TLC), the reaction mixture was concentrated under reduced pressure. The reaction mixture was diluted with DCM, washed with water, brine and dried over Na$_2$SO$_4$. The solvent was evaporated and the resulting solid was taken in hexane and stirred for about one hour and filtered to afford the title compound (0.35 g, yield: 95%) as a white solid. $^1$H NMR (300 MHz, CDCl$_3$): δ 4.36-4.34 (m, 1H), 3.56-3.53 (m, 1H), 3.23-2.54 (m, 8H), 2.21-1.83 (m, 7H), 1.47-1.07 (m, 25H), 1.03-0.69 (m, 19H); ES Mass: 657.41 [M+H]$^+$.

Step 3: Synthesis of 1-benzyl 3-((3aR,5aR,5bR, 7aR,9S,11aR,11bR,13aS)-3a-((S)-2-((4,4-difluoropiperidin-1-yl)methyl)pyrrolidine-1-carbonyl)-1-isopropyl-5a,5b,8,8,11a-pentamethyl-2-oxo-3,3a,4,5,5a, 5b,6,7,7a,8,9,10,11,11a,11b,12,13,13a-octadecahydro-2H-cyclopenta[a]chrysen-9-yl) (1R, 3S)-2,2-dimethylcyclobutane-1,3-dicarboxylate

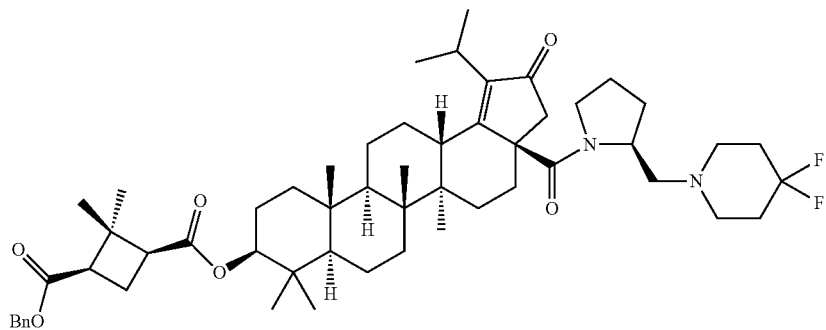

To a stirred solution of (3aR,5aR,5bR,7aR,9S,11aR,1bR, 13aS)-3a-((S)-2-((4,4-difluoropiperidin-1-yl)methyl)pyrrolidine-1-carbonyl)-9-hydroxy-1-isopropyl-5a,5b,8,8,11a-pentamethyl-3,3a,4,5,5a,5b,6,7,7a,8,9,10,11,11a,11b,12,13, 13a-octadecahydro-2H-cyclopenta[a]chrysen-2-one (step 2, 0.35 g, 0.53 mmol) and (1S,3R)-3-((benzyloxy)carbonyl)-2,2-dimethylcyclobutane-1-carboxylic acid (prepared as described in WO 2013/160810 A2, 0.21 g, 0.8 mmol) and DMAP (0.013 g, 0.11 mmol) in DCM (8 ml), was slowly added DCC (0.22 g, 1.1 mmol) in DCM (4 ml) at 0° C. and allowed to stir at room temperature for about 12 hours. After completion of the reaction (monitored by TLC), the reaction mixture was diluted with DCM, washed with water, saturated NaHCO$_3$ solution, brine and dried over Na$_2$SO$_4$. The solvent was evaporated and to the resulting solid, was added DCM (3 ml) and stirred for about one hour and filtered. The filtrate was concentrated under reduced pressure to afford the title compound (0.25 g, yield: 52%) as a white solid. $^1$H NMR (300 MHz, CDCl$_3$): δ 7.35 (m, 5H), 5.13 (ABq, J=12.3 Hz, 2H), 4.47-4.42 (m, 1H), 4.23-4.20 (m, 1H), 3.44 (m, 1H), 3.21-1.59 (m, 30H), 1.47-1.08 (m, 16H), 1.03-0.82 (m, 22H); ES Mass: 901.52 [M+H]$^+$.

Step 4: Synthesis of (1R,3S)-3-((((3aR,5aR,5bR, 7aR,9S,11aR,11bR,13aS)-3a-((S)-2-((4,4-difluoropiperidin-1-yl)methyl)pyrrolidine-1-carbonyl)-1-isopropyl-5a,5b,8,8,11a-pentamethyl-2-oxo-3,3a,4,5,5a, 6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR, 9S,11aR,11bR,13aS)-3a-((S)-2-((4,4-difluoropiperidin-1-yl)methyl)pyrrolidine-1-carbonyl)-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl) (1R,3S)-2,2-dimethylcyclobutane-1,3-dicarboxylate (step 3, 0.25 g, 0.27 mmol) in THF (7 ml), was added 10% Pd/C (0.05 g) and purged with nitrogen. The reaction mixture was stirred for about 12 hours under H$_2$ atmosphere. After completion of the reaction (monitored by TLC), the reaction mixture was filtered and filtrate was concentrated and purified by silica gel column (elution 2% MeOH in DCM) to afford the desired compound (0.08 g, yield: 36%) as a white solid. $^1$H NMR (300 MHz, DMSO-d$_6$): δ 12.11 (brs, 1H), 4.38-4.33 (m, 1H), 4.20 (m, 1H), 3.18-2.62 (m, 9H), 2.44-1.36 (m, 29H), 1.26-0.81 (m, 31H); ES Mass: 811.52 [M+H]+; HPLC: 91.0%.

Example 8: Preparation of (1R,3S)-3-((((3aR,5aR, 5bR,7aR,9S,11aR,11bR,13aS)-1-isopropyl-5a,5b,8, 8,11a-pentamethyl-2-oxo-3a-((2-(5-phenyl-1H-imidazol-2-yl)propan-2-yl)carbamoyl)-3,3a,4,5,5a,5b,6, 7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

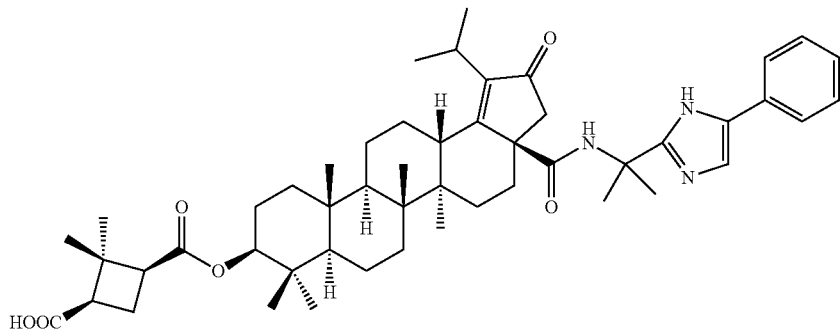

Step 1: Synthesis of (3aR,5aR,5bR,7aR,9S,11aR, 11bR,13aS)-1-isopropyl-5a,5b,8,8,11a-pentamethyl-2-oxo-3a-((2-(5-phenyl-1H-imidazol-2-yl)propan-2-yl)carbamoyl)-3,3a,4,5,5a,5b,6,7,7a,8,9,10,11,11a, 11b,12,13,13a-octadecahydro-2H-cyclopenta[a] chrysen-9-yl Step 2: Synthesis of (3aR,5aR,5bR,7aR,9S,11aR, 11bR,13aS)-9-hydroxy-1-isopropyl-5a,5b,8,8,11a-pentamethyl-2-oxo-N-(2-(5-phenyl-1H-imidazol-2-yl)propan-2-yl)-2,3,4,5,5a,5 b,6,7,7a,8,9,10,11,11a, 11b,12,13,13a-octadecahydro-3aH-cyclopenta[a] chrysene-3a-carboxamide

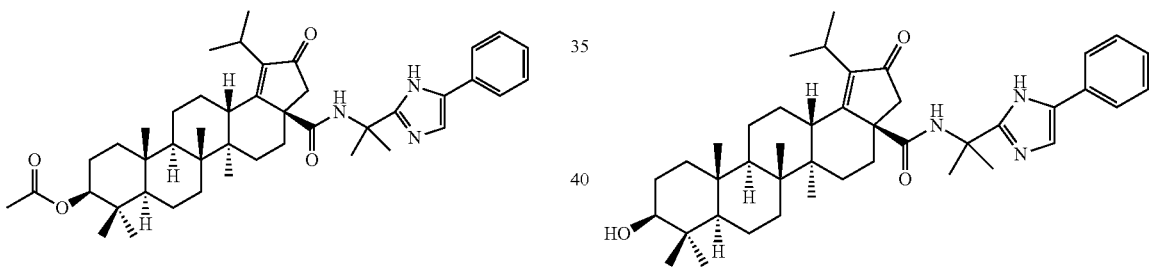

To a stirred solution of 2-(5-phenyl-1H-imidazol-2-yl) propan-2-amine (Intermediate 1, 0.568 g, 2.826 mmol, 1.5 eq) in DCM (10 ml) at 0° C. under nitrogen atmosphere was added triethylamine (1.3 ml, 9.413 mmol, 5.0 eq) and (3aR,5aR,5bR,7aR,9S,11aR,11bR,13aS)-3a-(chlorocarbonyl)-1-isopropyl-5a,5b,8,8,11a-pentamethyl-2-oxo-3,3a,4,5, 5a,5b,6,7,7a,8,9,10,11,11a,11b,12,13,13a-octadecahydro-2H-cyclopenta[a]chrysen-9-yl acetate (Example 1-step 7, 1.0 g, 1.882 mmol, 1.0 eq) dissolved in DCM (10 ml). The reaction mixture was removed from the ice bath and was stirred at room temperature for overnight. TLC indicated starting material was consumed and the desired product was observed. The reaction mixture was diluted with water (100 ml) and extracted with DCM (3×50 ml). The combined organic extracts were washed with 0.5N HCl (10 ml), water (15 ml) and brine solution (15 ml). The organic layer was dried over sodium sulfate, filtered and evaporated under reduced pressure. The residue was purified by silicagel column chromatography by using 0-2% methanol in dichloromethane gradient. The fractions containing the expected product were combined and concentrated under reduced pressure to obtain the desired product (1.0 g, yield: 76.92%) as a yellow solid. ESI-MS: m/z 696.28 (M+H)⁺.

To a stirred solution of (3aR,5aR,5bR,7aR,9S,11aR,11bR, 13aS)-1-isopropyl-5a,5b,8,8,11a-pentamethyl-2-oxo-3a-((2-(5-phenyl-1H-imidazol-2-yl)propan-2-yl)carbamoyl)-3, 3a,4,5,5a,5b,6,7,7a,8,9,10,11,11a,11b,12,13,13a-octadecahydro-2H-cyclopenta[a]chrysen-9-yl acetate (step 1, 1.0 g, 1.436 mmol, 1.0 eq) in MeOH (10 ml), THF (5 ml) and water (2.5 ml) (4:2:1 ratio) at 0° C. was added NaOH (0.574 g, 14.36 mmol, 10.0 eq). The reaction mixture was removed from the ice bath and was stirred at room temperature for overnight. TLC indicated starting material was consumed and the desired product was observed. The reaction mixture was evaporated under reduced pressure, diluted with water (30 ml) and extracted with DCM (3×50 ml). The combined organic extracts were washed with water (30 ml) and brine solution (30 ml). The organic layer was dried over sodium sulfate, filtered and evaporated under reduced pressure. The residue was purified by silicagel column chromatography by using 0-4% methanol in dichloromethane gradient. The fractions containing the expected product were combined and concentrated under reduced pressure to obtain the desired product (0.400 g, yield: 42.59%) as an off-white solid. 1H NMR (300 MHz, CDCl₃): δ ppm 7.73-7.68 (m, 1H), 7.56-7.51 (m, 1H), 7.41-7.32 (m, 3H), 7.22-7.19 (s, 1H), 3.29-3.15 (m, 2H), 2.65-2.30 (m, 2H), 2.24-2.12 (m, 1H), 2.12-1.85 (m, 4H), 1.83-1.05 (m, 25H), 1.02-0.65 (m, 16H); ESI-MS: m/z 654.14 (M+H)$^+$.

Step 3: Synthesis of 1-benzyl 3-((3aR,5aR,5bR, 7aR,9S,11aR,11bR,13aS)-1-isopropyl-5a,5b,8,8,11a-pentamethyl-2-oxo-3a-((2-(5-phenyl-1H-imidazol-2-yl)propan-2-yl)carbamoyl)-3,3a,4,5,5a,5b,6,7,7a,8,9,10,11,11a,11b,12,13,13a-octadecahydro-2H-cyclopenta[a]chrysen-9-yl)(1R,3S)-2,2-dimethylcyclobutane-1,3-dicarboxylate

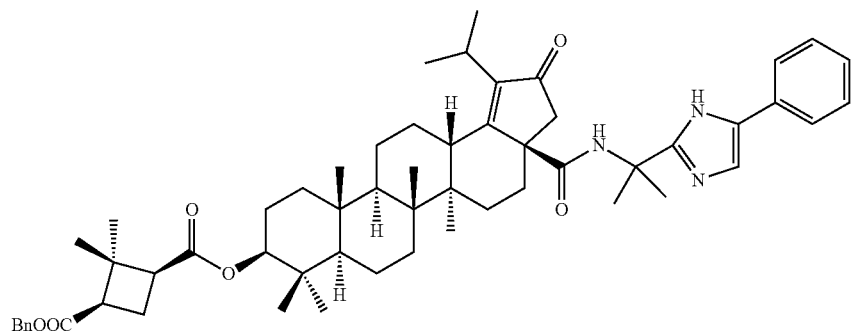

To a stirred solution of (3aR,5aR,5bR,7aR,9S,11aR,11bR, 13aS)-9-hydroxy-1-isopropyl-5a,5b,8,8,11a-pentamethyl-2-oxo-N-(2-(5-phenyl-1H-imidazol-2-yl)propan-2-yl)-2,3,4,5,5a,5b,6,7,7a,8,9,10,11,11a,11b,12,13,13a-octadecahydro-3aH-cyclopenta[a]chrysene-3a-carboxamide (step 2, 0.400 g, 0.611 mmol, 1.0 eq) in DCM (10 ml) at 0° C. under nitrogen atmosphere was added (1S,3R)-3-((benzyloxy)carbonyl)-2,2-dimethylcyclobutane-1-carboxylic acid (prepared as described in WO 2011/007230 A2, 0.240 g, 0.917 mmol, 1.5 eq), EDCI (0.474 g, 3.058 mmol, 5.0 eq) and DMAP (0.224 g, 1.834 mmol, 3.0 eq). The mixture was removed from the ice bath and was stirred at room temperature for overnight. TLC indicated starting material was consumed and the desired product was observed. The reaction mixture was diluted with water (20 ml) and extracted with DCM (3×20 ml). The combined organic extracts were washed with water (20 ml) and brine solution (20 ml). The organic layer was dried over sodium sulfate, filtered and evaporated under reduced pressure. The residue was purified by silicagel column chromatography by using 0-3% methanol in dichloromethane gradient. The fractions containing the expected product were combined and concentrated under reduced pressure to give the desired product (0.250 g, yield: 45.53%) as an off-white solid. 1H NMR (300 MHz, CDCl$_3$): δ ppm 10.26 (s, 0.5H), 7.78-7.70 (m, 2H), 7.56-7.40 (m, 2H), 7.40-7.20 (m, 7H), 5.14, 5.09 (ABq, 2H), 4.48-4.40 (m, 1H), 3.30-3.20 (m, 1H), 2.87-2.72 (m, 2H), 2.70-2.50 (m, 3H), 2.60-2.50 (m, 1H), 2.22-2.10 (m, 1H), 2.10-1.0 (m, 26H), 1.80 (s, 3H), 1.78 (s, 3H), 1.0-0.74 (m, 19H); ESI-MS: m/z 898.35 (M+H)$^+$.

Step 4: Synthesis of (1R,3S)-3-((((3aR,5aR,5bR, 7aR,9S,11aR,11bR,13aS)-1-isopropyl-5a,5b,8,8,11a-pentamethyl-2-oxo-3a-((2-(5-phenyl-1H-imidazol-2-yl)propan-2-yl)carbamoyl)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR, 9S,11aR,11bR,13aS)-1-isopropyl-5a,5b,8,8,11a-pentamethyl-2-oxo-3a-((2-(5-phenyl-1H-imidazol-2-yl)propan-2-yl)carbamoyl)-3,3a,4,5,5a,5b,6,7,7a,8,9,10,11,11a,11b,12, 13,13a-octadecahydro-2H-cyclopenta[a]chrysen-9-yl) (1R, 3S)-2,2-dimethylcyclobutane-1,3-dicarboxylate (step 3, 0.250 g, 0.278 mmol, 1.0 eq) in MeOH (2.5 ml) and THF (2.5 ml) was added aqueous 2.5 N KOH solution (0.83 ml, 2.087 mmol, 7.5 eq). The reaction mixture was stirred at room temperature for overnight. TLC indicated starting material was consumed and the desired product was observed. The reaction mixture was evaporated under reduced pressure, diluted with water (10 ml), cooled to 0° C., acidified with 1 N HCl to pH-5 and extracted with DCM (3×40 ml).

The combined organic extracts were washed with water (40 ml), dried over sodium sulfate, filtered and evaporated under reduced pressure. The residue was purified by silicagel column chromatography by using 0-5% MeOH in DCM gradient. The fractions containing the expected product were combined and concentrated under reduced pressure to give the desired product (0.035 g, yield: 15.5%) as an off-white solid. 1H NMR (300 MHz, CDCl$_3$): δ ppm 10.3 (s, 1H), 7.80-7.60 (m, 2H), 7.40-7.30 (m, 2H), 7.22-7.18 (m, 2H), 6.09 (brs, 1H), 4.50-4.40 (m, 1H), 3.32-3.20 (m, 1H), 2.88-2.73 (m, 2H), 2.65-2.40 (m, 4H), 2.22-1.87 (m, 8H), 1.79 (s, 3H), 1.77 (s, 3H), 1.73-1.18 (m, 18H), 1.10-0.70 (m, 20H); ESI-MS: m/z 808.5 (M+H)$^+$; HPLC: 97.7%.

Example 9: Preparation of (1R,3S)-3-(((((3aR,5aR,5bR,7aR,9S,11aR,11bR,13aS)-3a-((S)-2-(2-hydroxypropan-2-yl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

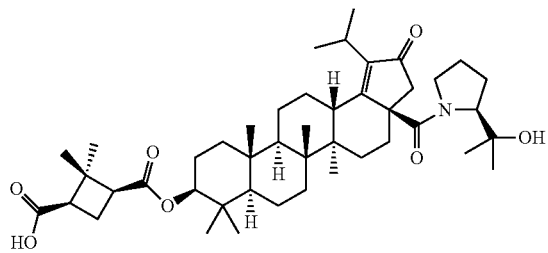

Step 1: Synthesis of (3aR,5aR,5bR,7aR,9S,1aR,11bR,13aS)-3a-((S)-2-(2-hydroxypropan-2-yl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate

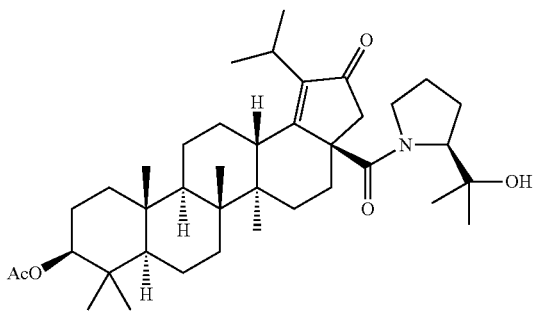

To a stirred solution of (S)-2-(pyrrolidin-2-yl)propan-2-ol hydrochloride (Intermediate 5, 0.5 g, 3.0 mmol) in DCM (10 ml) and NEt$_3$ (2.5 ml, 18.6 mmol), was added a solution of (3aR,5aR,5bR,7aR,9S,11aR,11bR,13aS)-3a-(chlorocarbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (Example 1-step 7, 1.35 g, 2.53 mmol) in DCM (15 ml) at 0° C. and allowed to stir at room temperature for about 16 hours. After completion of the reaction (monitored by TLC), the reaction mixture was diluted with DCM and washed with water, brine and dried over Na$_2$SO$_4$, and the solvent was evaporated and purified by silica gel column (elution 30% EtOAc/hexane) to afford the title compound (1.4 g, yield: 88%) as an off white solid. $^1$H NMR (300 MHz, CDCl$_3$): δ 5.48 (s, 1H), 4.50-4.38 (m, 2H), 3.39-3.34 (m, 1H), 3.26-3.17 (m, 1H), 3.02-2.97 (m, 1H), 2.82-2.71 (m, 2H), 2.42-1.02 (m, 40H), 0.98-0.79 (m, 13H).

Step 2: Synthesis of (3aR,5aR,5bR,7aR,9S,11aR,11bR,13aS)-9-hydroxy-3a-((S)-2-(2-hydroxy propan-2-yl)pyrrolidine-1-carbonyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-2-one

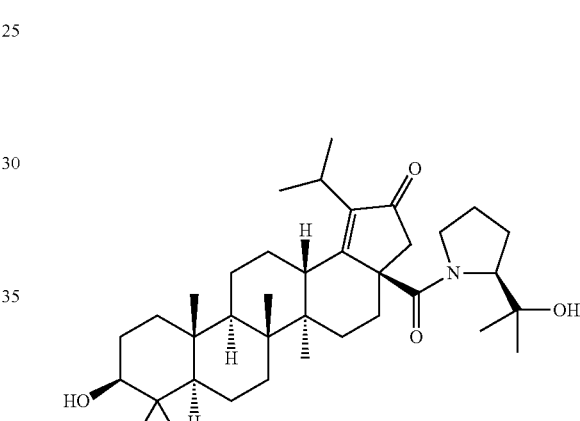

To a stirred solution of (3aR,5aR,5bR,7aR,9S,11aR,11bR,13aS)-3a-((S)-2-(2-hydroxy propan-2-yl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (step 1, 1.40 g, 2.24 mmol) in MeOH:THF (7 ml: 7 ml), was added 4N NaOH (10 ml) at 0° C. and allowed to stir at room temperature for about 12 hours. After completion of the reaction (monitored by TLC), the reaction mixture was concentrated under reduced pressure. The reaction mixture was diluted with DCM and washed with water, brine and dried over Na$_2$SO$_4$. The solvent was evaporated and the resulting solid was taken in hexane and stirred for one hour and filtered to afford the title compound as a white solid (1.3 g, yield: 99%). $^1$H NMR (300 MHz, CDCl$_3$): δ 5.48 (s, 1H), 4.43-4.38 (m, 1H), 3.40-3.34 (m, 1H), 3.26-3.16 (m, 2H), 3.02-2.93 (m, 1H), 2.80-2.73 (m, 2H), 2.42-1.16 (m, 29H), 1.10-0.688 (m, 21H).

Step 3: Synthesis of 1-benzyl 3-((3aR,5aR,5bR,
7aR,9S,11aR,11bR,13aS)-3a-((S)-2-(2-hydroxypro-
pan-2-yl)pyrrolidine-1-carbonyl)-1-isopropyl-5a,5b,
8,8,11a-pentamethyl-2-oxo-3,3a,4,5,5a,5b,6,7,7a,8,9,
10,11,11a,11b,12,13,13a-octadecahydro-2H-
cyclopenta[a]chrysen-9-yl) (1R,3S)-2,2-
dimethylcyclobutane-1,3-dicarboxylate

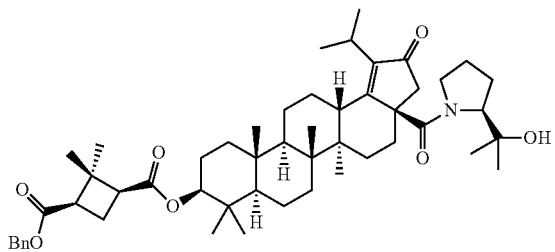

To a stirred solution of (3aR,5aR,5bR,7aR,9S,11aR,11bR,13aS)-9-hydroxy-3a-((S)-2-(2-hydroxypropan-2-yl)pyrrolidine-1-carbonyl)-1-isopropyl-5a,5b,8,8,11a-pentamethyl-3,3a,4,5,5a,5b,6,7,7a,8,9,10,11,11a,11b,12,13,13a-octadecahydro-2H-cyclopenta[a]chrysen-2-one (1.3 g, 2.22 mmol) and (1S,3R)-3-((benzyloxy)carbonyl)-2,2-dimethylcyclobutane-1-carboxylic acid (prepared as described in WO 2011/007230 A2, 0.87 g, 3.34 mmol) and DMAP (0.054 g, 0.44 mmol) in DCM (20 ml), was slowly added DCC (0.92 g, 4.4 mmol) in DCM (10 ml) at 0° C. and allowed to stir at room temperature for about 12 hours. After completion of the reaction (monitored by TLC), the reaction mixture was diluted with DCM and washed with water, saturated $NaHCO_3$ solution, brine and dried over $Na_2SO_4$. The solvent was evaporated and to the resulting solid, was added DCM (15 ml) and stirred for one hour and filtered. The filtrate was concentrated under reduced pressure to afford the title compound (1.1 g, yield: 60%) as a white solid. $^1$H NMR (300 MHz, CDCl$_3$): δ 7.35 (m, 5H), 5.51 (s, 1H), 5.13 (ABq, J=12.3 Hz, 2H), 4.46-4.38 (m, 2H), 3.40-3.34 (m, 1H), 3.26-3.17 (m, 1H), 3.04-2.97 (m, 1H), 2.85-2.58 (m, 4H), 2.42-1.05 (m, 42H), 0.98-0.77 (m, 16H).

Step 4: Synthesis of (1R,3S)-3-((((3aR,5aR,5bR,
7aR,9S,11aR,11bR,13aS)-3a-((S)-2-(2-hydroxypro-
pan-2-yl)pyrrolidine-1-carbonyl)-1-isopropyl-5a,5b,
8,8,11a-pentamethyl-2-oxo-3,3a,4,5,5a,5b,6,7,7a,8,9,
10,11,11a,11b,12,13,13a-octadecahydro-2H-
cyclopenta[a]chrysen-9-yl)oxy)carbonyl)-2,2-
dimethylcyclobutane-1-carboxylic acid To a stirred solution of 1-benzyl 3-((3aR,5aR,5bR,7aR,9S,11aR,11bR,13aS)-3a-((S)-2-(2-hydroxypropan-2-yl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 3, 1.1 g, 1.33 mmol) in THF (15 ml), was added 10% Pd/C (0.2 g) and purged with nitrogen. The reaction mixture was stirred for about 12 hours under $H_2$ atmosphere. After completion of the reaction (monitored by TLC), the reaction mixture was filtered and filtrate was concentrated and purified by silica gel column (elution 2% MeOH in DCM) to afford the desired compound as a white solid (0.33 g, yield: 33.7%). $^1$H NMR (300 MHz, DMSO-d$_6$): δ 12.15 (s, 1H), 4.98 (s, 1H), 4.38-4.33 (m, 1H), 4.23-4.19 (m, 1H), 3.23-3.15 (m, 2H), 3.02-2.97 (m, 1H), 2.83-1.37 (m, 24H), 1.26-0.81 (m, 38H); ES Mass: 736.23 [M+H]$^+$. HPLC: 97.65%.

Example 10: Preparation of (1R,3S)-3-((((3aR,5aR,
5bR,7aR,9S,11aR,11bR,13aS)-3a-((S)-2-((4-fluo-
ropiperidin-1-yl)methyl)pyrrolidine-1-carbonyl)-1-
isopropyl-5a,5b,8,8,11a-pentamethyl-2-oxo-3,3a,4,5,
5a,5b,6,7,7a,8,9,10,11,11a,11b,12,13,13a-
octadecahydro-2H-cyclopenta[a]chrysen-9-yl)oxy)
carbonyl)-2,2-dimethylcyclobutane-1-carboxylic
acid

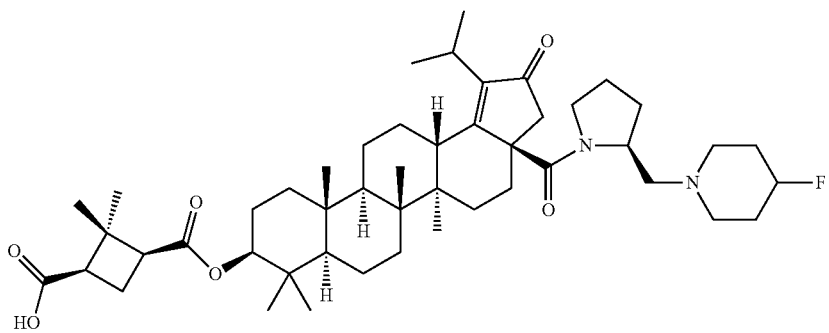

Step 1: Synthesis of (3aR,5aR,5bR,7aR,9S,11aR,
11bR,13aS)-3a-((S)-2-((4-fluoropiperidin-1-yl)
methyl)pyrrolidine-1-carbonyl)-1-isopropyl-5a,5b,8,
8,11a-pentamethyl-2-oxo-3,3a,4,5,5a,5b,6,7,7a,8,9,
10,11,11a,11b,12,13,13a-octadecahydro-2H-
cyclopenta[a]chrysen-9-yl acetate Step 2: Synthesis of (3aR,5aR,5bR,7aR,9S,11aR,
11bR,13aS)-3a-((S)-2-((4-fluoropiperidin-1-yl)
methyl)pyrrolidine-1-carbonyl)-9-hydroxy-1-isopro-
pyl-5a,5b,8,8,11a-pentamethyl-3,3a,4,5,5a,5b,6,7,7a,
8,9,10,11,11a,11b,12,13,13a-octadecahydro-2H-
cyclopenta[a]chrysen-2-one

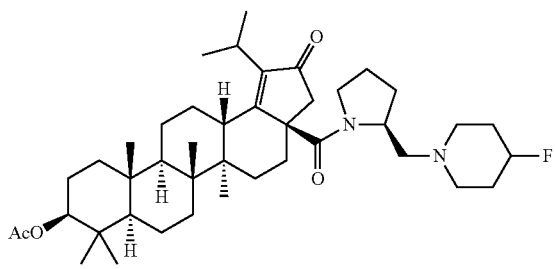

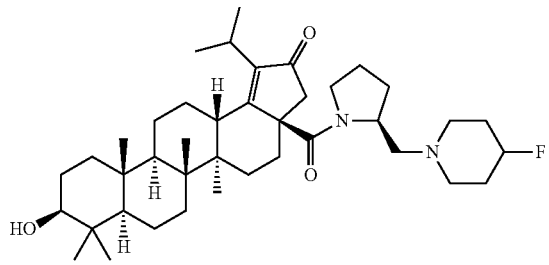

To a stirred solution of (3aR,5aR,5bR,7aR,9S,11aR,11bR, 13aS)-3a-((S)-2-((4-fluoro piperidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl acetate (step 1, 1.3 g, 1.91 mmol) in MeOH:THF (6 ml: 6 ml), was added 6N NaOH (7 ml) at 0° C. and allowed to stir at room temperature for about 12 hours. After completion of the reaction (monitored by TLC), the reaction mixture was concentrated under reduced pressure. The reaction mixture was diluted with DCM and washed with water, brine and dried over $Na_2SO_4$. The solvent was evaporated and the resulting solid was taken in hexane and stirred for about 1 hour and filtered to afford the title compound (1.1 g, yield: 91.6%) as a white solid.

To a stirred solution of (S)-4-fluoro-1-(pyrrolidin-2-ylmethyl)piperidine hydro chloride (Intermediate 7, 0.85 g, 3.3 mmol) in DCM (15 ml) and $NEt_3$ (4.0 ml, 29.6 mmol), was added a solution of (3aR,5aR,5bR,7aR,9S,11aR,11bR, 13aS)-3a-(chlorocarbonyl)-1-isopropyl-5a,5b,8,8,11a-pentamethyl-2-oxo-3,3a,4,5,5a,5b,6,7,7a,8,9,10,11,11a,11b,12, 13,13a-octadecahydro-2H-cyclopenta[a]chrysen-9-yl acetate (Example 1-step 7, 1.75 g, 3.3 mmol) in DCM (20 ml) at 0° C. and allowed to stir at room temperature for about 16 hours. After completion of the reaction (monitored by TLC), the reaction mixture was diluted with DCM and washed with water, brine and dried over $Na_2SO_4$, and the solvent was evaporated and purified by silica gel column (elution 2% MeOH/DCM) to afford the title compound (1.3 g, yield: 58.1%) as an off white solid.

Step 3: Synthesis of 1-benzyl 3-((3aR,5aR,5bR,
7aR,9S,11aR,11bR,13aS)-3a-((S)-2-((4-fluoro pip-
eridin-1-yl)methyl)pyrrolidine-1-carbonyl)-1-isopro-
pyl-5a,5b,8,8,11a-pentamethyl-2-oxo-3,3a,4,5,5a,5b,
6,7,7a,8,9,10,11,11a,11b,12,13,13a-octadecahydro-
2H-cyclopenta[a]chrysen-9-yl) (1R,3S)-2,2-
dimethylcyclobutane-1,3-dicarboxylate

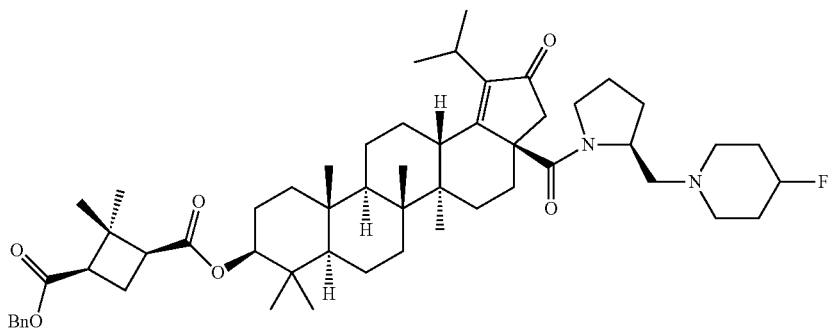

To a stirred solution of (3aR,5aR,5bR,7aR,9S,11aR,11bR, 13aS)-3a-((S)-2-((4-fluoro piperidin-1-yl)methyl)pyrrolidine-1-carbonyl)-9-hydroxy-1-isopropyl-5a,5b,8,8,11a-pentamethyl-3,3a,4,5,5a,5b,6,7,7a,8,9,10,11,11a,11b,12,13, 13a-octadecahydro-2H-cyclopenta[a]chrysen-2-one (step 2, 1.1 g, 1.72 mmol) and (1S,3R)-3-((benzyloxy)carbonyl)-2, 2-dimethyl cyclobutane-1-carboxylic acid (prepared as described in WO 2011/007230 A2, 0.68 g, 2.58 mmol) and DMAP (0.042 g, 0.34 mmol) in DCM (15 ml), was slowly added DCC (0.71 g, 3.44 mmol) in DCM (10 ml) at 0° C. and allowed to stir at room temperature for about 12 hours. After completion of the reaction (monitored by TLC), the reaction mixture was diluted with DCM and washed with water, saturated NaHCO$_3$ solution, brine and dried over Na$_2$SO$_4$. The solvent was evaporated and to the resulting solid, was added DCM (8 ml) and stirred for about 1 hour and filtered. The filtrate was concentrated under reduced pressure to afford the title compound (1.2 g, yield: 80%) as a white solid.

Step 4: Synthesis of (1R,3S)-3-(((((3aR,5aR,5bR, 7aR,9S,11aR,11bR,13aS)-3a-((S)-2-((4-fluoro piperidin-1-yl)methyl)pyrrolidine-1-carbonyl)-1-isopropyl-5a,5b,8,8, a-pentamethyl-2-oxo-3,3a,4,5,5a,5b,6, 7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR, 9S,11aR,11bR,13aS)-3a-((S)-2-((4-fluoropiperidin-1-yl) methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl) (1R,3S)-2,2-dimethylcyclobutane-1,3-dicarboxylate (step 3, 1.2 g, 1.33 mmol) in THF (15 ml), was added 10% Pd/C (0.20 g) and purged with nitrogen. The reaction mixture was stirred for about 12 hours under H$_2$ atmosphere. After completion of the reaction (monitored by TLC), the reaction mixture was filtered and filtrate was concentrated and purified by silica gel column (elution 2% MeOH in DCM) to afford the desired compound (0.37 g, yield: 35.23%) as a white solid. $^1$H NMR (300 MHz, DMSO-d$_6$): δ 12.17 (brs, 1H), 4.77-4.53 (m, 1H), 4.38-4.33 (m, 1H), 4.20 (m, 1H), 3.21-2.03 (m, 18H), 1.87-1.04 (m, 32H), 0.97-0.81 (m, 19H); ESI Mass: 793.56 [M+H]+; HPLC: 98.04%.

Example 11: Preparation of (1R,3S)-3-(((((3aR,5aR, 5bR,7aR,9S,11aR,11bR,13aS)-3a-((2-(5-(4-chlorophenyl)-1H-imidazol-2-yl)propan-2-yl)carbamoyl)-1-isopropyl-5a,5b,8,8,11a-pentamethyl-2-oxo-3,3a,4, 5,5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid

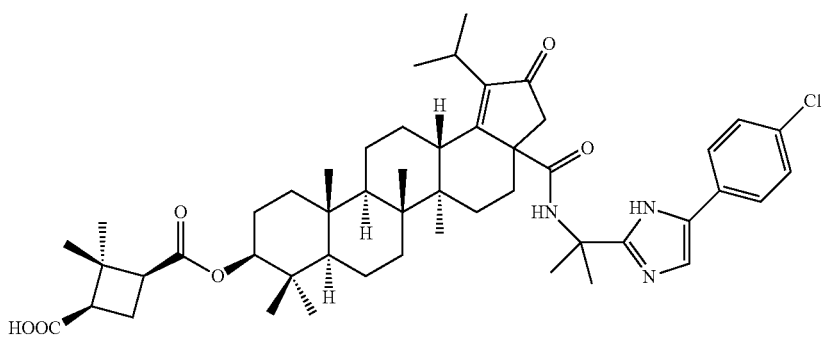

Step 1: Synthesis of (3aR,5aR,5bR,7aR,9S,11aR, 11bR,13aS)-9-hydroxy-1-isopropyl-5a,5b,8,8,11a-pentamethyl-2-oxo-2,3,4,5,5a,5b,6,7,7a,8,9,10,11, 11a,11b,12,13,13a-octadecahydro-3aH-cyclopenta[a]chrysene-3a-carbaldehyde Step 2: Synthesis of 1-benzyl 3-((3aR,5aR,5bR, 7aR,9S,11aR,11bR,13aS)-3a-formyl-1-isopropyl-5a, 5b,8,8,11a-pentamethyl-2-oxo-3,3a,4,5,5a,5b,6,7,7a, 8,9,10,11,11a,11b,12,13,13a-octadecahydro-2H-cyclopenta[a]chrysen-9-yl) (1R,3S)-2,2-dimethylcyclobutane-1,3-dicarboxylate

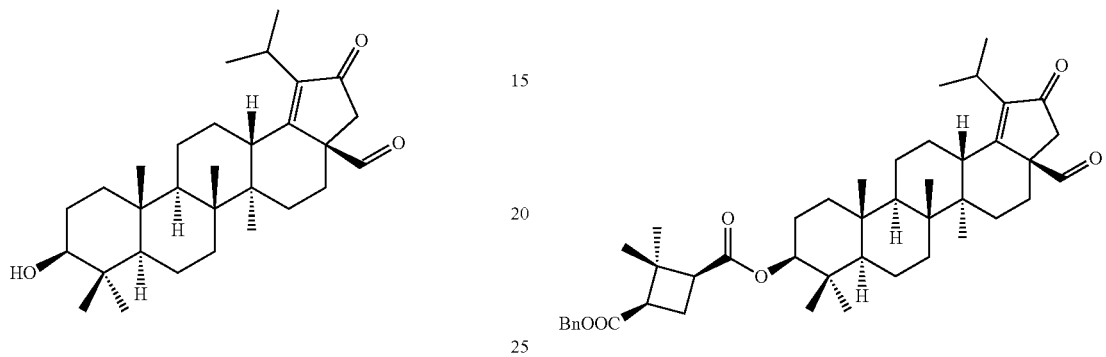

To a stirred solution of (3aR,5aR,5bR,7aR,9S,11aR,11bR, 13aS)-3a-formyl-1-isopropyl-5a,5b,8,8,11a-pentamethyl-2-oxo-3,3a,4,5,5a,5b,6,7,7a,8,9,10,11,11a,11b,12,13,13a-octadeca hydro-2H-cyclopenta[a]chrysen-9-yl acetate (Example 1-step 5, 10.0 g, 20.131 mmol, 1.0 eq) in methanol (100 ml) and $CH_2Cl_2$ (40 ml) was added $ZrCl_4$ (5.62 g, 24.15 mmol, 1.2 eq) in portions. The reaction mixture was warmed to approximately 45° C. and maintained for about 14 hours. TLC indicated starting material was consumed and the desired product was observed. The reaction was then treated with water (6 ml) and heated at 45-55° C. for about 30 minutes. The reaction was then cooled and evaporated under vacuum to 30 ml. Dichloromethane (100 ml) was added and the reaction was treated with 1N HCl (50 ml), mixed thoroughly, organic layer was separated and evaporated to 20 ml. Acetonitrile (80 ml) was added and heated at 60° C., thus forming a clear solution. Next was slowly added, 3N HCl (2.5 ml), which resulted in precipitate formation, the reaction mixture was heated at 60° C. until dimethyl acetal hydrolysis was complete followed by addition of water (120 ml). The reaction was allowed to cool to 0-10° C. and then the mixture was filtered and the resultant solid was rinsed with $CH_3CN/H_2O$ (1:1, 20 ml). The solid was then slurred in 100 ml of heptane and refluxed for about 3 hours. The slurry was then cooled to room temperature, filtered and then dried under vacuum at 40° C. gave the desired product (8.0 g, yield: 87.39%) as a white solid. 1H NMR (300 MHz, $CDCl_3$): δ ppm 9.32 (d, J=1.5 Hz, 1H), 3.30-3.18 (m, 2H), 2.56 (dd, J=12.6, 3.0 Hz, 1H), 2.42-2.34 (m, 2H), 2.08-2.02 (m, 2H), 1.97-1.06 (m, 21H), 1.03 (s, 3H), 0.97 (s, 3H), 0.95 (s, 3H), 0.88 (s, 3H), 0.77 (s, 3H), 0.73-0.67 (m, 1H).

To a stirred solution of (3aR,5aR,5bR,7aR,9S,11aR,11bR, 13aS)-9-hydroxy-1-isopropyl-5a,5b,8,8,11a-pentamethyl-2-oxo-2,3,4,5,5a,5b,6,7,7a,8,9,10,11,11a,11b,12,13,13a-octa-decahydro-3aH-cyclopenta[a]chrysene-3a-carbaldehyde (step 1, 5.5 g, 12.10 mmol, 1.0 eq) and (1S,3R)-3-((benzyloxy)carbonyl)-2,2-dimethylcyclobutane-1-carboxylicacid (prepared as described in WO 2011/007230 A2, 3.8 g, 14.52 mmol, 1.2 eq) in DCM (200 ml) at 0° C. was added triethyl amine (3.3 ml, 24.20 mmol, 2.0 eq), DMAP (0.738 g, 6.05 mmol, 0.5 eq) and 2,4,6-trichlorobenzoyl chloride (2.26 ml, 14.52 mmol, 1.2 eq). The reaction mixture was allowed to stir at room temperature for overnight. TLC indicated starting material was consumed and the desired product was observed. The reaction mixture was diluted with water (300 ml) and extracted with $CH_2Cl_2$ (3×350 ml). The combined organic extracts were dried over $Na_2SO_4$, filtered and evaporated under reduced pressure. The residue was purified by silicagel column chromatography by using 0-1% methanol in dichloromethane gradient. The fractions containing the expected product were combined and concentrated under reduced pressure to obtain the desired product (7.0 g, yield: 82.8%) as a white solid. 1H NMR (300 MHz, $CDCl_3$): δ ppm 9.31 (d, J=0.6 Hz, 1H), 7.37-7.34 (m, 5H), 5.15, 5.10 (ABq, $J_{AB}$=12.3 Hz, 2H), 4.45 (dd, J=11.4, 4.8 Hz, 1H), 3.31-3.20 (m, 1H), 2.86-2.73 (m, 2H), 2.70-2.61 (m, 1H), 2.59-2.51 (m, 1H), 2.42-2.33 (m, 2H), 2.10-1.98 (m, 3H), 1.97-1.08 (m, 21H), 1.34 (s, 3H), 1.03 (s, 3H), 0.97 (s, 3H), 0.94 (s, 3H), 0.90 (s, 3H), 0.85 (s, 3H), 0.84 (s, 3H), 0.82-0.77 (m, 1H).

Step 3: Synthesis of (3aR,5aR,5bR,7aR,9S,11aR, 11bR,13aS)-9-(((1S,3R)-3-((benzyloxy)carbonyl)-2, 2-dimethylcyclobutane-1-carbonyl)oxy)-1-isopropyl-5a,5b,8,8,11a-pentamethyl-2-oxo-2,3,4,5,5a,5b,6,7, 7a,8,9,10,11,11a,11b,12,13,13a-octadecahydro-3aH-cyclopenta[a]chrysene-3a-carboxylic acid

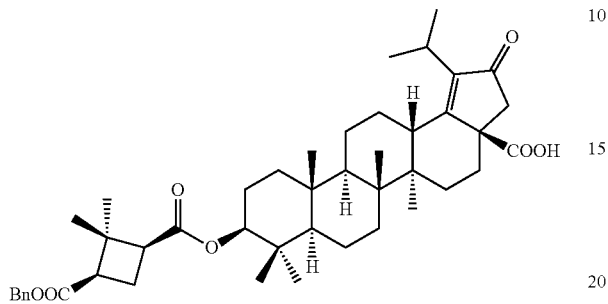

To an ice cooled solution of 1-benzyl 3-((3aR,5aR,5bR, 7aR,9S,11aR,11bR,13aS)-3a-formyl-1-isopropyl-5a,5b,8,8, 11a-pentamethyl-2-oxo-3,3a,4,5,5a,5b,6,7,7a,8,9,10,11,11a, 11b,12,13,13a-octadecahydro-2H-cyclopenta[a]chrysen-9-yl) (1R,3S)-2,2-dimethylcyclobutane-1,3-dicarboxylate (step 2, 7.0 g, 10.02 mmol, 1.0 eq) in t-butanol (70 ml), THF (150 ml) and 2-methyl 2-butene (5 ml) was added slowly a solution of $NaClO_2$ (10.82 g, 120.27 mmol, 12.0 eq) in water (60 ml), followed by $NaH_2PO_4$ (12.0 g, 100.22 mmol, 10.0 eq) in water (60 ml) over 15 minutes. The reaction mixture was allowed to stir at room temperature for about 4 hours. TLC indicated starting material was consumed and the desired product was observed. The reaction mixture was diluted with water (200 ml) and extracted with ethyl acetate (3×200 ml). The combined organic extracts were dried over sodium sulfate, filtered and evaporated under reduced pressure to obtain the desired product (7.0 g, yield: 98%) as a white solid. 1H NMR (300 MHz, $CDCl_3$): δ ppm 7.38-7.32 (m, 5H), 5.15, 5.10 (ABq, $J_{AB}$=12.3 Hz, 2H), 4.46 (dd, J=11.4, 4.8 Hz, 1H), 3.27-3.17 (m, 1H), 2.87-2.43 (m, 6H), 2.19 (d, J=18.6 Hz, 1H), 2.10-1.98 (m, 2H), 1.98-1.02 (m, 21H), 1.34 (s, 3H), 1.06 (s, 3H), 0.97 (s, 3H), 0.94 (s, 3H), 0.91 (s, 3H), 0.86 (s, 3H), 0.85 (s, 3H), 0.79 (m, 1H); ESI-MS: m/z 737.4 (M+Na)$^+$.

Step 4: Synthesis of 1-benzyl 3-((3aR,5aR,5bR, 7aR,9S,11aR,11bR,13aS)-3a-(chlorocarbonyl)-1-isopropyl-5a,5b,8,8,11a-pentamethyl-2-oxo-3,3a,4,5, 5a,5b,6,7,7a,8,9,10,11,11a,11b,12,13,13a-octadecahydro-2H-cyclopenta[a]chrysen-9-yl) (1R, 3S)-2,2-dimethylcyclobutane-1,3-dicarboxylate

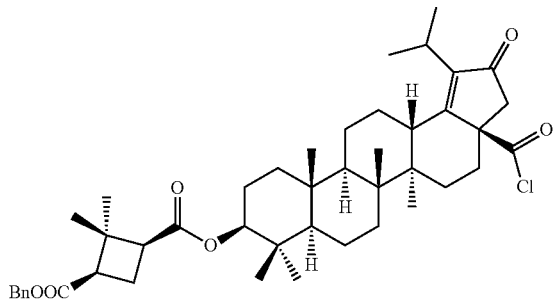

To a stirred solution of (3aR,5aR,5bR,7aR,9S,11aR,11bR, 13aS)-9-(((1S,3R)-3-((benzyloxy)carbonyl)-2,2-dimethyl-cyclobutane-1-carbonyl)oxy)-1-isopropyl-5a,5b,8,8,11a-pentamethyl-2-oxo-2,3,4,5,5a,5b,6,7,7a,8,9,10,11,11a,11b, 12,13,13a-octadecahydro-3aH-cyclopenta[a]chrysene-3a-carboxylic acid (step 3, 1.3 g, 1.82 mmol, 1.0 eq) in DCM (20 ml) at 0° C. under nitrogen atmosphere was added oxalyl chloride (0.47 ml, 5.46 mmol, 3.0 eq). The reaction mixture was allowed to stir at room temperature for about 4 hours. After completion of the reaction (monitored by TLC), the reaction mixture was evaporated under reduced pressure to obtain the desired product (1.3 g) as an oil, which is used as such for next step without further purification.

Step 5: Synthesis of 1-benzyl 3-((3aR,5aR,5bR, 7aR,9S,11aR,11bR,13aS)-3a-((2-(5-(4-chloro phenyl)-1H-imidazol-2-yl)propan-2-yl)carbamoyl)-1-isopropyl-5a,5b,8,8,11a-pentamethyl-2-oxo-3,3a,4,5, 5a,5b,6,7,7a,8,9,10,11,11a,11b,12,13,13a-octadecahydro-2H-cyclopenta[a]chrysen-9-yl) (1R, 3S)-2,2-dimethylcyclobutane-1,3-dicarboxylate

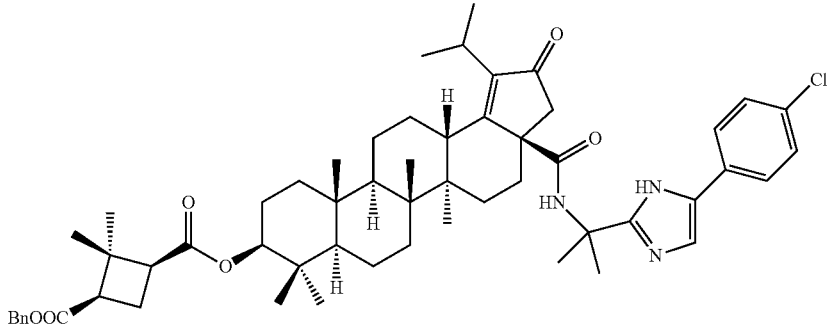

To a stirred solution of 2-(5-(4-chlorophenyl)-1H-imidazol-2-yl)propan-2-amine hydrochloride (Intermediate 10, 0.72 g, 2.67 mmol, 1.5 eq) in DCM (100 ml) at 0° C. under nitrogen atmosphere was added triethylamine (1.48 ml, 10.71 mmol, 6.0 eq) and 1-benzyl 3-((3aR,5aR,5bR,7aR,9S,11aR,11bR,13aS)-3a-(chlorocarbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-di methylcyclobutane-1,3-dicarboxylate (step 4, 1.3 g, 1.78 mmol, 1.0 eq) in DCM (15 ml). The reaction mixture was allowed to stir at room temperature for overnight. TLC indicated starting material was consumed and the desired product was observed. The reaction mixture was diluted with water (100 ml) and extracted with DCM (3×100 ml). The combined organic extracts were dried over sodium sulfate, filtered and evaporated under reduced pressure. The residue was purified by silicagel column chromatography by using 2% MeOH in DCM as an eluent to obtain the desired product (1.2 g, yield: 72.2%) as a white solid. 1H NMR (300 MHz, CDCl$_3$): δ ppm 10.33 (brs, 1H), 7.68 (d, J=7.8 Hz, 2H), 7.40-7.22 (m, 7H), 7.18 (s, 1H), 5.99 (s, 1H), 5.14, 5.09 (ABq, J$_{AB}$=12.6 Hz, 2H), 4.46-4.39 (m, 1H), 3.30-3.20 (m, 1H), 2.86-2.72 (m, 2H), 2.70-2.51 (m, 3H), 2.42 (d, J=18.9 Hz, 1H), 2.17 (d, J=18.9 Hz, 1H), 2.10-1.63 (m, 7H), 1.78 (s, 3H), 1.76 (s, 3H), 1.62-1.0 (m, 19H), 0.98-0.76 (m, 19H); ESI-MS: m/z 932.6 (M+H)$^+$.

Step 6: Synthesis of (1R,3S)-3-((((3aR,5aR,5bR,7aR,9S,11aR,11bR,13aS)-3a-((2-(5-(4-chlorophenyl)-1H-imidazol-2-yl)propan-2-yl)carbamoyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR,9S,11aR,11bR,13aS)-3a-((2-(5-(4-chlorophenyl)-1H-imidazol-2-yl)propan-2-yl)carbamoyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 5, 1.2 g, 1.28 mmol, 1.0 eq) in MeOH (40 ml), THF (20 ml) and water (10 ml) was added K$_2$CO$_3$ (3.55 g, 25.76 mmol, 20.0 eq). The reaction mixture was stirred at room temperature for about 36 hours. TLC indicated starting material was consumed and the desired product was observed. The reaction mixture was evaporated under reduced pressure, cooled to 0° C., diluted with water (40 ml), acidified with 2N HCl to pH-4.0 and extracted with DCM (3×100 ml). The combined organic extracts were washed with water (100 ml), dried over sodium sulfate, filtered and evaporated under reduced pressure. The residue was purified by silicagel column chromatography by using 3% MeOH in DCM as an eluent to obtain the desired product (0.2 g, yield: 18.5%) as a white solid. 1H NMR (300 MHz, CDCl$_3$): δ ppm 10.36 (s, 1H), 7.67 (d, 2H), 7.31 (d, J=7.8 Hz, 2H), 7.18 (s, 1H), 6.01 (brs, 1H), 4.44 (dd, J=11.4, 4.5 Hz, 1H), 3.30-3.20 (m, 1H), 2.86-2.74 (m, 2H), 2.61-2.51 (m, 3H), 2.42 (d, J=19.2 Hz, 1H), 2.17 (d, J=19.2 Hz, 1H), 2.11-1.84 (m, 6H), 1.78 (s, 3H), 1.76 (s, 3H), 1.72-0.95 (m, 17H), 1.37 (s, 3H), 1.06 (s, 3H), 0.91 (s, 3H), 0.88-0.72 (m, 13H); ESI-MS: m/z 842.6 (M+H)$^+$; HPLC: 97.0%.

Example 12: Preparation of (1R,3S)-3-((((3aR,5aR,5bR,7aR,9S,11aR,11bR,13aS)-1-isopropyl-5a,5b,8,8,11a-pentamethyl-3a-((2-methyl-1-(pyrrolidin-1-yl)propan-2-yl)carbamoyl)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethlcyclobutane-1-carboxylic acid

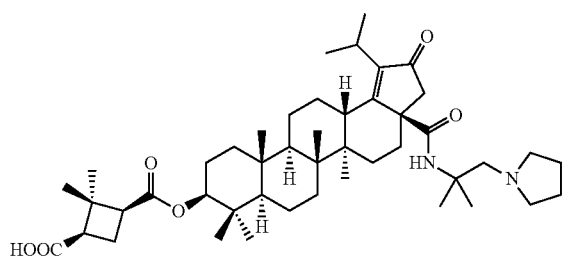

Step 1: Synthesis of 1-benzyl 3-((3aR,5aR,5bR,7aR,9S,11aR,11bR,13aS)-1-isopropyl-5a,5b,8,8,11a-pentamethyl-3a-((2-methyl-1-(pyrrolidin-1-yl)propan-2-yl)carbamoyl)-2-oxo-3,3a,4,5,5a,5b,6,7,7a,8,9,10,11,11a,11b,12,13,13a-octadecahydro-2H-cyclopenta[a]chrysen-9-yl)(1R,3S)-2,2-dimethylcyclobutane-1,3-dicarboxylate

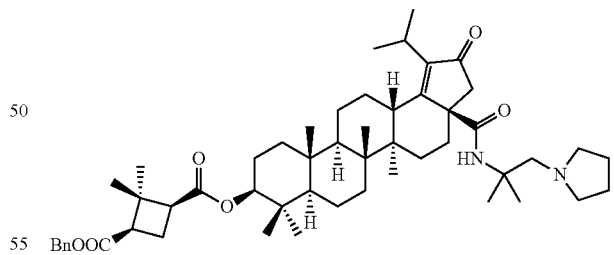

To a stirred solution of 2-methyl-1-(pyrrolidin-1-yl)propan-2-amine hydrochloride (Intermediate 3, 0.73 g, 4.11 mmol, 3.0 eq) in DCM (30 ml) at 0° C. under nitrogen atmosphere was added triethylamine (1.51 ml, 10.96 mmol, 8.0 eq) and 1-benzyl 3-((3aR, 5aR,5bR,7aR,9S,11aR,11bR,13aS)-3a-(chlorocarbonyl)-1-isopropyl-5a,5b,8,8,8,11a- pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclo butane-1,3-dicarboxylate (Example 11-step 4, 1.0 g, 1.37 mmol, 1.0 eq) in DCM (10 ml). The reaction mixture was allowed to stir at room temperature for overnight. TLC indicated starting material was consumed and the desired product was observed. The reaction mixture was diluted with water (150 ml) and extracted with DCM (3×200 ml). The combined organic extracts were dried over sodium sulfate, filtered and evaporated under reduced pressure. The residue was purified by silicagel column chromatography by using 2% MeOH in DCM as an eluent to obtain the desired product (0.3 g, yield: 26%) as a yellow solid. 1H NMR (300 MHz, CDCl$_3$): δ ppm 7.35 (m, 5H), 6.64 (s, 1H), 5.15, 5.10 (ABq, J$_{AB}$=12.6 Hz, 2H), 4.45 (dd, J=11.1, 4.5 Hz, 1H), 3.28-3.18 (m, 1H), 2.87-2.73 (m, 3H), 2.70-2.27 (m, 8H), 2.20-1.92 (m, 5H), 1.90-1.0 (m, 33H), 1.04 (s, 3H), 0.96 (s, 3H), 0.93 (s, 3H), 0.90 (s, 3H), 0.86 (s, 3H), 0.84 (s, 3H), 0.78 (m, 1H); ESI-MS: m/z 839.6 (M+H)$^+$.

Step 2: Synthesis of (1R,3S)-3-((((3aR,5aR,5bR,7aR,9S,11aR,11bR,13aS)-1-isopropyl-5a,5b,8,8,11a-pentamethyl-3a-((2-methyl-1-(pyrrolidin-1-yl)propan-2-yl)carbamoyl)-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a suspension of wet 10% Pd/C (0.3 g) in MeOH (25 ml) was added 1-benzyl 3-((3aR,5aR,5bR,7aR,9S,11aR,11bR,13aS)-1-isopropyl-5a,5b,8,8,11a-pentamethyl-3a-((2-methyl-1-(pyrrolidin-1-yl)propan-2-yl)carbamoyl)-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclo butane-1,3-dicarboxylate (step 1, 0.3 g, 0.357 mmol, 1.0 eq) in MeOH (25 ml). To this reaction mixture, ammonium formate (0.225 g, 3.57 mmol, 10.0 eq) was added and stirred at room temperature for about 4 hours. TLC indicated starting material was consumed and the desired product was observed. The reaction mixture was filtered through a pad of celite, washed with MeOH (100 ml) and the filtrate was evaporated under reduced pressure. The residue was purified by silicagel column chromatography (eluent: 8% MeOH:DCM), followed by recrystallization over acetonitrile gave the desired product (0.050 g, yield: 18.7%) as a white solid. 1H NMR (300 MHz, DMSO-d$_6$): δ ppm 12.1 (brs, 1H), 6.55 (s, 1H), 4.40-4.32 (m, 1H), 3.24-3.15 (m, 1H), 2.84-2.67 (m, 3H), 2.62-2.54 (m, 3H), 2.44-2.06 (m, 8H), 1.95-1.82 (m, 3H), 1.75-1.29 (m, 14H), 1.33 (s, 3H), 1.29-1.0 (m, 15H), 0.97 (s, 3H), 0.90 (brs, 6H), 0.88-0.78 (m, 10H); ESI-MS: m/z 749.6 (M+H)$^+$; HPLC: 96.9%.

Example 13: Preparation of (1R,3S)-3-((((3aR,5aR,5bR,7aR,9S,11aR,1 bR,13aS)-1-isopropyl-5a,5b,8,8,11a-pentamethyl-2-oxo-3a-((S)-2-(pyrrolidin-1-ylmethyl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

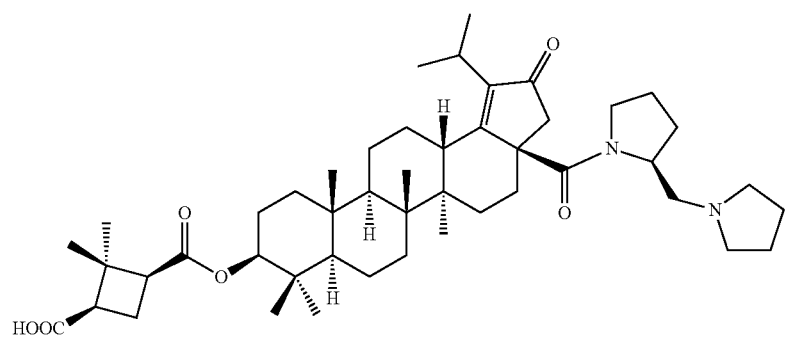

Step 1: Synthesis of 1-benzyl 3-((3aR,5aR,5bR,7aR,9S,11aR,11bR,13aS)-1-isopropyl-5a,5b,8,8,11a-pentamethyl-2-oxo-3a-((S)-2-(pyrrolidin-1-ylmethyl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl)(1R,3S)-2,2-dimethyl cyclobutane-1,3-dicarboxylate

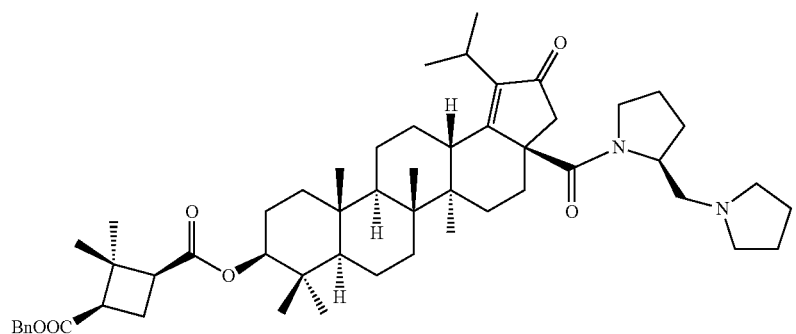

To a stirred solution of (S)-1-(pyrrolidin-2-ylmethyl)pyrrolidine (Intermediate 2, 0.25 g, 1.63 mmol, 1.2 eq) in DCM (10 ml) at 0° C. was added TEA (0.76 ml, 5.44 mmol, 4.0 eq) and 1-benzyl 3-((3aR,5aR,5bR,7aR,9S,11aR,11bR,13aS)-3a-(chlorocarbonyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (Example 11-step 4, 1.0 g, 1.36 mmol, 1.0 eq) in DCM (10 ml). The reaction mixture was allowed to stir at room temperature for overnight. TLC indicated starting material was consumed and the desired product was observed. The reaction mixture was diluted with water (20 ml) and extracted with DCM (3×50 ml). The combined organic extracts were washed with water (40 ml), dried over sodium sulfate, filtered and evaporated under reduced pressure. The residue was purified by silicagel column chromatography by using 5% MeOH in DCM as an eluent to obtain the desired product (800 mg, yield: 68.9%) as a white solid. 1H NMR (300 MHz, DMSO-$d_6$): δ ppm 7.38-7.33 (m, 5H), 5.12, 5.06 (ABq, $J_{AB}$=12.3 Hz, 2H), 4.39-4.31 (m, 1H), 4.23 (m, 1H), 3.22-3.12 (m, 2H), 3.11-3.0 (m, 2H), 2.98-2.89 (m, 2H), 2.88-2.79 (m, 2H), 2.71-2.60 (m, 2H), 2.42-2.30 (m, 3H), 2.15-2.02 (m, 2H), 2.02-1.90 (m, 3H), 1.89-1.61 (m, 10H), 1.61-1.31 (m, 9H), 1.31-1.0 (m, 10H), 1.26 (s, 3H), 0.96 (s, 3H), 0.93 (s, 3H), 0.87-0.78 (m, 13H); ESI-MS: m/z 851.6 (M+H)⁺.

Step 2: Synthesis of (1R,3S)-3-((((3aR,5aR,5bR,7aR,9S,11aR,11bR,13aS)-1-isopropyl-5a,5b,8,8,11a-pentamethyl-2-oxo-3a-((S)-2-(pyrrolidin-1-ylmethyl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR,9S,11aR,11bR,13aS)-1-isopropyl-5a,5b,8,8,11a-pentamethyl-2-oxo-3a-((S)-2-(pyrrolidin-1-ylmethyl)pyrrolidine-1-carbonyl)-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 1, 0.8 g, 0.94 mmol, 1.0 eq) in MeOH (16.8 ml) and THF (16.8 ml) at 0° C. was added aqueous 2.5N KOH solution (2.7 ml, 7.05 mmol, 7.5 eq). The reaction mixture was allowed to stir at room temperature for overnight. TLC indicated starting material was consumed and the desired product was observed. The organic phase was evaporated under reduced pressure, diluted with water (30 ml), cooled to 0° C., acidified with 1N HCl to pH-6.0 and extracted with DCM (3×60 ml). The combined organic extracts were dried over sodium sulfate, filtered and evaporated under reduced pressure. The residue was purified by silicagel column chromatography by using 8% MeOH in DCM as an eluent to obtain the desired product (50 mg, yield: 7%) as a white solid. 1H NMR (300 MHz, Pyridine-$d_5$): δ ppm 4.74 (dd, J=11.1, 4.2 Hz, 1H), 4.67 (m, 1H), 3.38-3.18 (m, 2H), 3.18-2.96 (m, 5H), 2.92-2.84 (m, 1H), 2.83-2.50 (m, 6H), 2.39 (d, J=18.9 Hz, 1H), 2.30-2.10 (m, 3H), 2.02-1.54 (m, 12H), 1.57 (s, 3H), 1.53-1.0 (m, 20H), 1.18 (s, 3H), 1.06 (s, 3H), 0.98 (s, 3H), 0.96 (s, 3H), 0.85 (s, 3H), 0.87-0.79 (m, 1H); ESI-MS: m/z 761.6 (M+H)$^+$; HPLC: 90.9%.

Example 14: Preparation of (1R,3S)-3-((((3aR,5aR,5bR,7aR,9S,11aR,11bR,13aS)-3a-((4-chloro benzyl)(2-(dimethylamino)ethyl)carbamoyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)oxy)carbonyl)-2,2-dimethylcyclobutane-1-carboxylic acid

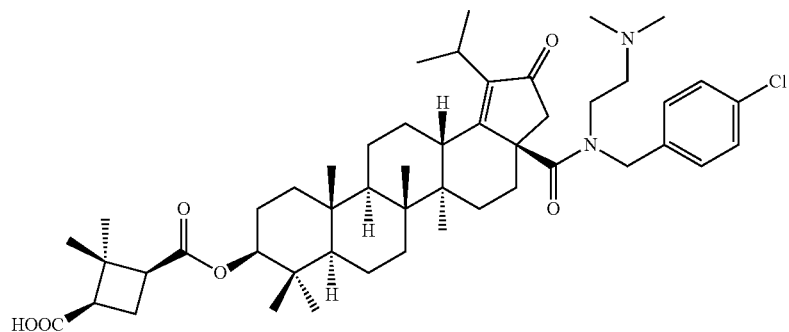

Step 1: Synthesis of 1-benzyl 3-((3aR,5aR,5bR,7aR,9S,11aR,11bR,13aS)-3a-((4-chlorobenzyl)(2-(dimethylamino)ethyl)carbamoyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl)(1R,3S)-2,2-dimethylcyclobutane-1,3-dicarboxylate

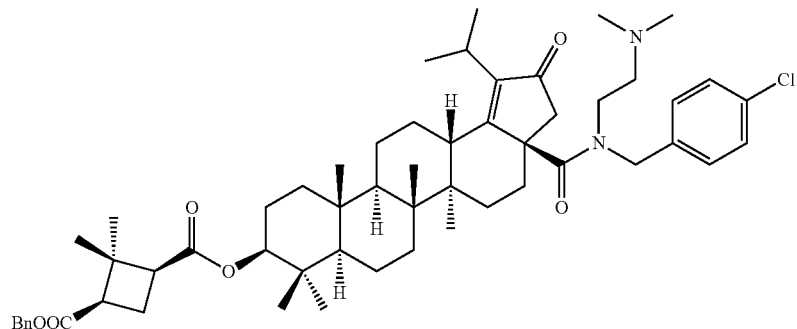

To a stirred solution of $N^1$-(4-chlorobenzyl)-$N^2$,$N^2$-dimethylethane-1,2-diamine (Intermediate 11, 0.87 g, 4.10 mmol, 2.0 eq) in DCM (10 ml) at 0° C. under nitrogen atmosphere was added triethylamine (1.14 ml, 8.2 mmol, 4.0 eq) and 1-benzyl 3-((3aR,5aR, 5bR,7aR,9S,11aR,11bR, 13aS)-3a-(chlorocarbonyl)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl) (1R,3S)-2,2-dimethylcyclobutane-1,3-dicarboxylate (Example 11-step 4, 1.5 g, 2.05 mmol, 1.0 eq) in DCM (15 ml). The reaction mixture was allowed to stir at room temperature for overnight. TLC indicated starting material was consumed and the desired product was observed. The reaction mixture was diluted with water (20 ml) and extracted with DCM (3×50 ml). The combined organic extracts were washed with water (40 ml), dried over sodium sulfate, filtered and evaporated under reduced pressure. The residue was purified by silicagel column chromatography by using 5% MeOH in DCM as an eluent to obtain the desired product (1.0 g, yield: 53.7%) as a white solid. 1H NMR (300 MHz, CDCl$_3$): δ ppm 7.37-7.28 (m, 7H), 7.24-7.20 (m, 1H), 7.01 (m, 1H), 5.15, 5.09 (ABq, J$_{AB}$=12.6 Hz, 2H), 4.73-4.63 (m, 1H), 4.54-4.39 (m, 2H), 3.27-2.95 (m, 3H), 2.87-2.72 (m, 3H), 2.72-2.40 (m, 5H), 2.30-2.11 (m, 2H), 2.20 (s, 6H), 2.10-1.98 (m, 2H), 1.88-1.15 (m, 22H), 1.34 (s, 3H), 1.13-0.76 (m, 20H); ESI-MS: m/z 909.6 (M+H)$^+$.

Step 2: Synthesis of (1R,3S)-3-((((3aR,5aR,5bR, 7aR,9S,11aR,11bR,13aS)-3a-((4-chloro benzyl)(2-(dimethylamino)ethyl)carbamoyl)-1-isopropyl-5a,5b, 8,8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl)oxy)carbonyl)-2,2-dimethylcyclobutane-1-carboxylic acid To a stirred solution of 1-benzyl 3-((3aR,5aR,5bR,7aR, 9S,11aR,11bR,13aS)-3a-((4-chlorobenzyl) (2-(dimethylamino)ethyl)carbamoyl)-1-isopropyl-5a,5b,8,8,11a-pentamethyl-2-oxo-3,3a,4,5,5a,5b,6,7,7a,8,9,10,11,11a,11b,12,13, 13a-octadecahydro-2H-cyclopenta[a]chrysen-9-yl) (1R,3S)-2,2-dimethylcyclobutane-1,3-dicarboxylate (step 1, 1.0 g, 1.1 mmol, 1.0 eq) in MeOH (20 ml) and THF (20 ml) at 0° C. was added aqueous 2.5N KOH solution (3.3 ml, 8.25 mmol, 7.5 eq). The reaction mixture was allowed to stir at room temperature for overnight. TLC indicated starting material was consumed and the desired product was observed. The organic phase was evaporated under reduced pressure, diluted with water (10 ml), cooled to 0° C., acidified with 1N HCl to pH-6.0 and extracted with DCM (3×50 ml). The combined organic extracts were washed with water (50 ml) dried over sodium sulfate, filtered and evaporated under reduced pressure. The residue was purified by silicagel column chromatography by using 8% MeOH in DCM as an eluent to obtain the desired product (150 mg, yield: 16.6%) as a white solid. 1H NMR (300 MHz, Pyridine-d$^5$): δ ppm 7.42 (d, J=8.4 Hz, 2H), 7.38 (d, J=8.7 Hz, 2H), 4.75 (dd, J=11.1, 4.2 Hz, 1H), 4.70, 4.63 (ABq, J$_{AB}$=15.6 Hz, 2H), 3.45-2.98 (m, 8H), 2.71-2.58 (m, 2H), 2.43-2.37 (m, 2H), 2.28-2.21 (m, 1H), 2.18 (s, 6H), 2.15-1.62 (m, 7H), 1.58 (s, 3H), 1.51 (d, J=1.8 Hz, 3H) 1.487 (d, J=1.8 Hz, 3H), 1.46 (s, 3H), 1.45-1.25 (m, 6H), 1.19 (s, 3H), 1.17-1.06 (m, 3H), 1.03 (s, 3H), 0.99 (s, 3H), 0.98 (s, 3H), 0.93 (s, 3H), 0.88-0.83 (m, 3H); ESI-MS: m/z 819.5 (M+H)$^+$; HPLC: 97.9%.

Example 15: Preparation of (1R,3S)-3-((((3aR,5aR, 5bR,7aR,9S,11aR,11bR,13aS)-3a-((1-hydroxy-2-methylpropan-2-yl)carbamoyl)-1-isopropyl-5a,5b,8, 8,11a-pentamethyl-2-oxo-3,3a,4,5,5a,5b,6,7,7a,8,9, 10,11,11a,11b,12,13,13a-octadecahydro-2H-cyclopenta[a]chrysen-9-yl)oxy)carbonyl)-2,2-dimethylcyclobutane-1-carboxylic acid

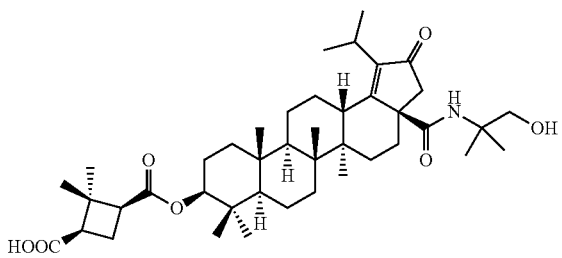

Step 1: Synthesis of 1-benzyl 3-((3aR,5aR,5bR, 7aR,9S,11aR,11bR,13aS)-3a-((1-hydroxy-2-methylpropan-2-yl)carbamoyl)-1-isopropyl-5a,5b,8,8,11a-pentamethyl-2-oxo-3,3a,4,5,5a,5b,6,7,7a,8,9,10,11, 11a,11b,12,13,13a-octadecahydro-2H-cyclopenta[a]chrysen-9-yl) (1R,3S)-2,2-dimethyl cyclobutane-1, 3-dicarboxylate

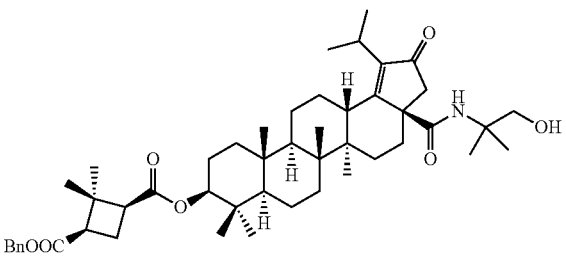

To a stirred solution of 2-amino-2-methylpropan-1-ol (0.182 g, 2.046 mmol, 1.5 eq) in DCM (10 ml) at 0° C. under nitrogen was added triethyl amine (0.945 ml, 6.814 mmol, 5.0 eq) and 1-benzyl 3-((3aR,5aR,5bR,7aR,9S,11aR,11bR, 13aS)-3a-(chlorocarbonyl)-1-isopropyl-5a,5b,8,8,11a-pentamethyl-2-oxo-3,3a,4,5,5a,5b,6,7,7a,8,9,10,11,11a,11b,12, 13,13a-octadecahydro-2H-cyclopenta[a]chrysen-9-yl) (1R, 3S)-2,2-dimethylcyclobutane-1,3-dicarboxylate (Example 11-step 4, 1.0 g, 1.364 mmol, 1.0 eq) in DCM (20 ml). The reaction mixture was removed from the ice bath and was stirred at room temperature for overnight. TLC indicated starting material was consumed and the desired product was observed. The reaction mixture was diluted with water (50 ml) and extracted with DCM (3×50 ml). The combined organic extracts were washed with 0.5N HCl (15 ml) and water (15 ml), dried over sodium sulfate, filtered and evaporated under reduced pressure. The residue was purified by silicagel column chromatography by using 2% methanol in dichloromethane as an eluent to obtain the desired product (1.0 g, yield: 93.24%) as a white solid. 1H NMR (300 MHz, CDCl$_3$): δ ppm 7.37-7.30 (m, 5H), 5.41 (s, 1H), 5.13, 5.08 (ABq, J$_{AB}$=12.3 Hz, 2H), 4.43 (dd, J=11.1, 4.5 Hz, 1H), 3.57, 3.50 (ABq, J$_{AB}$=11.4 Hz, 2H), 3.28-3.20 (m, 1H), 2.95-2.51 (m, 5H), 2.40 (d, J=18.9 Hz, 1H), 2.15 (d, J=18.9

Hz, 1H), 2.07-1.19 (m, 22H), 1.32 (s, 3H), 1.17 (s, 6H), 1.12-1.05 (m, 1H), 1.02 (s, 3H), 0.94 (s, 3H), 0.91 (s, 3H), 0.88 (s, 3H), 0.84 (s, 3H), 0.82 (s, 3H), 0.81-0.75 (m, 1H); ESI-MS: m/z 786.51 (M+H)+.

Step 2: Synthesis of (1R,3S)-3-((((3aR,5aR,5bR, 7aR,9S,11aR,11bR,13aS)-3a-((1-hydroxy-2-methyl-propan-2-yl)carbamoyl)-1-isopropyl-5a,5b,8,8,11a-pentamethyl-2-oxo-3,3a,4,5,5a,5b,6,7,7a,8,9,10,11, 11a,11b,12,13,13a-octadecahydro-2H-cyclopenta[a] chrysen-9-yl)oxy)carbonyl)-2,2-dimethylcyclobutane-1-carboxylic acid To a stirred solution of 1-benzyl 3-((3aR,5aR,5bR,7aR, 9S,11aR,11bR,13aS)-3a-((1-hydroxy-2-methylpropan-2-yl) carbamoyl)-1-isopropyl-5a,5b,8,8,11a-pentamethyl-2-oxo-3,3a,4,5,5a,5b,6,7,7a,8,9,10,11,11a,11b,12,13,13a-octadecahydro-2H-cyclopenta[a]chrysen-9-yl) (1R,3S)-2,2-dimethylcyclobutane-1,3-dicarboxylate (step 1, 1.0 g, 1.272 mmol, 1.0 eq) in MeOH (20 ml) and THF (20 ml) was added aqueous 2.5N KOH solution (5.08 ml, 12.72 mmol, 10.0 eq). The reaction mixture was stirred at room temperature for overnight. TLC indicated starting material was consumed and the desired product was observed. The organic phase was evaporated under reduced pressure, the reaction mixture was diluted with water (20 ml), cooled to 0° C., pH adjusted to 3.0 with 1N HCl and extracted with DCM (3×50 ml). The combined organic extracts were washed with water (20 ml), dried over sodium sulfate, filtered and evaporated under reduced pressure. The residue was purified by silicagel column chromatography by using 0-3% methanol in dichloromethane gradient. The fractions containing the product were combined and concentrated under reduced pressure to give a solid. To this solid compound, hexane (15 ml) was added and heated to reflux for about 30 minutes. The mixture was cooled to 0° C., solid was filtered, washed with n-hexane and dried under vacuum to obtain the desired product (0.4 g, yield: 45.4%) as a white solid. 1H NMR (300 MHz, CDCl$_3$): δ ppm 5.42 (brs, 1H), 4.44 (dd, J=11.4, 4.5 Hz, 1H), 3.57, 3.51 (ABq, J$_{AB}$=11.4 Hz, 2H), 3.30-3.18 (m, 1H), 2.85-2.65 (m, 3H), 2.64-2.50 (m, 2H), 2.413 (d, J=19.2 Hz, 1H), 2.15 (d, J=19.2 Hz, 1H), 2.08-1.98 (m, 1H), 1.97-1.10 (m, 28H), 1.35 (s, 3H), 1.05 (s, 3H), 1.02 (s, 3H), 0.91 (s, 3H), 0.89 (s, 3H), 0.85 (s, 3H), 0.83 (s, 3H), 0.82-0.77 (m, 1H); ESI-MS: m/z 696.52 (M+H)+; HPLC: 96.65%.

Pharmacological Activity

The compounds described herein can be tested for their antiviral activity following procedures known to a person of ordinary skill in the art. For example, the following protocols can be employed for testing the compounds. These protocols are illustrative and do not limit to the scope of the invention.

Example 16: Evaluation of Compounds Antiviral Activity

MT2 cells were infected with HIV-1 strain 92HT599 (10 TCID 50/30000 cells). The infected cells were plated at the concentration of ~30 000 cells per well in 96 well plate. Test compound was added to the micro plate in defined format with the final concentration of DMSO (vehicle) is not more than 1%. Incubation was carried out in CO$_2$ incubator for ~96 hours for viral infection. At the end of incubation period an aliquot from each well was taken for p24 estimation. The quantitation of p24 is an index for antiviral activity of the compound. Percent inhibition was calculated with reference to control values (vehicle controls).

P-24 estimation was carried out using Advance biosciences kit as per the procedure detailed by supplier.

Results

TABLE 1

| Example No. | Antiviral activity (% inhibition) | | |
|---|---|---|---|
| | 1 μM | 0.1 μM | 0.01 μM |
| 1. | 99 | 98 | 100 |
| 2. | 100 | 100 | 60 |
| 3. | 100 | 100 | 100 |
| 4. | 100 | 100 | 100 |
| 5. | 100 | 100 | 100 |
| 6. | 100 | 100 | 100 |
| 7. | 100 | 100 | 100 |
| 8. | 100 | 100 | 100 |
| 9. | 100 | 100 | 100 |
| 10. | 100 | 100 | 97 |
| 11. | 99 | 99 | 92 |
| 12. | 100 | 95 | 9 |
| 13. | 100 | 100 | 96 |
| 14. | 100 | 100 | 100 |
| 15. | 100 | 100 | 97 |

TABLE 1A

| Example No. | Antiviral activity | |
|---|---|---|
| | IC$_{50}$ (nM) 0% | IC$_{50}$ (nM) 40% serum |
| 1. | 5.21 | 3.92 |
| 2. | 3.89 | 51.2 |
| 3. | 1.82 | 0.81 |
| 4. | 0.68 | 54.5 |
| 5. | 0.93 | 25.5 |
| 6. | 0.72 | 202.6 |
| 7. | 24.68 | 313.2 |
| 8. | 3.7 | 14.2 |
| 9. | 7.44 | 342.2 |
| 10. | 1.06 | 0.93 |
| 11. | 2.93 | 118 |
| 12. | 3.71 | 163.8 |
| 13. | 0.73 | 17.08 |
| 14. | 1.72 | 9.83 |
| 15. | 2.84 | 414.7 |

Example 17: Evaluation of Compounds Cyto-Toxicity (MTT Assay)

On day 1 calculate the number of cells required for the assay and seed 3×104 cells in 200 μl per well. Weigh the compound and dissolve it in DMSO to get 10 mM stock which is further diluted to 3 mM and 1 mM. The drugs from these stocks were added to plate to get final concentration of 100 μM, 30 μM and 10 μM. Add DMSO to controls in a way to obtain final concentration of solvent that is not greater than 1%. Incubate for 4 days in 5% CO$_2$ incubator at 37° C. On day 4, 100 μl of medium was removed from each well without disturbing the cells. Add 10 μl of MTT reagent and incubate for 4 hours at 5% CO$_2$ incubator at 37° C. for formation of crystals. Add 200 μl of 0.1N acidic isopropanol to dissolve the crystals and read the plate at 590 nm.

Results

TABLE 2

| Example No. | Cytotoxicity % viability | | |
|---|---|---|---|
| | 100 μM | 30 μM | 10 μM |
| 1. | 62 | 67 | 80 |
| 2. | 90 | 100 | 100 |
| 3. | 45 | 67 | 98 |
| 4. | 2 | 6 | 62 |
| 5. | 73 | 70 | 70 |
| 6. | 6 | 10 | 57 |
| 7. | 8 | 9 | 65 |
| 8. | 2 | 5 | 29 |
| 9. | 8 | 9 | 40 |
| 10. | 4 | 4 | 31 |
| 11. | 4 | 3 | 48 |
| 12. | 96 | 100 | 100 |
| 13. | 28 | 26 | 69 |
| 14. | 12 | 12 | 91 |
| 15. | 6 | 22 | 70 |

Example 18: Evaluation of Compounds Single Dose Oral Pharmacokinetic Study

The test item was administered through oral route to animals (rat/mice) at 30 mg/kg dose in a suitable vehicle (10% Solutol+20% PEG) at 10 ml/kg dose volume. Blood samples (~50 μL at each time point) were collected from retro-orbital plexus using K3 EDTA as anticoagulant in eppendorf tubes at defined time intervals 30 minutes, 1 hour, 2 hour, 4 hour, 8 hour, 24 hour & 48 hour under light ether anaesthesia. The samples were centrifuged at 3500×g to separate plasma and stored at −80° C. until analysis. Plasma 25I1 for Mice were processed as per described in sample preparation.

Standard solutions of the test compound 1 mg/mL solutions were prepared in DMSO and further dilutions were made in methanol. The calibration curve samples for LCMSMS analysis were prepared by spiking 25 μl of Mice plasma with 2.5 μl and of the appropriate working standard solution to obtain final concentrations 0.078, 0.156, 0.312, 0.625, 1.25, 2.5, 5, 10, 20 & 40 g/ml. To the test compound plasma extraction was carried out using Acetonitrile precipitation. After reconstitution with solvent (50% Acetonitrile in Buffer) samples were analyzed by LCMSMS to get the concentrations to calculate PK Parameters.

Results

TABLE 3

| | Mice oral PK @30 mg/kg | |
|---|---|---|
| Example No. | Cmax (μg/mL) | AUC 0-t (μg · hr/ml) |
| 1 | 8.65 | 69.80 |
| 2 | 11.87 | 147.67 |
| 3 | 8.53 | 48.55 |
| 6 | 11.53 | 76.58 |
| 7 | 7.41 | 28.83 |
| 8 | 15.25 | 265.18 |
| 9 | 10.87 | 106.56 |
| 11 | 10.03 | 142.64 |
| 12 | 5.10 | 19.00 |
| 13 | 16.99 | 319.85 |
| 14 | 9.64 | 165.72 |
| 15 | 9.08 | 88.71 |

REFERENCES

1. Antiviral methods and protocols (Eds: D Kinchington and R F Schinazi) Humana Press Inc., 2000.
2. HIV protocols (Eds: N L Michael and J H Kim) Humana Press Inc, 1999.
3. DAIDS Virology manual from HIV laboratories, Publication NIH-97-3838, 1997.
4. HIV-1 p24 antigen capture assay, enzyme immunoassay for detection of Human immunodeficiency Virus Type 1 (HIV-1) p24 in tissue culture media—Advanced bio science laboratories, Inc kit procedure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

The invention claimed is:

1. The A compound of the formula (1):

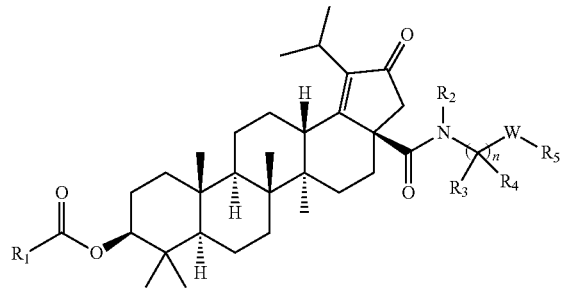

Formula (1)

wherein, $R_1$ is

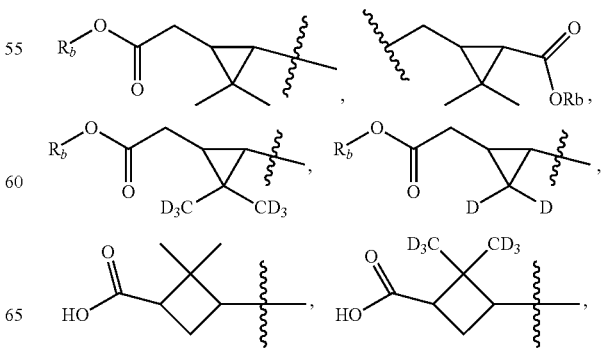

-continued

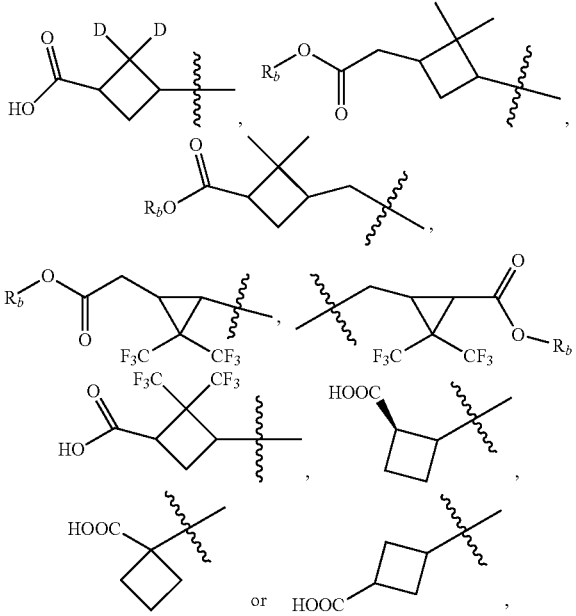

wherein $R_b$ is hydrogen, substituted or unsubstituted alkyl, or substituted or unsubstituted cycloalkyl;

$R_2$ is selected from hydrogen, substituted or unsubstituted alkyl, substituted or unsubstituted alkoxylalkoxy or substituted or unsubstituted amino alkyl;

$R_3$ is selected from substituted or unsubstituted alkyl, substituted or unsubstituted amine, substituted or unsubstituted cycloalkyl, substituted or unsubstituted heterocyclyl or substituted or unsubstituted heteroaryl;

or $R_2$ and $R_3$ optionally are taken together with the N-atom and C-atom to which they are attached to form substituted or unsubstituted 4-7 membered N-contained heterocyclyl; wherein the substituent is heterocyclyl;

$R_4$ is selected from hydrogen, substituted or unsubstituted alkyl, substituted or unsubstituted amine, substituted or unsubstituted cycloalkyl, substituted or unsubstituted heterocyclyl or substituted or unsubstituted heteroaryl;

W is —$CH_2$—, substituted or unsubstituted alkyl, substituted or unsubstituted heterocyclyl or substituted or unsubstituted heteroaryl;

$R_5$ is selected from hydroxy, substituted or unsubstituted aryl, substituted or unsubstituted heterocyclyl or substituted or unsubstituted heteroaryl; wherein the substituent is halo or hydroxyl alkyl;

'n' is 1;

a pharmaceutically acceptable salt thereof, a pharmaceutically acceptable solvate thereof, a pharmaceutically acceptable hydrate thereof, a N-oxide thereof, a tautomer thereof, a regioisomer thereof, a stereoisomer thereof, a prodrug thereof or a polymorph thereof.

2. The compound of claim 1, wherein $R_1$ is

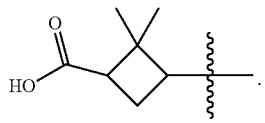 [SMILES: *C1CC(C(=O)O)C1(C)C]

3. A compound selected from the group consisting of:

(1R,3S)-3-((((3aR,5aR,5bR,7aR,9S,11aR,11bR,13aS)-1-isopropyl-5a,5b,8,8,11a-pentamethyl-2-oxo-3a-((S)-2-(5-phenyl-1H-imidazol-2-yl)pyrrolidine-1-carbonyl)-3,3a,4,5, 5a,5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3S)-3-((((3aR,5aR,5bR,7aR,9S,11aR,11bR,13aS)-3aS)-2-(5-(4-fluorophenyl)-1H-imidazol-2-yl)pyrrolidine-1-carbonyl)-1-isopropyl-5a,5b,8,8,11a-pentamethyl-2-oxo-3, 3a,4,5,5a,5b,6,7,7a,8,9,10,11,11a,11b, 12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-((S)-2-(5-(pyridin-3-yl)-1H-imidazol-2-yl)pyrrolidine-1-carbonyl)-3, 3a,4,5,5a,5b,6,7,7a,8,9,10,11,11a,11b,12,13, 13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-((R)-[1,3'-bipyrrolidine]-1'-carbonyl)-1-isopropyl-5a,5b,8,8,11a-pentamethyl-2-oxo-3,3a,4,5,5a,5b,6,7, 7a,8,9,10,11,11a, 11b,12,13,13a-octadecahydro-2H-cyclopenta[a]chrysen-9-yl)oxy)carbonyl)-2,2-dimethyl cyclobutane-1-carboxylic acid, (1R,3S)-3-((((3aR,5aR,5bR,7aR,9S,11aR,11bR,13aS)-3a-((S)-2-(((S)-2-(hydroxy methyl)pyrrolidin-1-yl) methyl)pyrrolidine-1-carbonyl)-1-isopropyl-5a,5b,8,8, 11a-penta methyl-2-oxo-3,3a,4,5,5a,5b,6,7,7a,8,9,10, 11,11a,11b,12,13,13a-octadecahydro-2H-cyclo penta [a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-((S)-2-((3,3-difluoro pyrrolidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a] chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-3a-((S)-2-((4,4-difluoro piperidin-1-yl)methyl)pyrrolidine-1-carbonyl)-1-isopropyl-5a,5b,8,8,11a-pentamethyl-2-oxo-3,3a,4,5,5a,5b,6,7,7a,8,9,10,11,11a,11b, 12,13,13a-octadecahydro-2H-cyclopenta[a]chrysen-9-yl)oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-((2-(5-phenyl-1H-imidazol-2-yl)propan-2-yl)carbamoyl)-3, 3a,4,5,5a, 5b,6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3S)-3-((((3aR,5aR,5bR,7aR,9S,11aR,11bR,13aS)-3a-((S)-2-(2-hydroxypropan-2-yl)pyrrolidine-1-carbonyl)-1-isopropyl-5a,5b,8,8,11a-pentamethyl-2-oxo-3, 3a,4,5,5a,5b,6,7, 7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3S)-3-((((3aR,5aR,5bR,7aR,9S,11aR,11bR,13aS)-3a-((S)-2-((4-fluoropiperidin-1-yl)methyl)pyrrolidine-1-carbonyl)-1-isopropyl-5a,5b,8,8,11a-pentamethyl-2-oxo-3,3a,5,5a, 5b,6,7,7a,8,9,10,11,11a,11b,12,13, 13a-octadecahydro-2H-cyclopenta[a]chrysen-9-yl) oxy) carbonyl)-2,2-dimethylcyclobutane-1-carboxylic acid, (1R,3S)-3-((((3aR,5aR,5bR,7aR,9S,11aR,11bR,13aS)-3a-((2-(5-(4-chlorophenyl)-1H-imidazol-2-yl)propan-2-yl)carbamoyl)-1-isopropyl-5a,5b,8,8,11a-pentamethyl-2-oxo-3,3a,4, 5,5a,5b,6,7,7a,8,9,10,11,11a,11b,12,13,13a-octadecahydro-2H-cyclopenta[a]chrysen-9-yl) oxy)carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,1a-pentamethyl-3a-((2-methyl-1-(pyrrolidin-1-yl)propan-2-yl)carbamoyl)-2-oxo-3,3a,4,5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3S)-3-((((3aR,5aR,5bR,7aR,9S,11aR,11bR,13aS)-1-isopropyl-5a,5b,8,8,11a-pentamethyl-2-oxo-3a-((S)-2-(pyrrolidin-1-ylmethyl)pyrrolidine-1-carbonyl)-3,3a,4, 5,5a,5b, 6,7,7a,8,9,10,11,11a,11b,12,13,13a-octadecahydro-2H-cyclopenta[a]chrysen-9-yl)oxy) carbonyl)-2,2-dimethylcyclobutane-1-carboxylic acid, (1R,3S)-3-((((3aR,5aR,5bR,7aR,9S,11aR,11bR,13aS)-3a-((4-chlorobenzyl)(2-(di methylamino)ethyl)carbamoyl)-1-isopropyl-5a,5b,8,8,11a-pentamethyl-2-oxo-3,3a,4,5,5a,5b, 6,7,7a,8,9,10,11,11a,11b,12,13, 13a-octadecahydro-2H-cyclopenta[a]chrysen-9-yl) oxy) carbonyl)-2,2-dimethylcyclobutane-1-carboxylic acid and (1R,3S)-3-((((3aR,5aR,5bR,7aR,9S,11aR,11bR,13aS)-3a-((1-hydroxy-2-methyl propan-2-yl)carbamoyl)-1-isopropyl-5a,5b,8,8,11a-pentamethyl-2-oxo-3,3a,4,5, 5a,5b,6,7,7a, 8,9,10,11,11a,11b,12,13,13a-octadecahydro-2H-cyclopenta[a]chrysen-9-yl)oxy) carbonyl)-2,2-dimethylcyclobutane-1-carboxylic acid or pharmaceutically acceptable salts thereof.

4. A pharmaceutical composition comprising a compound according to claim 1 and at least one pharmaceutically acceptable excipient.

5. The pharmaceutical composition according to claim 4, wherein the pharmaceutically acceptable excipient is a carrier or diluent.

6. A method of treating HIV in a subject in need thereof comprising administering to the subject a therapeutically effective amount of a compound according to claim 1.

7. A method of treating HIV in a subject in need thereof comprising administering to the subject the pharmaceutical composition according to claim 4 comprising a therapeutically effective amount of the compound.

8. A pharmaceutical composition comprising a compound according to claim 3 and at least one pharmaceutically acceptable excipient.

9. A method of treating HIV in a subject in need thereof comprising administering to the subject a therapeutically effective amount of a compound according to claim 3.

\* \* \* \* \*